(12) United States Patent
Malten et al.

(10) Patent No.: US 8,883,436 B2
(45) Date of Patent: Nov. 11, 2014

(54) METHOD OF ANALYZING CELLULOSE DECAY IN LIGNOCELLULOSIC MATERIAL HYDROLYSIS

(75) Inventors: Marco Malten, Copenhagen (DK); Keith McFarland, Davis, CA (US)

(73) Assignee: Novozymes A/S, Bagsraed (DK)

( * ) Notice: Subject to any disclaimer, the term of this patent is extended or adjusted under 35 U.S.C. 154(b) by 21 days.

(21) Appl. No.: 13/379,555

(22) PCT Filed: Jul. 13, 2010

(86) PCT No.: PCT/US2010/041869
§ 371 (c)(1),
(2), (4) Date: Mar. 19, 2012

(87) PCT Pub. No.: WO2011/008785
PCT Pub. Date: Jan. 20, 2011

(65) Prior Publication Data
US 2012/0190054 A1 Jul. 26, 2012

Related U.S. Application Data

(60) Provisional application No. 61/226,538, filed on Jul. 17, 2009.

(51) Int. Cl.
*C12Q 1/34* (2006.01)
*C12Q 1/44* (2006.01)

(52) U.S. Cl.
CPC ............ *C12Q 1/34* (2013.01); *G01N 2333/924* (2013.01)
USPC ................... 435/18; 435/23; 435/25; 435/28; 435/288.7

(58) Field of Classification Search
None
See application file for complete search history.

(56) References Cited

U.S. PATENT DOCUMENTS

2007/0166805 A1    7/2007   Cosgrove et al.

OTHER PUBLICATIONS

Poincelot et al. Appl. Microbiol. (May 1972) 23(5), 875-879.*
Cote et al. Electrophoresis (1991) 12, 69-74.*
Bichet-Hebe et al. J. Microbiol. Methods (1999) 37, 101-109.*
Leisola et al. Analyt. Biochem. (1976) 70, 592-599.*
Du et al. Appl. Biochem. Biotechnol. (2010) 161, 313-317.*
Schwander et al., 2000. Fluorescent Dyes. Ullmann's Encyclopedia of Industrial Chemistry.
Liu et al, Spectroscopy Spectral Analysis, vol. 29, No. 5, pp. 1341-1344 (2009) eng abstract.
Hoch, 2005, Mycologia, 97(3), pp. 580-588.
Isabelle, 1999, J Microbiol Methods 37, 101-109.
Smith, 1977, Appl Environ Microbiol 33(4), 980-981.
Yamada, 2004, Biosci Biotechnol Biochem 69(1), 45-50.

* cited by examiner

*Primary Examiner* — Nashaat Nashed
(74) *Attorney, Agent, or Firm* — Kelly Reynolds

(57) ABSTRACT

Enzymes and/or polypeptides and/or mixtures of interest are evaluated during hydrolysis of cellulosic material by the use of indicator constituents such as fluorescent agents, resulting in efficient high-throughput analysis of enzymes and/or polypeptides. A high-throughput assay for the analysis of inter alia, pretreated corn stover (PCS) hydrolysis is also disclosed.

8 Claims, 27 Drawing Sheets

SEQUENCE LISTING

<160> NUMBER OF SEQ ID NOS: 11

<210> SEQ ID NO 1
<211> LENGTH: 483
<212> TYPE: PRT
<213> ORGANISM: Bacillus licheniformis

<400> SEQUENCE: 1

```
Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
```

```
                145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Asn Glu Asn Gly Asn
                180                 185                 190
Tyr Asp Tyr Leu Met Tyr Ala Asp Ile Asp Tyr Asp His Pro Asp Val
                195                 200                 205
Ala Ala Glu Ile Lys Arg Trp Gly Thr Trp Tyr Ala Asn Glu Leu Gln
            210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
                260                 265                 270
Tyr Leu Asn Lys Thr Asn Phe Asn His Ser Val Phe Asp Val Pro Leu
            275                 280                 285
His Tyr Gln Phe His Ala Ala Ser Thr Gln Gly Gly Gly Tyr Asp Met
        290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Asp Ser Gln Arg Glu Ile Pro Ala Leu Lys His Lys Ile
    370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
            420                 425                 430
Gly Gly Ala Lys Arg Met Tyr Val Gly Arg Gln Asn Ala Gly Glu Thr
        435                 440                 445
Trp His Asp Ile Thr Gly Asn Arg Ser Glu Pro Val Val Ile Asn Ser
    450                 455                 460
Glu Gly Trp Gly Glu Phe His Val Asn Gly Gly Ser Val Ser Ile Tyr
465                 470                 475                 480
Val Gln Arg

<210> SEQ ID NO 2
<211> LENGTH: 480
<212> TYPE: PRT
<213> ORGANISM: Bacillus amyloliquefaciens

<400> SEQUENCE: 2

Val Asn Gly Thr Leu Met Gln Tyr Phe Glu Trp Tyr Thr Pro Asn Asp
1               5                   10                  15
Gly Gln His Trp Lys Arg Leu Gln Asn Asp Ala Glu His Leu Ser Asp
                20                  25                  30
Ile Gly Ile Thr Ala Val Trp Ile Pro Pro Ala Tyr Lys Gly Leu Ser
```

```
                 35                  40                  45
Gln Ser Asp Asn Gly Tyr Gly Pro Tyr Asp Leu Tyr Asp Leu Gly Glu
         50                  55                  60

Phe Gln Gln Lys Gly Thr Val Arg Thr Lys Tyr Gly Thr Lys Ser Glu
 65                  70                  75                  80

Leu Gln Asp Ala Ile Gly Ser Leu His Ser Arg Asn Val Gln Val Tyr
                 85                  90                  95

Gly Asp Val Val Leu Asn His Lys Ala Gly Ala Asp Ala Thr Glu Asp
                100                 105                 110

Val Thr Ala Val Glu Val Asn Pro Ala Asn Arg Asn Gln Glu Thr Ser
            115                 120                 125

Glu Glu Tyr Gln Ile Lys Ala Trp Thr Asp Phe Arg Phe Pro Gly Arg
        130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
450                 455                 460
```

Asp Gly Trp Gly Glu Phe His Val Asn Asp Gly Ser Val Ser Ile Tyr
465                 470                 475                 480

<210> SEQ ID NO 3
<211> LENGTH: 514
<212> TYPE: PRT
<213> ORGANISM: Bacillus stearothermophilus

<400> SEQUENCE: 3

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285

Ala Pro Leu His Asn Lys Phe Tyr Thr Ala Ser Lys Ser Gly Gly Thr
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp

-continued

```
                355                 360                 365
Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp

<210> SEQ ID NO 4
<211> LENGTH: 478
<212> TYPE: PRT
<213> ORGANISM: Aspergillus oryzae

<400> SEQUENCE: 4

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
                20                  25                  30

Ala Asp Gln Lys Tyr Cys Gly Gly Thr Trp Gln Gly Ile Ile Asp Lys
            35                  40                  45

Leu Asp Tyr Ile Gln Gly Met Gly Phe Thr Ala Ile Trp Ile Thr Pro
        50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
```

```
                    210                 215                 220
Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                    245                 250                 255

Pro Leu Leu Asn Ala Phe Lys Ser Thr Ser Gly Ser Met Asp Asp Leu
                260                 265                 270

Tyr Asn Met Ile Asn Thr Val Lys Ser Asp Cys Pro Asp Ser Thr Leu
            275                 280                 285

Leu Gly Thr Phe Val Glu Asn His Asp Asn Pro Arg Phe Ala Ser Tyr
        290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                    325                 330                 335

Gly Gly Asn Asp Pro Ala Asn Arg Glu Ala Thr Trp Leu Ser Gly Tyr
                340                 345                 350

Pro Thr Asp Ser Glu Leu Tyr Lys Leu Ile Ala Ser Ala Asn Ala Ile
            355                 360                 365

Arg Asn Tyr Ala Ile Ser Lys Asp Thr Gly Phe Val Thr Tyr Lys Asn
        370                 375                 380

Trp Pro Ile Tyr Lys Asp Asp Ile Thr Ile Ala Met Arg Lys Gly Thr
385                 390                 395                 400

Asp Gly Ser Gln Ile Val Thr Ile Leu Ser Asn Lys Gly Ala Ser Gly
                    405                 410                 415

Asp Ser Tyr Thr Leu Ser Leu Ser Gly Ala Gly Tyr Thr Ala Gly Gln
                420                 425                 430

Gln Leu Thr Glu Val Ile Gly Cys Thr Thr Val Thr Val Gly Ser Asp
            435                 440                 445

Gly Asn Val Pro Val Pro Met Ala Gly Gly Leu Pro Arg Val Leu Tyr
        450                 455                 460

Pro Thr Glu Lys Leu Ala Gly Ser Lys Ile Cys Ser Ser Ser
465                 470                 475

<210> SEQ ID NO 5
<211> LENGTH: 586
<212> TYPE: PRT
<213> ORGANISM: Artificial Sequence
<220> FEATURE:
<223> OTHER INFORMATION: Synthetic Construct

<400> SEQUENCE: 5

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
                20                  25                  30

Ala Asp Gln Lys Tyr Cys Gly Gly Thr Trp Gln Gly Ile Ile Asp Lys
            35                  40                  45

Leu Asp Tyr Ile Gln Gly Met Gly Phe Thr Ala Ile Trp Ile Thr Pro
        50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
```

```
            100                 105                 110
Tyr Leu Met Val Asp Val Ala Asn His Met Gly Tyr Asp Gly Pro
        115                 120                 125
Gly Ser Ser Val Asp Tyr Ser Val Phe Val Pro Phe Asn Ser Ala Ser
        130                 135             140
Tyr Phe His Pro Phe Cys Phe Ile Gln Asn Trp Asn Asp Gln Thr Gln
145                 150                 155                 160
Val Glu Asp Cys Trp Leu Gly Asp Asn Thr Val Ser Leu Pro Asp Leu
                165                 170                 175
Asp Thr Thr Lys Asp Val Val Lys Asn Glu Trp Tyr Asp Trp Val Gly
                180                 185                 190
Ser Leu Val Ser Asn Tyr Ser Ile Asp Gly Leu Arg Ile Asp Thr Val
                195                 200                 205
Lys His Val Gln Lys Asp Phe Trp Pro Gly Tyr Asn Lys Ala Ala Gly
        210                 215                 220
Val Tyr Cys Ile Gly Glu Val Leu Asp Gly Asp Pro Ala Tyr Thr Cys
225                 230                 235                 240
Pro Tyr Gln Glu Val Leu Asp Gly Val Leu Asn Tyr Pro Ile Tyr Tyr
                245                 250                 255
Pro Leu Leu Asn Ala Phe Lys Ser Thr Ser Gly Ser Met Asp Asp Leu
                260                 265                 270
Tyr Asn Met Ile Asn Thr Val Lys Ser Asp Cys Pro Asp Ser Thr Leu
                275                 280                 285
Leu Gly Thr Phe Val Glu Asn His Asp Asn Pro Arg Phe Ala Ser Tyr
        290                 295                 300
Thr Asn Asp Ile Ala Leu Ala Lys Asn Val Ala Ala Phe Ile Ile Leu
305                 310                 315                 320
Asn Asp Gly Ile Pro Ile Ile Tyr Ala Gly Gln Glu Gln His Tyr Ala
                325                 330                 335
Gly Gly Asn Asp Pro Ala Asn Arg Glu Ala Thr Trp Leu Ser Gly Tyr
                340                 345                 350
Pro Thr Asp Ser Glu Leu Tyr Lys Leu Ile Ala Ser Ala Asn Ala Ile
                355                 360                 365
Arg Asn Tyr Ala Ile Ser Lys Asp Thr Gly Phe Val Thr Tyr Lys Asn
        370                 375                 380
Trp Pro Ile Tyr Lys Asp Asp Thr Thr Ile Ala Met Arg Lys Gly Thr
385                 390                 395                 400
Asp Gly Ser Gln Ile Val Thr Ile Leu Ser Asn Lys Gly Ala Ser Gly
                405                 410                 415
Asp Ser Tyr Thr Leu Ser Leu Ser Gly Ala Gly Tyr Thr Ala Gly Gln
                420                 425                 430
Gln Leu Thr Glu Val Ile Gly Cys Thr Thr Val Thr Val Asp Ser Ser
                435                 440                 445
Gly Asp Val Pro Val Pro Met Ala Gly Gly Leu Pro Arg Val Leu Tyr
        450                 455                 460
Pro Thr Glu Lys Leu Ala Gly Ser Lys Ile Cys Ser Ser Ser Gly Ala
465                 470                 475                 480
Thr Ser Pro Gly Gly Ser Ser Gly Ser Val Glu Val Thr Phe Asp Val
                485                 490                 495
Tyr Ala Thr Thr Val Tyr Gly Gln Asn Ile Tyr Ile Thr Gly Asp Val
                500                 505                 510
Ser Glu Leu Gly Asn Trp Thr Pro Ala Asn Gly Val Ala Leu Ser Ser
                515                 520                 525
```

```
Ala Asn Tyr Pro Thr Trp Ser Ala Thr Ile Ala Leu Pro Ala Asp Thr
        530                 535                 540

Thr Ile Gln Tyr Lys Tyr Val Asn Ile Asp Gly Ser Thr Val Ile Trp
545                 550                 555                 560

Glu Asp Ala Ile Ser Asn Arg Glu Ile Thr Thr Pro Ala Ser Gly Thr
                565                 570                 575

Tyr Thr Glu Lys Asp Thr Trp Asp Glu Ser
        580                 585

<210> SEQ ID NO 6
<211> LENGTH: 558
<212> TYPE: PRT
<213> ORGANISM: Artificial Sequence
<220> FEATURE:
<223> OTHER INFORMATION: Rhizomucor pusillus amylase with linker and SBD
      from A. rolfsii

<400> SEQUENCE: 6

Ser Pro Leu Pro Gln Gln Gln Arg Tyr Gly Lys Arg Ala Thr Ser Asp
1               5                   10                  15

Asp Trp Lys Ser Lys Ala Ile Tyr Gln Leu Leu Thr Asp Arg Phe Gly
            20                  25                  30

Arg Ala Asp Asp Ser Thr Ser Asn Cys Ser Asn Leu Ser Asn Tyr Cys
        35                  40                  45

Gly Gly Thr Tyr Glu Gly Ile Thr Lys His Leu Asp Tyr Ile Ser Gly
    50                  55                  60

Met Gly Phe Asp Ala Ile Trp Ile Ser Pro Ile Pro Lys Asn Ser Asp
65                  70                  75                  80

Gly Gly Tyr His Gly Tyr Trp Ala Thr Asp Phe Tyr Gln Leu Asn Ser
                85                  90                  95

Asn Phe Gly Asp Glu Ser Gln Leu Lys Ala Leu Ile Gln Ala Ala His
            100                 105                 110

Glu Arg Asp Met Tyr Val Met Leu Asp Val Val Ala Asn His Ala Gly
        115                 120                 125

Pro Thr Ser Asn Gly Tyr Ser Gly Tyr Thr Phe Gly Asp Ala Ser Leu
    130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                165                 170                 175

Asp Asn Val Ala Ile Leu Asn Asp Ile Val Ser Gly Trp Val Gly Asn
            180                 185                 190

Tyr Ser Phe Asp Gly Ile Arg Ile Asp Thr Val Lys His Ile Arg Lys
        195                 200                 205

Asp Phe Trp Thr Gly Tyr Ala Glu Ala Ala Gly Val Phe Ala Thr Gly
    210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                245                 250                 255

Phe Val Ser Lys Ser Lys Gly Phe Ser Arg Ile Ser Glu Met Leu Gly
            260                 265                 270

Ser Asn Arg Asn Ala Phe Glu Asp Thr Ser Val Leu Thr Thr Phe Val
        275                 280                 285

Asp Asn His Asp Asn Pro Arg Phe Leu Asn Ser Gln Ser Asp Lys Ala
```

```
            290                 295                 300
Leu Phe Lys Asn Ala Leu Thr Tyr Val Leu Leu Gly Glu Gly Ile Pro
305                 310                 315                 320

Ile Val Tyr Tyr Gly Ser Glu Gln Gly Phe Ser Gly Gly Ala Asp Pro
                325                 330                 335

Ala Asn Arg Glu Val Leu Trp Thr Thr Asn Tyr Asp Thr Ser Ser Asp
            340                 345                 350

Leu Tyr Gln Phe Ile Lys Thr Val Asn Ser Val Arg Met Lys Ser Asn
        355                 360                 365

Lys Ala Val Tyr Met Asp Ile Tyr Val Gly Asp Asn Ala Tyr Ala Phe
370                 375                 380

Lys His Gly Asp Ala Leu Val Val Leu Asn Asn Tyr Gly Ser Gly Ser
385                 390                 395                 400

Thr Asn Gln Val Ser Phe Ser Val Ser Gly Lys Phe Asp Ser Gly Ala
                405                 410                 415

Ser Leu Met Asp Ile Val Ser Asn Ile Thr Thr Val Ser Ser Asp
            420                 425                 430

Gly Thr Val Thr Phe Asn Leu Lys Asp Gly Leu Pro Ala Ile Phe Thr
        435                 440                 445

Ser Ala Gly Ala Thr Ser Pro Gly Gly Ser Ser Gly Ser Val Glu Val
450                 455                 460

Thr Phe Asp Val Tyr Ala Thr Val Tyr Gly Gln Asn Ile Tyr Ile
465                 470                 475                 480

Thr Gly Asp Val Ser Glu Leu Gly Asn Trp Thr Pro Ala Asn Gly Val
                485                 490                 495

Ala Leu Ser Ser Ala Asn Tyr Pro Thr Trp Ser Ala Thr Ile Ala Leu
            500                 505                 510

Pro Ala Asp Thr Thr Ile Gln Tyr Lys Tyr Val Asn Ile Asp Gly Ser
        515                 520                 525

Thr Val Ile Trp Glu Asp Ala Ile Ser Asn Arg Glu Ile Thr Thr Pro
530                 535                 540

Ala Ser Gly Thr Tyr Thr Glu Lys Asp Thr Trp Asp Glu Ser
545                 550                 555

<210> SEQ ID NO 7
<211> LENGTH: 450
<212> TYPE: PRT
<213> ORGANISM: Rhizomucor pusillus

<400> SEQUENCE: 7

Ser Pro Leu Pro Gln Gln Arg Tyr Gly Lys Arg Ala Thr Ser Asp
1               5                   10                  15

Asp Trp Lys Gly Lys Ala Ile Tyr Gln Leu Leu Thr Arg Phe Gly
                20                  25                  30

Arg Ala Asp Asp Ser Thr Ser Asn Cys Ser Asn Leu Ser Asn Tyr Cys
            35                  40                  45

Gly Gly Thr Tyr Glu Gly Ile Thr Lys His Leu Asp Tyr Ile Ser Gly
        50                  55                  60

Met Gly Phe Asp Ala Ile Trp Ile Ser Pro Ile Pro Lys Asn Ser Asp
65                  70                  75                  80

Gly Gly Tyr His Gly Tyr Trp Ala Thr Asp Phe Tyr Gln Leu Asn Ser
                85                  90                  95

Asn Phe Gly Asp Glu Ser Gln Leu Lys Ala Leu Ile Gln Ala Ala His
            100                 105                 110
```

Glu Arg Asp Met Tyr Val Met Leu Asp Val Val Ala Asn His Ala Gly
115                 120                 125

Pro Thr Ser Asn Gly Tyr Ser Gly Tyr Thr Phe Gly Asp Ala Ser Leu
130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                165                 170                 175

Asp Asn Val Ala Ile Leu Asn Asp Ile Val Ser Gly Trp Val Gly Asn
                180                 185                 190

Tyr Ser Phe Asp Gly Ile Arg Ile Asp Thr Val Lys His Ile Arg Lys
                195                 200                 205

Asp Phe Trp Thr Gly Tyr Ala Glu Ala Ala Gly Val Phe Ala Thr Gly
            210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                245                 250                 255

Phe Val Ser Lys Ser Lys Gly Phe Ser Arg Ile Ser Glu Met Leu Gly
                260                 265                 270

Ser Asn Arg Asn Ala Phe Glu Asp Thr Ser Val Leu Thr Thr Phe Val
                275                 280                 285

Asp Asn His Asp Asn Pro Arg Phe Leu Asn Ser Gln Ser Asp Lys Ala
                290                 295                 300

Leu Phe Lys Asn Ala Leu Thr Tyr Val Leu Leu Gly Glu Gly Ile Pro
305                 310                 315                 320

Ile Val Tyr Tyr Gly Ser Glu Gln Gly Phe Ser Gly Gly Ala Asp Pro
                325                 330                 335

Ala Asn Arg Glu Val Leu Trp Thr Thr Asn Tyr Asp Thr Ser Ser Asp
                340                 345                 350

Leu Tyr Gln Phe Ile Lys Thr Val Asn Ser Val Arg Met Lys Ser Asn
                355                 360                 365

Lys Ala Val Tyr Met Asp Ile Tyr Val Gly Asp Asn Ala Tyr Ala Phe
370                 375                 380

Lys His Gly Asp Ala Leu Val Val Leu Asn Asn Tyr Gly Ser Gly Ser
385                 390                 395                 400

Thr Asn Gln Val Ser Phe Ser Val Ser Gly Lys Phe Asp Ser Gly Ala
                405                 410                 415

Ser Leu Met Asp Ile Val Ser Asn Ile Thr Thr Thr Val Ser Ser Asp
                420                 425                 430

Gly Thr Val Thr Phe Asn Leu Lys Asp Gly Leu Pro Ala Ile Phe Thr
                435                 440                 445

Ser Ala
450

<210> SEQ ID NO 8
<211> LENGTH: 37
<212> TYPE: PRT
<213> ORGANISM: Aspergillus niger

<400> SEQUENCE: 8

Thr Gly Gly Thr Thr Thr Thr Ala Thr Pro Thr Gly Ser Gly Ser Val
1               5                   10                  15

Thr Ser Thr Ser Lys Thr Thr Ala Thr Ala Ser Lys Thr Ser Thr Ser
                20                  25                  30

-continued

```
Thr Ser Ser Thr Ser
        35

<210> SEQ ID NO 9
<211> LENGTH: 108
<212> TYPE: PRT
<213> ORGANISM: Aspergillus niger

<400> SEQUENCE: 9

Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Glu Thr Ser Asp Gly Ile Ala Leu Ser Ala Asp Lys Tyr
        35                  40                  45

Thr Ser Ser Asp Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Thr Ser Thr Ala Thr Val Thr Asp Thr Trp Arg
            100                 105

<210> SEQ ID NO 10
<211> LENGTH: 574
<212> TYPE: PRT
<213> ORGANISM: Artificial Sequence
<220> FEATURE:
<223> OTHER INFORMATION: Hybrid of Meripilus giganteus amylase with A.
      rolfsii SBD

<400> SEQUENCE: 10

Arg Pro Thr Val Phe Asp Ala Gly Ala Asp Ala His Ser Leu His Ala
1               5                   10                  15

Arg Ala Pro Ser Gly Ser Lys Asp Val Ile Ile Gln Met Phe Glu Trp
            20                  25                  30

Asn Trp Asp Ser Val Ala Ala Glu Cys Thr Asn Phe Ile Gly Pro Ala
        35                  40                  45

Gly Tyr Gly Phe Val Gln Val Ser Pro Pro Gln Glu Thr Ile Gln Gly
    50                  55                  60

Ala Gln Trp Trp Thr Asp Tyr Gln Pro Val Ser Tyr Thr Leu Thr Gly
65                  70                  75                  80

Lys Arg Gly Asp Arg Ser Gln Phe Ala Asn Met Ile Thr Thr Cys His
                85                  90                  95

Ala Ala Gly Val Gly Val Ile Val Asp Thr Ile Trp Asn His Met Ala
            100                 105                 110

Gly Val Asp Ser Gly Thr Gly Thr Ala Gly Ser Ser Phe Thr His Tyr
        115                 120                 125

Asn Tyr Pro Gly Ile Tyr Gln Asn Gln Asp Phe His His Cys Gly Leu
    130                 135                 140

Glu Pro Gly Asp Asp Ile Val Asn Tyr Asp Asn Ala Val Glu Val Gln
145                 150                 155                 160

Thr Cys Glu Leu Val Asn Leu Ala Asp Leu Ala Thr Asp Thr Glu Tyr
                165                 170                 175

Val Arg Gly Arg Leu Ala Gln Tyr Gly Asn Asp Leu Leu Ser Leu Gly
            180                 185                 190
```

```
Ala Asp Gly Leu Arg Leu Asp Ala Ser Lys His Ile Pro Val Gly Asp
            195                 200                 205

Ile Ala Asn Ile Leu Ser Arg Leu Ser Arg Ser Val Tyr Ile Thr Gln
    210                 215                 220

Glu Val Ile Phe Gly Ala Gly Glu Pro Ile Thr Pro Asn Gln Tyr Thr
225                 230                 235                 240

Gly Asn Gly Asp Val Gln Glu Phe Arg Tyr Thr Ser Ala Leu Lys Asp
                245                 250                 255

Ala Phe Leu Ser Ser Gly Ile Ser Asn Leu Gln Asp Phe Glu Asn Arg
            260                 265                 270

Gly Trp Val Pro Gly Ser Gly Ala Asn Val Phe Val Asn His Asp
            275                 280                 285

Thr Glu Arg Asn Gly Ala Ser Leu Asn Asn Ser Pro Ser Asn Thr
        290                 295                 300

Tyr Val Thr Ala Thr Ile Phe Ser Leu Ala His Pro Tyr Gly Thr Pro
305                 310                 315                 320

Thr Ile Leu Ser Ser Tyr Asp Gly Phe Thr Asn Thr Asp Ala Gly Ala
                325                 330                 335

Pro Asn Asn Asn Val Gly Thr Cys Ser Thr Ser Gly Gly Ala Asn Gly
            340                 345                 350

Trp Leu Cys Gln His Arg Trp Thr Ala Ile Ala Gly Met Val Gly Phe
            355                 360                 365

Arg Asn Asn Val Gly Ser Ala Ala Leu Asn Asn Trp Gln Ala Pro Gln
            370                 375                 380

Ser Gln Gln Ile Ala Phe Gly Arg Gly Ala Leu Gly Phe Val Ala Ile
385                 390                 395                 400

Asn Asn Ala Asp Ser Ala Trp Ser Thr Thr Phe Thr Thr Ser Leu Pro
            405                 410                 415

Asp Gly Ser Tyr Cys Asp Val Ile Ser Gly Lys Ala Ser Gly Ser Ser
            420                 425                 430

Cys Thr Gly Ser Ser Phe Thr Val Ser Gly Gly Lys Leu Thr Ala Thr
            435                 440                 445

Val Pro Ala Arg Ser Ala Ile Ala Val His Thr Gly Gln Lys Gly Ser
            450                 455                 460

Gly Gly Gly Ala Thr Ser Pro Gly Gly Ser Ser Gly Ser Val Glu Val
465                 470                 475                 480

Thr Phe Asp Val Tyr Ala Thr Thr Val Tyr Gly Gln Asn Ile Tyr Ile
                485                 490                 495

Thr Gly Asp Val Ser Glu Leu Gly Asn Trp Thr Pro Ala Asn Gly Val
            500                 505                 510

Ala Leu Ser Ser Ala Asn Tyr Pro Thr Trp Ser Ala Thr Ile Ala Leu
            515                 520                 525

Pro Ala Asp Thr Thr Ile Gln Tyr Lys Tyr Val Asn Ile Asp Gly Ser
            530                 535                 540

Thr Val Ile Trp Glu Asp Ala Ile Ser Asn Arg Glu Ile Thr Thr Pro
545                 550                 555                 560

Ala Ser Gly Thr Tyr Thr Glu Lys Asp Thr Trp Asp Glu Ser
            565                 570
```

```
<210> SEQ ID NO 11
<211> LENGTH: 355
<212> TYPE: PRT
<213> ORGANISM: Thermoascus aurantiacus

<400> SEQUENCE: 11

Met Arg Leu Val Ala Ser Leu Thr Ala Pro Val Phe Pro Ala Ala Val
1               5                   10                  15

Asn Val Leu Glu Ile Thr Leu Ser Gln Val Ser Val Val Gln Asn Thr
            20                  25                  30

Gly Ser Asp Glu Asn Phe Phe Lys Asp Pro Ala Pro Val Leu Val Ala
        35                  40                  45

Leu Ser Val Lys Arg Ala Ser Ser Tyr Asn Thr Leu Ile Lys Ala Leu
    50                  55                  60

Ser Phe Val His Leu Lys Lys Val Ser Val Tyr Arg Asp Gly Ser Glu
65                  70                  75                  80

Val Gln Phe Glu Gly Ile Leu Ser Arg Tyr Lys Ser Thr Gly Leu Ser
                85                  90                  95

Arg Asp Ala Phe Thr Tyr Leu Ala Pro Gly Glu Ser Val Glu Asp Val
            100                 105                 110

Phe Asp Ile Ala Ser Thr Tyr Asp Leu Thr Ser Gly Gly Pro Val Thr
        115                 120                 125

Ile Arg Thr Glu Gly Val Val Pro Tyr Ala Thr Ala Asn Ser Thr Asp
    130                 135                 140

Ile Ala Gly Tyr Ile Ser Tyr Ser Ser Asn Val Leu Thr Ile Asp Val
145                 150                 155                 160

Asp Gly Ala Ala Ala Thr Val Ser Lys Ala Ile Thr Pro Leu Asp
                165                 170                 175

Arg Arg Thr Arg Ile Ser Ser Cys Ser Gly Ser Arg Gln Ser Ala Leu
            180                 185                 190

Thr Thr Ala Leu Arg Asn Ala Ala Ser Leu Ala Asn Ala Ala Ala Asp
        195                 200                 205

Ala Ala Gln Ser Gly Ser Ala Ser Lys Phe Ser Glu Tyr Phe Lys Thr
    210                 215                 220

Thr Ser Ser Ser Thr Arg Gln Thr Val Ala Ala Arg Leu Arg Ala Val
225                 230                 235                 240

Ala Arg Glu Ala Ser Ser Ser Ser Gly Ala Thr Thr Tyr Tyr Cys
                245                 250                 255

Asp Asp Pro Tyr Gly Tyr Cys Ser Ser Asn Val Leu Ala Tyr Thr Leu
            260                 265                 270

Pro Ser Tyr Asn Ile Ile Ala Asn Cys Asp Ile Phe Tyr Thr Tyr Leu
        275                 280                 285

Pro Ala Leu Thr Ser Thr Cys His Ala Gln Asp Gln Ala Thr Thr Ala
    290                 295                 300

Leu His Glu Phe Thr His Ala Pro Gly Val Tyr Ser Pro Gly Thr Asp
305                 310                 315                 320

Asp Leu Ala Tyr Gly Tyr Gln Ala Ala Met Gly Leu Ser Ser Ser Gln
                325                 330                 335

Ala Val Met Asn Ala Asp Thr Tyr Ala Leu Tyr Ala Asn Ala Ile Tyr
            340                 345                 350

Leu Gly Cys
355
```

METHOD OF ANALYZING CELLULOSE DECAY IN LIGNOCELLULOSIC MATERIAL HYDROLYSIS

CROSS-REFERENCE TO RELATED APPLICATION

This application is a 35 U.S.C. 371 national application of PCT/US2010/041869 filed on Jul. 13, 2010 and claims priority from U.S. provisional application Ser. No. 61/226,538 filed on Jul. 17, 2009, which applications are fully incorporated herein by reference.

REFERENCE TO A SEQUENCE LISTING

This application contains a Sequence Listing in computer readable form. The computer readable form is incorporated herein by reference.

BACKGROUND

1. Technical Field

The present disclosure relates to methods of analyzing, screening and/or evaluating enzyme(s), polypeptide(s), mixtures of enzymes, mixtures of polypeptides, and/or mixtures of enzymes and polypeptides of interest. The methods are useful for, inter alia, detecting residual cellulose and evaluating hydrolysis activity of enzymes, polypeptides, or mixtures of interest. The present disclosure further relates to high-throughput assay(s), for example, a high-throughput assay for quantifying cellulolytic activity and/or cellulase activity of enzyme(s) or polypeptide(s) of interest in a pretreated corn stover (PCS) hydrolysis is disclosed.

2. Description of the Related Art

Current methods of analyzing, evaluating, or screening the hydrolysis activity of an enzyme, polypeptide, or mixtures of interest are problematic and not well designed for high-throughput analysis. For example, one method of analyzing pretreated corn stover (hereinafter referred to as "PCS") hydrolysis requires a lengthy high pressure liquid chromatography (hereinafter referred to as "HPLC") analysis for determining the quantity of sugars. Here, cellulose, in the PCS is enzymatically hydrolyzed to glucose, cellobiose, and higher beta-glucans. HPLC is used to measure the glucose and cellobiose. One of skill in the art, knowing the cellulose content of the substrate, can then use this information to calculate the percent conversion of cellulose into sugars. Accordingly, cellulolytic activity of the enzymes in the hydrolysis can be measured. However, the HPLC step is time consuming and laborious. Assays using HPLC are not suitable for high-throughput analysis, and/or a quick analysis of multiple enzymes of interests in a single assay.

Attempts have been made to improve the HPLC assay using a pipettable substrate loaded in deep well plates; however post-hydrolysis HPLC sugar analysis is still required. The HPLC assay is time-consuming, for example, a 96 well plate takes approximately 19 hours of HPLC time. The attempted improvements are problematic in that they include time-consuming filtration, pipetting, and dilution steps prior to HPLC.

Problems with the known assays lead to higher research costs, tedious assay formatting, as well as time-consuming enzyme activity evaluation. Accordingly, there is a continuing need for assays and analysis methods having improved accuracy and/or reduced performance time, having excellent accuracy, an excellent reaction rate, and/or excellent cellulose conversion, especially where high-throughput analysis is desirable.

SUMMARY

It has now been found that the addition of indicator constituent(s) or brightening additive(s), such as fluorescent indicator compounds and/or enhancers, to a hydrolysis reaction has a significant effect on the ability to screen and/or evaluate the performance of an enzyme(s), a polypeptide(s), and mixtures of interest in a hydrolysis reaction containing cellulosic material. For example, the addition of a fluorescent indicator compound is useful for detecting residual cellulose and evaluating hydrolysis activity of an enzyme or enzyme mixtures of interest. Accordingly, it is now possible to perform chemical assays of an enzyme(s) and/or a polypeptide(s) of interest with the benefits provided by the indicator constituents such as fluorescent indicators. Further, it is now possible to perform high-throughput assays in reduced periods of time. Moreover, it is now possible to detect residual cellulose and evaluate hydrolysis activity of an enzyme(s), polypeptide(s), or mixtures of interest in a high-throughput format. These methods are also useful for discovering enzymes of interest or polypeptides of interest with improved performance characteristics and/or quality control of manufactured enzymes, peptides, or polypeptides. In embodiments, the methods eliminate the use of HPLC and are faster by avoiding a typically lengthy HPLC assay.

A first aspect of the present disclosure relates to methods of analyzing cellulose decay in the hydrolysis of cellulosic material such as a lignocellulose hydrolysis.

A second aspect of the present disclosure relates to a method of determining whether an enzyme of interest or polypeptide of interest affects cellulose hydrolysis.

A third aspect of the present disclosure relates to a high-throughput method of analyzing enzymes or polypeptides of interest.

A fourth aspect of the present disclosure relates to a method of analyzing enzyme or polypeptide performance.

A fifth aspect of the present disclosure relates to a system for evaluating enzyme and/or polypeptide performance.

A sixth aspect of the present disclosure relates to a method of determining if a polypeptide of interest has cellulolytic enhancing activity.

A seventh aspect of the present disclosure relates to normalization methods for the above described aspects of the present disclosure.

An eighth aspect of the present disclosure relates to quality control methods. For example, quality control parameters such as enzyme activity, cellulase activity, cellulolytic enhancing activity and/or stability can be checked by a manufacturer after one or more batches of polypeptides or enzymes are produced. Further, quality control parameters such as polypeptide activity, enzyme activity, cellulase activity, cellulolytic enhancing activity and/or stability can be checked by a purchaser of an enzyme or polypeptide.

The objects of the present disclosure are met by providing a method of analyzing cellulose decay in cellulosic material (e.g., lignocellulose) hydrolysis including hydrolyzing the cellulosic material containing cellulose in a reaction medium, including an indicator constituent under conditions where the indicator constituent will stain the cellulose; and detecting a signal from the indicator constituent, wherein the intensity of the signal indicates the amount of cellulose hydrolyzed by the enzyme. In embodiments, the methods include, prior to the step of hydrolyzing, (a) contacting cellulosic material (e.g., lignocellulosic material) with an indicator constituent to form a mixture; and (b) simultaneous to or subsequent to step (a) contacting the mixture with a reaction medium including enzyme and/or polypeptide of interest.

The objects of the present disclosure are met by providing a method of analyzing cellulose decay in cellulosic material (e.g., lignocellulose) hydrolysis including the steps of: (a) contacting cellulosic material (e.g., lignocellulose) with an indicator constituent such as fluorescent indicator compound to form a mixture; (b) simultaneous to or subsequent to step (a) contacting the mixture with a reaction medium including enzyme and/or polypeptide of interest; (c) hydrolyzing the cellulosic material (e.g., lignocellulose) containing cellulose in the reaction medium under conditions where the indicator constituent such as fluorescent indicator compound will stain the cellulose; and (d) detecting a signal from the indicator constituent, wherein the intensity of the signal indicates the amount of cellulose hydrolyzed by the enzyme. In embodiments, the indicator constituent is a fluorescent indicator compound including stilbene derivatives, styryl derivatives of benzene and biphenyl, pyrazolines, bis(benzoxazol-2-yl) derivatives, coumarins, carbostyrils, or mixtures thereof.

The objects of the present disclosure are also met by providing a method of determining whether an enzyme of interest and/or polypeptide of interest affects cellulose hydrolysis, including the steps of: hydrolyzing the cellulosic material in a reaction medium including an indicator constituent under conditions where the indicator constituent or fluorescent indicator compound will affect the cellulose and produce an optical signal indicative of the presence of cellulose; and determining whether the hydrolyzed reaction has a desired optical signal, wherein the desired optical signal indicates cellulase activity of the enzyme and/or polypeptide of interest and/or the amount of cellulose hydrolyzed by the enzyme of interest. In embodiments, the methods include the steps of, prior to the hydrolysis, (a) contacting cellulosic material with an indicator constituent such as fluorescent indicator compound to form a mixture; (b) simultaneous to or subsequent to step (a) contacting the mixture with a reaction medium suitable for cellulose hydrolysis including enzyme and/or polypeptide of interest.

The objects of the present disclosure are also met by providing a method of determining whether an enzyme of interest and/or polypeptide of interest affects cellulose hydrolysis, including the steps of: (a) contacting cellulosic material with an indicator constituent such as fluorescent indicator compound to form a mixture; (b) simultaneous to or subsequent to step (a) contacting the mixture with a reaction medium suitable for cellulose hydrolysis including enzyme of interest and/or polypeptide of interest, (c) hydrolyzing the cellulosic material in a reaction medium under conditions where the indicator constituent or fluorescent indicator compound will affect the cellulose and produce an optical signal indicative of the presence of cellulose; and (d) determining whether the hydrolyzed reaction has a desired optical signal, wherein the desired optical signal indicates cellulolytic activity of the enzyme of interest and/or the amount of cellulose hydrolyzed by the enzyme of interest. In embodiments, the optical signal indicates cellulolytic activity and/or cellulolytic enhancing activity of a polypeptide of interest.

The objects of the present disclosure are also met by providing a high-throughput method of analyzing an enzyme of interest and/or polypeptide of interest, including the steps of: (a) contacting biomass with an indicator constituent such as a fluorescent compound to form a mixture; (b) simultaneous to or subsequent to step (a) contacting the mixture with a reaction medium including enzyme of interest and/or polypeptide of interest, (c) hydrolyzing the biomass including cellulose in a reaction medium under conditions where the indicator constituent such as the fluorescent indicator compound will stain the cellulose; and (d) detecting a signal from the indicator constituent, e.g., fluorescent indicator compound, wherein the intensity of the signal predicts a quality parameter of the enzyme of interest in biomass hydrolysis, and wherein the reaction mixture is disposed within a multi-well plate including at least two wells.

The objects of the present invention are also met by providing a method of determining whether an enzyme of interest and/or polypeptide of interest affects cellulose hydrolysis, including the steps of: (a) contacting biomass with an indicator constituent such as fluorescent indicator compound to form a mixture; (b) simultaneous to or subsequent to step (a) contacting the mixture with a reaction medium suitable for cellulose hydrolysis including enzyme of interest and/or polypeptide of interest, (c) hydrolyzing the biomass containing cellulose in a reaction medium under conditions where the indicator constituent such as a fluorescent indicator compound will bind to cellulose and produce an optical signal indicative of the presence of cellulose; and (d) determining whether the hydrolyzed reaction has a desired optical signal, wherein the desired optical signal indicates that the enzyme of interest and/or polypeptide of interest affects cellulose hydrolysis. These methods may also include the step of providing an enzyme of interest. These methods may also include providing a polypeptide of interest. Non-limiting examples of suitable enzymes of interest include enzyme selected from the group consisting of: (a) wild-type exo-cellobiohydrolase, wild-type endo-1,4-β-glucanase, wild-type exo-1,4-β-glucosidase, wild-type cellobiase, or combinations thereof; (b) mutated exo-cellobiohydrolase, mutated endo-1,4-β-glucanase, mutated exo-1,4-β-glucosidase, mutated cellobiase, or combinations thereof; and (c) variant exo-cellobiohydrolase, variant endo-1,4-β-glucanase, variant exo-1,4-β-glucosidase, variant cellobiase, or combinations thereof. Combinations of these wild-types, mutants and variants are also contemplated as enzyme mixtures of interest in accordance with the present disclosure. Fragments having the activity of a), b) or c) are also contemplated herein.

The objects of the present disclosure are also met by providing a method of analyzing enzyme performance including the steps of: (a) contacting lignocellulosic material with an indicator constituent such as a fluorescent indicator compound to form a mixture; (b) simultaneous to or subsequent to step (a) contacting the mixture with a reaction medium including enzyme and/or polypeptide of interest; (c) hydrolyzing the lignocellulosic material containing cellulose in the reaction medium under conditions where the indicator constituent such as the fluorescent indicator compound will stain the cellulose; and (d) detecting a signal from the indicator constituent such as the fluorescent indicator compound, wherein the intensity of the signal indicates the amount of cellulose hydrolyzed by the enzyme. Non-limiting examples of enzyme performance include an indication of cellulose decay in lignocellulose hydrolysis. Non-limiting examples of suitable enzymes of interest include enzyme selected from the group consisting of: (a) wild-type exo-cellobiohydrolase, wild-type endo-1,4-β-glucanase, wild-type exo-1,4-β-glucosidase, wild-type cellobiase, or combinations thereof; (b) mutated exo-cellobiohydrolase, mutated endo-1,4-β-glucanase, mutated exo-1,4-β-glucosidase, mutated cellobiase, or combinations thereof; and (c) variant exo-cellobiohydrolase, variant endo-1,4-β-glucanase, variant exo-1,4-β-glucosidase, variant cellobiase, or combinations thereof. Combinations of these wild-types, mutants and variants are also contemplated as enzyme mixtures of interest in accordance with the present disclosure. Fragments having the activity of a), b) or c) are also contemplated herein.

The objects of the present invention are also met by providing a method of analyzing cellulose decay in biomass hydrolysis, including the steps of: (a) contacting biomass with an indicator constituent such as a fluorescent indicator compound to form a mixture; (b) simultaneous to or subsequent to step (a) contacting the mixture with a reaction medium including enzyme of interest and/or polypeptide of interest, (c) hydrolyzing the biomass including cellulose in a reaction medium under conditions where the indicator constituent such as the fluorescent indicator compound will bind to cellulose; and (d) detecting a signal from the indicator constituent such as the fluorescent indicator compound, wherein the intensity of the signal indicates a quality parameter of the enzyme of interest and/or polypeptide of interest in biomass hydrolysis. Such methods may be performed in a system. Non-limiting examples of suitable enzymes of interest include enzyme selected from the group consisting of: (a) wild-type exo-cellobiohydrolase, wild-type endo-1,4-β-glucanase, wild-type exo-1,4-β-glucosidase, wild-type cellobiase, or combinations thereof; (b) mutated exo-cellobiohydrolase, mutated endo-1,4-β-glucanase, mutated exo-1,4-β-glucosidase, mutated cellobiase, or combinations thereof; and (c) variant exo-cellobiohydrolase, variant endo-1,4-β-glucanase, variant exo-1,4-β-glucosidase, variant cellobiase, or combinations thereof. Combinations of these wild-types, mutants and variants are also contemplated as enzyme mixtures of interest in accordance with the present disclosure. Fragments having the activity of a), b) or c) are also contemplated herein.

The objects of the present disclosure are also met by providing a method of determining whether an enzyme or polypeptide of interest affects cellulose hydrolysis, including the steps of: (a) contacting cellulosic material with a fluorescent indicator compound to form a mixture; (b) simultaneous to or subsequent to step (a) contacting the mixture with a reaction medium suitable for cellulose hydrolysis including enzyme or polypeptide of interest; (c) hydrolyzing the cellulosic material in a reaction medium under conditions where the fluorescent indicator compound will alter the cellulose and produce an optical signal indicative of the presence of cellulose; and (d) determining whether the hydrolyzed reaction has a desired optical signal, wherein the desired optical signal indicates cellulolytic activity of the enzyme or polypeptide of interest and/or the amount of cellulose hydrolyzed by the enzyme of interest.

The objects of the present disclosure are also met by providing a method of analyzing cellulose decay in cellulosic material (e.g., lignocellulose) hydrolysis, including the steps of: (a) contacting cellulosic material (e.g., lignocellulose) with a fluorescent indicator compound to form a mixture; (b) simultaneous to or subsequent to step (a) contacting the mixture with a reaction medium including enzyme and/or polypeptide of interest; (c) hydrolyzing the cellulosic material containing cellulose in the reaction medium under conditions where the fluorescent indicator compound will bind to the cellulose; and (d) detecting a signal from the fluorescent indicator compound, wherein the intensity of the signal indicates the amount of cellulose hydrolyzed by the enzyme.

The objects of the present disclosure are also met by providing a system for evaluating enzyme and/or polypeptide performance including: at least one reaction area, wherein the reaction area is for analyzing cellulose decay in cellulosic material (e.g., lignocellulose) hydrolysis, the reaction area including: at least one well for: (a) contacting cellulosic material (e.g., lignocellulose) with a fluorescent indicator compound to form a mixture; (b) simultaneous to or subsequent to step (a) contacting the mixture with a reaction medium including enzyme and/or polypeptide of interest; (c) hydrolyzing the cellulosic material (e.g., lignocellulose) containing cellulose in the reaction medium under conditions where the fluorescent indicator compound will stain the cellulose; and at least one detector suitable for detecting a signal from the fluorescent indicator compound, wherein the intensity of the signal indicates the amount of cellulose hydrolyzed by the enzyme. In one system embodiment the detector is located below the reaction medium and below the plate the reaction medium is within.

The objects of the present invention are met by providing a method of normalizing fluorescent intensity data, the method including the steps of: (a) determining the average fluorescent intensity of a hydrolysis reaction of cellulosic material (e.g., PCS) without the addition of enzyme or polypeptide; and (b) normalizing the fluorescent intensity of one or more second hydrolysis reactions using the fluorescent intensity determined in step (a).

The objects of the present invention may also be met, in embodiments, by providing a method of analyzing cellulose decay by one or more enzymes or polypeptides of interest in a hydrolysis reaction of a substrate including hydrolyzing a substrate containing cellulose in the reaction medium and subsequently adding indicator constituent where the indicator constituent will stain the cellulose; and detecting a signal from the indicator constituent, wherein the intensity of the signal indicates the amount of cellulose hydrolyzed by the enzyme of interest.

The term "cellulolytic enzyme" or "cellulase" is defined herein as one or more (several) enzymes that hydrolyze a cellulosic material. Such enzymes include endoglucanase(s), cellobiohydrolase(s), beta-glucosidase(s), or combinations thereof. Two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman N°1 filter paper, microcrystalline cellulose, bacterial cellulose, algal cellulose, cotton, pretreated lignocellulose, etc. The most common total cellulolytic activity assay is the filter paper assay using Whatman N°1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present disclosure, cellulolytic activity is determined using methods of the present disclosure or, such as for the purpose of making comparative data, determined by measuring the increase in hydrolysis of a cellulosic material by a cellulolytic mixture under the following conditions: 1-20 mg of cellulolytic enzyme protein/g of cellulose in PCS for 3-7 days at 50-65° C. compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 72 hours, sugar analysis by AMINEX® HPX-87H column (Bio-Rad Laboratories, Inc., Hercules, Calif., USA).

The term "endoglucanase" is defined herein as an endo-1, 4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present disclosure, cellobiohydrolase activity is determined on a fluorescent disaccharide derivative-4-methylumbelliferyl-β-D-lactoside according to the procedures described by van Tilbeurgh et al., 1982, *FEBS Letters* 149: 152-156 and van Tilbeurgh and Claeyssens, 1985, *FEBS Letters* 187: 283-288.

The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase activity is defined as 1.0 μmole of p-nitrophenol produced per minute at 40° C., pH 5 from 1 mM p-nitrophenyl-beta-D-glucopyranoside as substrate in 100 mM sodium citrate, 0.01% TWEEN® 20.

The term "cellulolytic enhancing activity" is defined herein as a biological activity catalyzed by a GH61 polypeptide that enhances the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at 50-65° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

The term "hemicellulolytic enzyme" or "hemicellulase" is defined herein as one or more (several) enzymes that hydrolyze a hemicellulosic material. See, for example, Shallom, D. and Shoham, Y. Microbial hemicellulases. *Current Opinion In Microbiology,* 2003, 6(3): 219-228). Hemicellulases are key components in the degradation of plant biomass. Examples of hemicellulases include, but are not limited to, an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). A most informative and updated classification of these and other carbohydrate active enzymes is available on the Carbohydrate-Active Enzymes (CAZy) database. Hemicellulolytic enzyme activities can be measured according to Ghose and Bisaria, 1987, *Pure & Appl. Chem.* 59: 1739-1752.

The term "xylan degrading activity" or "xylanolytic activity" is defined herein as a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% Triton X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

The term "xylanase" is defined herein as a 1,4-beta-D-xylan-xylohydrolase (E.C. 3.2.1.8) that catalyzes the endohydrolysis of 1,4-beta-D-xylosidic linkages in xylans. For purposes of the present disclosure, xylanase activity is determined using birchwood xylan as substrate. One unit of xylanase activity is defined as 1.0 μmole of reducing sugar (measured in glucose equivalents as described by Lever, 1972, A new reaction for colorimetric determination of carbohydrates, *Anal. Biochem* 47: 273-279) produced per minute during the initial period of hydrolysis at 50° C., pH 5 from 2 g/L birchwood xylan as substrate in 50 mM sodium acetate, 0.01% TWEEN® 20.

The term "beta-xylosidase" is defined herein as a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

The term "acetylxylan esterase" is defined herein as a carboxylesterase (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase is defined as the amount of enzyme capable of releasing 1 μmole of p-nitrophenolate anion per minute at pH 5, 25° C.

The term "feruloyl esterase" is defined herein as a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

The term "alpha-glucuronidase" is defined herein as an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methyl-glucuronic acid per minute at pH 5, 40° C.

The term "alpha-L-arabinofuranosidase" is defined herein as an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

The terms "Family 3", "Family 5", "Family 6", "Family 7", "Family 10", "Family 11", "Family 61", "GH3", "GH5", "GH6", "GH7", "GH10", "GH11", "GH61", "Cel3", "Cel5", "Cel6", or "Cel7" are defined herein as a polypeptide falling into the glycoside hydrolase Families 3, 5, 6, 7, 10, 11, and 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

The term "cellulosic material" is defined herein as any material containing cellulose. The cellulosic material can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocelluloses, which comprises cellulose, hemicellulose, and lignin.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

The term "pre-treated corn stover" or "PCS" is defined herein as a cellulosic material derived from corn stover that has been subjected to one or more pretreatment step(s).

The term "variant" is defined herein as an enzyme or a polypeptide having biological activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding one or more (several) amino acids, e.g., 1-5 amino acids, adjacent to an amino acid occupying a position.

The term "wild-type" enzyme is defined herein as an enzyme expressed by a naturally occurring microorganism such as bacterial, yeast, or filamentous fungus found in nature.

The term "parent enzyme" is defined herein as an enzyme to which a modification, e.g., substitution(s), insertion(s), deletion(s), and/or truncation(s), is made to produce the enzyme variants of the present disclosure such as an enzyme of interest. This term also refers to the polypeptide with which a variant can be compared and aligned. The parent may be a naturally occurring (wild-type) polypeptide or a variant. For instance, the parent protein may be a variant of a naturally occurring polypeptide which has been modified or altered in the amino acid sequence. A parent may also be an allelic variant, which is a polypeptide encoded by any of two or more alternative forms of a gene occupying the same chromosomal locus.

The term "isolated polypeptide" is defined herein as a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

The term "substantially pure polypeptide" is defined herein as a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5%, and even most preferably at most 0% by weight of other polypeptide material with which it is natively or recombinantly associated. It is, therefore, preferred that the substantially pure polypeptide is at least 90% pure, preferably at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

The term "mature polypeptide" is defined herein as a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. The mature polypeptide can be predicted using the SignalP program (Nielsen et al., 1997, *Protein Engineering* 10:1-6).

The term "mature polypeptide coding sequence" is defined herein as a nucleotide sequence that encodes a mature polypeptide having biological activity. The mature polypeptide coding sequence can be predicted using the SignalP program (Nielsen et al., 1997, supra).

The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment−Total Number of Gaps in Alignment)

The term "polypeptide fragment" is defined herein as a polypeptide having one or more (several) amino acids deleted from the amino and/or carboxyl terminus of a mature polypeptide; wherein the fragment has biological activity.

The term "subsequence" is defined herein as a polynucleotide having one or more (several) nucleotides deleted from the 5' and/or 3' end of a mature polypeptide coding sequence; wherein the subsequence encodes a fragment having biological activity.

The term "allelic variant" is defined herein as any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "isolated polynucleotide" is defined herein as a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

The term "substantially pure polynucleotide" is defined herein as a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably at least 100% pure by weight. The polynucleotides are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

The term "coding sequence" is defined herein as a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "nucleic acid construct" is defined herein as a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence.

The term "control sequences" is defined herein as all components necessary for the expression of a polynucleotide encoding a polypeptide. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "operably linked" is defined herein as a configuration in which a control sequence is placed at an appropriate position relative to the coding sequence of a polynucleotide such that the control sequence directs the expression of the coding sequence.

The term "expression" is defined herein as any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide and is operably linked to additional nucleotides that provide for its expression.

The term "host cell" is defined herein as any cell type that is susceptible to transformation, transfection, transduction, and the like with a nucleic acid construct or expression vector comprising a polynucleotide. The term "host cell" encompasses any progeny of a parent cell that is not identical to the parent cell due to mutations that occur during replication.

The term "improved property" is defined herein as a characteristic associated with a variant or mutant enzyme or polypeptide that is improved compared to the parent or non-mutated enzyme or polypeptide. Such improved properties include, but are not limited to, enhanced cellulolytic activity, altered temperature-dependent activity profile, thermostability, pH activity, pH stability, substrate specificity, product specificity, product stability, product activity and/or chemical stability.

The term "polypeptide" is defined herein as several amino acids linked together by peptide bonds. Non-limiting examples of polypeptides include polypeptide fragments, large proteins, small proteins. and parts of proteins.

The term "improved product specificity" is defined herein as a variant enzyme or polypeptide displaying an altered product profile relative to the parent in which the altered product profile improves the performance of the variant or polypeptide in a given application relative to the parent. The term "product profile" is defined herein as the chemical composition of the reaction products produced by enzymatic hydrolysis.

The term "mutant" is defined herein as an organism that has undergone a mutation.

The term "mutant enzyme" is defined herein as an enzyme derived from a mutant where the enzyme has an alteration when compared to the same enzyme from a parent cell to the mutant.

The term "module" is defined herein as an intelligent component that carries out well-defined tasks in a system.

The term "e.g." refers generally to an abbreviation for the Latin phrase exempli gratia. As used herein, "e.g." refers to one or more non-limiting examples. The term is non-limiting in that the object that is exemplified is not limited in scope to the specific example(s) provided.

The term "such as" is used herein to refer generally to one or more non-limiting example(s).

These and other aspects of this disclosure will be evident upon reference to the detailed description below.

BRIEF DESCRIPTION OF THE FIGURES

FIG. 5A includes values with the addition of enzyme. FIG. 5B excludes values from biomass without enzyme addition. FIG. 5C includes values with the addition of enzyme. FIG. 5D excludes values from biomass without enzyme addition. FIG. 5E includes values with the addition of enzyme. FIG. 5F excludes values from biomass without enzyme addition.

FIG. 11 shows different sets of enzymes with FB28 (solid line, closed symbol) and without FB28 (dashed line, open symbol).

DETAILED DESCRIPTION OF PREFERRED EMBODIMENTS

Figure 1A:
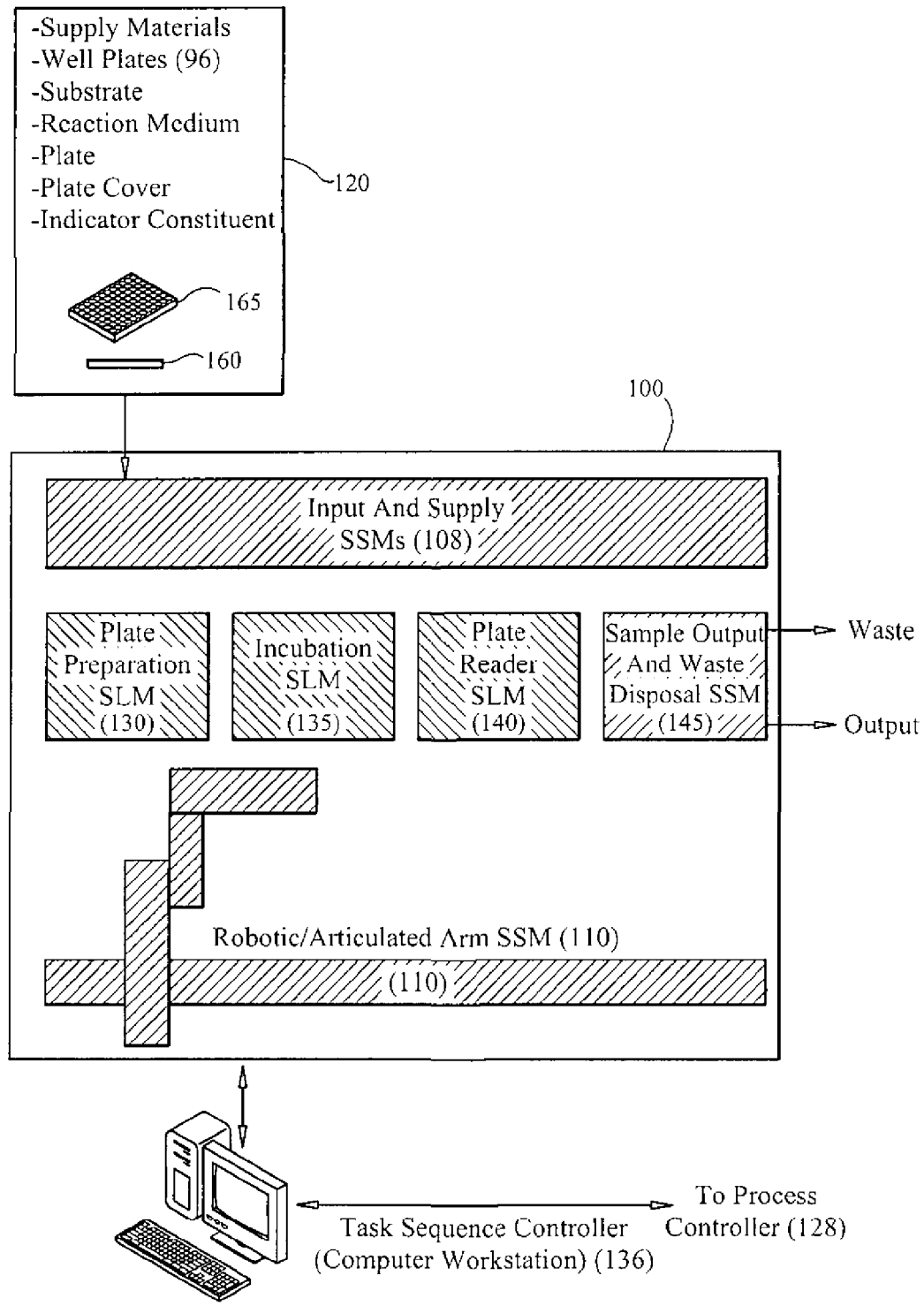
FIG. 1A is a diagram showing one embodiment of a system of the present disclosure.

It has been found that the addition of one or more indicator constituents, such as brighteners or fluorescent indicator compounds, that bind to, stain, or brighten cellulose, effectively maximizes or increases the rate at which enzymes or polypeptides of interest such as wild-type, mutant, variant and/or recombinant enzymes can be evaluated in relation to cellulosic hydrolysis. Further, it has been found that methods in accordance with the present disclosure may be carried out in high-throughput assays. This saves time while providing an accurate indication of the cellulolytic activity and/or cellulolytic enhancing activity of one or more enzyme(s), polypeptide(s), mixtures of enzymes, mixtures of polypeptides and/or mixtures of enzymes and polypeptides of interest. The methods of the present disclosure are useful in testing large quantities of polypeptide and/or enzyme samples (containing one or more enzymes and/or polypeptides, mixtures of enzymes, mixtures of polypeptides and/or mixtures of enzymes and polypeptides of interest), for example having a known protein content on a specified biomass sample(s). For example, enzyme and/or polypeptide of interest samples coming from mutagenesis libraries, wild-type screening and/or fermentation runs may be efficiently evaluated. Non-limiting examples of suitable enzymes of interest in accordance with the present disclosure include: wild-type exo-cellobiohydrolase, wild-type endo-1,4-β-glucanase, wild-type exo-1,4-β-glucosidase, wild-type cellobiase, or combinations thereof; mutated exo-cellobiohydrolase, mutated endo-1,4-β-glucanase, mutated exo-1,4-β-glucosidase, mutated cellobiase, or combinations thereof; and/or variant exo-cellobiohydrolase, variant endo-1,4-β-glucanase, variant exo-1,4-β-glucosidase, variant cellobiase, or combinations thereof. Enzymes of interest may also include enzyme cocktails such as combinations of the aforesaid enzymes of interest. Non-limiting examples of polypeptides of interest include one or more polypeptide(s) falling into the glycoside hydrolase families 3, 5, 6, 7, 10, 11, and 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. It is envisioned that mixtures of polypeptide(s) and enzyme(s) may be analyzed, for example a mix of mutated exo-cellobiohydrolase, mutated endo-1,4-β-glucanase, mutated exo-1,4-β-glucosidase, mutated cellobiase, and GH61 polypeptide having cellulolytic enhancing activity may be subjected to the assays in accordance with the present disclosure.

Without being bound by the present disclosure, it is believed that when one or more indicator constituents such as fluorescent indicator compounds contact cellulose the indicator constituent binds to or stains the cellulose. For example, staining is done under conditions suitable to promote the binding of a given indicator compound such as fluorescent indicator compounds to the cellulose. It is believed the staining procedure is effective because of the ability of the indicator constituent such as fluorescent indicator compounds or dye to bind with specificity to the cellulose, highlighting the cellulose in contrast with the rest of the reaction medium and other components therein. While minimal background highlighting is possible without ruining the accuracy of the methods in accordance with the present disclosure, background highlighting (caused by the same or similar indicator constituent) is not preferred and meant to be minimized or avoided. Without being bound by this disclosure, it is believed that the staining or binding procedure makes use of a subset of possible interactions between the indicator constituent and the cellulose component(s). These interactions may include ionic, covalent, and hydrophobic bonds.

The binding or staining allows residual cellulose to be more easily observed/measured after cellulose hydrolysis. In embodiments, the intensity of the signal from the indicator constituent such as a fluorescent indicator compound may be used to indicate a quality parameter of one or more enzymes of interest. Non-limiting examples of quality parameters include properties of one or more enzymes of interest, product specificity of one or more enzyme(s) of interest, improved properties, and/or improved product specificity of one or more enzymes of interest. In embodiments, the intensity of the signal from the indicator constituent such as a fluorescent indicator compound may be used to indicate a quality parameter of one or more polypeptides of interest.

In embodiments, a desired optical signal from bound indicator constituent such as a fluorescent indicator compound indicates that the enzyme of interest and/or polypeptide of interest affects cellulose hydrolysis. For example, a signal, such as an optical signal, may be brighter in one sample compared to another indicating that more cellulose is present in the brighter sample. Such an indication alerts one skilled in the art that the hydrolysis in the brighter sample was not as efficient or complete compared to the dull or less bright sample.

Accordingly, the present disclosure provides, inter alia, methods of analyzing cellulose decay in cellulosic material (e.g., lignocellulose) hydrolysis including the steps of hydrolyzing the cellulosic material (e.g., lignocellulose) containing cellulose in the reaction medium containing indicator constituent under conditions where the indicator constituent such as a fluorescent indicator compound will stain the cellulose; and detecting a signal from the indicator constituent such as a fluorescent indicator compound, wherein the intensity of the signal indicates the amount of cellulose hydrolyzed by the enzyme.

Further, the present disclosure provides, inter alia, methods of analyzing cellulose decay in cellulosic material (e.g., lignocellulose) hydrolysis including the steps of: (a) contacting cellulosic material (e.g., lignocellulose) with an indicator constituent such as a fluorescent indicator compound to form a mixture; (b) simultaneous to or subsequent to step (a) contacting the mixture with a reaction medium including enzyme of interest; (c) hydrolyzing the cellulosic material (e.g., lignocellulose) containing cellulose in the reaction medium under conditions where the indicator constituent such as the fluorescent indicator compound will stain the cellulose; and (d) detecting a signal from the indicator constituent such as the fluorescent indicator compound, wherein the intensity of the signal indicates the amount of cellulose hydrolyzed by the enzyme.

In embodiments, the present disclosure provides a method of determining whether an enzyme and/or polypeptide of interest affects cellulose hydrolysis, including the steps of hydrolyzing the cellulosic material in a reaction medium including indicator constituent under conditions where the indicator constituent such as a fluorescent indicator compound will affect the cellulose and produce an optical signal indicative of the presence of cellulose; and determining whether the hydrolyzed reaction has a desired optical signal, wherein the desired optical signal indicates cellulolytic activity of the enzyme of interest, cellulolytic enhancing activity of a polypeptide of interest, and/or the amount of cellulose hydrolyzed by the enzyme of interest, alone or in combination with a polypeptide of interest. In embodiments, the reaction medium includes one or more enzymes of interest, alone or in combination with one or more polypeptides of interest.

In embodiments, the present disclosure provides a method of determining whether an enzyme and/or polypeptide of interest affects cellulose hydrolysis, including the steps of: (a) contacting cellulosic material with an indicator constituent such as a fluorescent indicator compound to form a mixture;

(b) simultaneous to or subsequent to step (a) contacting the mixture with a reaction medium suitable for cellulose hydrolysis including enzyme and/or polypeptide of interest, (c) hydrolyzing the cellulosic material in a reaction medium under conditions where the indicator constituent such as a fluorescent indicator compound will affect the cellulose and produce an optical signal indicative of the presence of cellulose; and (d) determining whether the hydrolyzed reaction has a desired optical signal, wherein the desired optical signal indicates cellulolytic activity of the enzyme of interest, cellulolytic enhancing activity of the polypeptide of interest and/or the amount of cellulose hydrolyzed by the enzyme of interest. In embodiments, the reaction medium includes one or more enzymes of interest, alone or in combination with one or more polypeptides of interest.

In embodiments, the present disclosure provides a high-throughput method of analyzing enzymes of interest and/or polypeptides of interest, including the steps of: hydrolyzing the biomass including cellulose in a reaction medium including indicator constituent under conditions where an indicator constituent such as a fluorescent indicator compound will stain the cellulose; and detecting a signal from the indicator constituent, wherein the intensity of the signal predicts a quality parameter of the enzyme of interest in biomass hydrolysis, and wherein the reaction mixture is disposed within a multi-well plate including at least two wells. In embodiments, the reaction medium includes one or more enzymes of interest, alone or in combination with one or more polypeptides of interest.

In embodiments, the present disclosure provides a high-throughput method of analyzing enzymes of interest and/or polypeptides of interest including the steps of: (a) contacting biomass with an indicator constituent such as a fluorescent compound to form a mixture; (b) simultaneous to or subsequent to step (a) contacting the mixture with a reaction medium including enzyme of interest and/or polypeptide of interest, (c) hydrolyzing the biomass including cellulose in a reaction medium under conditions where the indicator constituent such as a fluorescent indicator compound will stain the cellulose; and (d) detecting a signal from the indicator constituent, wherein the intensity of the signal predicts a quality parameter of the enzyme of interest and/or polypeptide of interest in biomass hydrolysis, and wherein the reaction mixture is disposed within a multi-well plate including at least two wells.

In embodiments, the present disclosure provides a method of determining whether an enzyme of interest and/or polypeptide of interest affects cellulose hydrolysis, including the steps of: (a) contacting biomass with an indicator constituent such as a fluorescent indicator compound to form a mixture; (b) simultaneous to or subsequent to step (a) contacting the mixture with a reaction medium suitable for cellulose hydrolysis including enzyme of interest and/or polypeptide of interest, (c) hydrolyzing the biomass containing cellulose in a reaction medium under conditions where the indicator constituent such as the fluorescent indicator compound will bind to cellulose and produce an optical signal indicative of the presence of cellulose; and (d) determining whether the hydrolyzed reaction has a desired optical signal, wherein the desired optical signal indicates that the enzyme of interest and/or polypeptide of interest affects cellulose hydrolysis. These methods may also include the step of providing an enzyme of interest. Non-limiting examples of suitable enzymes of interest include enzymes selected from the group consisting of: (a) wild-type exo-cellobiohydrolase, wild-type endo-1,4-β-glucanase, wild-type exo-1,4-β-glucosidase, wild-type cellobiase, or combinations thereof; (b) mutated exo-cellobiohydrolase, mutated endo-1,4-β-glucanase, mutated exo-1,4-β-glucosidase, mutated cellobiase, or combinations thereof; and (c) a variant exo-cellobiohydrolase, variant endo-1,4-β-glucanase, variant exo-1,4-β-glucosidase, variant cellobiase, or combinations thereof. Other non-limiting examples of enzymes of interest include combinations of these wild-type, mutant, or variant enzymes. Polypeptide fragments of interest may also be evaluated by these methods. Further, these methods may also include the step of adding a polypeptide of interest such as GH61 polypeptide having cellulolytic enhancing activity.

In embodiments, the present disclosure provides a method of analyzing enzyme and/or polypeptide performance including the steps of: (a) contacting cellulosic material (e.g., lignocellulosic material) with a fluorescent indicator compound to form a mixture; (b) simultaneous to or subsequent to step (a) contacting the mixture with a reaction medium including enzyme and/or polypeptide of interest; (c) hydrolyzing the cellulosic material (e.g., lignocellulosic material) containing cellulose in the reaction medium under conditions where the fluorescent indicator compound will stain the cellulose; and (d) detecting a signal from the fluorescent indicator compound, wherein the intensity of the signal indicates the amount of cellulose hydrolyzed by the reaction medium constituents such as the enzyme and/or polypeptide constituents. Non-limiting examples of enzyme performance include an indication of cellulose decay in lignocellulose hydrolysis. Non-limiting examples of suitable enzymes include enzymes selected from the group consisting of: a) wild-type exo-cellobiohydrolase, wild-type endo-1,4-β-glucanase, wild-type exo-1,4-β-glucosidase, wild-type cellobiase, or combinations thereof; b) a mutated exo-cellobiohydrolase, mutated endo-1,4-β-glucanase, mutated exo-1,4-β-glucosidase, mutated cellobiase, or combinations thereof; and c) a variant exo-cellobiohydrolase, variant endo-1,4-β-glucanase, variant exo-1,4-β-glucosidase, variant cellobiase, or combinations thereof. It is envisioned that peptide fragments and/or peptides of interest are suitable compositions of interest for analysis in accordance with the present disclosure.

In embodiments, the present disclosure provides a method of analyzing cellulose decay in biomass hydrolysis, including the steps of: hydrolyzing the biomass including cellulose in a reaction medium including an indicator constituent such as a fluorescent indicator compound, under conditions where the fluorescent indicator compound will bind to cellulose; and detecting a signal from the fluorescent indicator compound, wherein the intensity of the signal indicates a quality parameter of the enzyme of interest and/or polypeptide of interest in biomass hydrolysis. Such methods may be performed in a system.

In embodiments, the present disclosure provides a method of analyzing cellulose decay in biomass hydrolysis, including the steps of: (a) contacting biomass with a fluorescent indicator compound to form a mixture; (b) simultaneous to or subsequent to step (a) contacting the mixture with a reaction medium including enzyme and/or polypeptide of interest, (c) hydrolyzing the biomass including cellulose in a reaction medium under conditions where the fluorescent indicator compound will bind to cellulose; and (d) detecting a signal from the fluorescent indicator compound, wherein the intensity of the signal indicates a quality parameter of the enzyme and/or polypeptide of interest in biomass hydrolysis. Such methods may be performed in a system.

In embodiments, the present disclosure provides a method of determining whether an enzyme and/or polypeptide of interest affects cellulose hydrolysis, including the steps of: (a) contacting cellulosic material with a fluorescent indicator compound to form a mixture; (b) simultaneous to or subsequent to step (a) contacting the mixture with a reaction medium suitable for cellulose hydrolysis including enzyme and/or polypeptide of interest; (c) hydrolyzing the cellulosic material in a reaction medium under conditions where the fluorescent indicator compound will alter the cellulose and produce an optical signal indicative of the presence of cellulose; and (d) determining whether the hydrolyzed reaction has a desired optical signal, wherein the desired optical signal indicates cellulolytic activity of the enzyme of interest, and/or cellulolytic enhancing activity of the polypeptide of interest and/or the amount of cellulose hydrolyzed by the enzyme of interest and/or polypeptide of interest.

In embodiments, the present disclosure provides a method of analyzing cellulose decay in cellulosic material (e.g., lignocellulosic material such as corn stover) hydrolysis, including the steps of: (a) contacting cellulosic material (e.g., lignocellulosic material) with a fluorescent indicator compound to form a mixture; (b) simultaneous to or subsequent to step (a) contacting the mixture with a reaction medium including enzyme and/or polypeptide of interest; (c) hydrolyzing the cellulosic material containing cellulose in the reaction medium under conditions where the fluorescent indicator compound will bind to the cellulose; and (d) detecting a signal from the fluorescent indicator compound, wherein the intensity of the signal indicates the amount of cellulose hydrolyzed by the enzyme and/or polypeptide.

In embodiments, the present disclosure provides a system for evaluating enzyme performance including: at least one reaction area, wherein the reaction area for analyzing cellulose decay in cellulosic material (e.g., lignocellulosic material) hydrolysis, the reaction area including: at least one well for: (a) contacting cellulosic material with an indicator constituent such as a fluorescent indicator compound to form a mixture; (b) simultaneous to or subsequent to step (a) contacting the mixture with a reaction medium including enzyme and/or polypeptide of interest; (c) hydrolyzing the cellulosic material containing cellulose in the reaction medium under conditions where the indicator constituent such as a fluorescent indicator compound will stain the cellulose; and at least one detector suitable for detecting a signal from the fluorescent indicator compound, wherein the intensity of the signal indicates the amount of cellulose hydrolyzed by the reaction medium including any enzyme of interest and/or polypeptide of interest. In one system embodiment the detector is located below the reaction medium and below the plate the reaction medium is within.

In embodiments, the present disclosure provides a system for evaluating enzyme performance including: at least one reaction area, wherein the reaction area for analyzing cellulose decay in cellulosic material (e.g., lignocellulose) hydrolysis, the reaction area including: at least one well for: hydrolyzing the cellulosic material containing cellulose in the reaction medium including indicator constituent under conditions where the indicator constituent such as a fluorescent indicator compound will stain the cellulose; and at least one detector suitable for detecting a signal from the fluorescent indicator compound, wherein the intensity of the signal indicates the amount of cellulose hydrolyzed by the reaction medium including any enzyme of interest and/or polypeptide of interest. In embodiments, the steps of (a) contacting cellulosic material with an indicator constituent such as fluorescent indicator compound to form a mixture; and (b) simultaneous to or subsequent to step (a) contacting the mixture with a reaction medium including enzyme of interest, occur prior to the hydrolysis. However, it is contemplated that, in embodiments, indicator constituent may be added after the hydrolysis is complete.

Indicator Constituent

In embodiments, methods in accordance with the present disclosure add one or more indicator constituents to a cellulose hydrolysis in an effective amount to bind or stain cellulose in the hydrolysis reaction medium. The reaction medium may including one or more enzymes and/or polypeptides, mixtures of enzymes, mixtures of polypeptides and/or mixtures of enzymes and polypeptides of interest to be analyzed. In embodiments, methods in accordance with the present disclosure add one or more indicator constituents to a cellulose hydrolysis in an effective amount to indicate a quality parameter of one or more enzyme(s) and/or polypeptides of interest. Optimally, only cellulose is highlighted in the reaction medium with no other reaction medium constituents highlighted by the indicator compound. However, in embodiments, mostly cellulose is highlighted in the reaction medium with small amounts of other constituents also highlighted by the indicator constituent. Background highlighting of constituents of the reaction mixture other than cellulose is meant to be avoided, however small amounts of background highlighting of constituents other than cellulose will not make the methods of the present disclosure inaccurate.

Non-limiting examples of suitable indicator constituents in accordance with the present disclosure include stilbene derivatives, styryl derivatives of benzene and biphenyl, pyrazolines, bis(benzoxazol-2-yl) derivatives, coumarins, carbostyrils, or mixtures thereof. These indicator constituents may be added directly to the hydrolysis, or by initially contacting cellulosic material such as lignocellulosic material with an indicator constituent to form a mixture. The mixture may be then contacted with a reaction medium including the enzyme(s) and/or polypeptide(s) or interest. Hydrolysis is performed in the presence of the indicator constituent such as, for example, hydrolyzing the cellulosic material or lignocellulosic material containing cellulose in the reaction medium under conditions where the indicator constituent will stain or bind to the cellulose. Using the indicator constituents in accordance with the present disclosure, a signal from residual cellulose may be at least 2 times, at least 3 times, at least 4 times, at least 5 times, at least 6 times, at least 7 times, at least 8 times, at least 9 times, at least 10 times, at least 20 times, at least 30 times, at least 40 times, at least 50 times, at least 100 times, at least 1000 times, or at least 10,000 times higher or more intense than signal from residual cellulose not contacted with the indicator constituent in accordance with the present disclosure. Further, indication of residual cellulose may be at least 2 times, at least 3 times, at least 4 times, at least 5 times, at least 6 times, at least 7 times, at least 8 times, at least 9 times, at least 10 times, at least 20 times, at least 30 times, at least 40 times, at least 50 times, at least 100 times, at least 1000 times, or at least 10,000 times better or improved over a hydrolysis reaction not contacted with the indicator constituent in accordance with the present disclosure. For example, the indication may be improved in that the assay is performed in less time.

In embodiments, methods in accordance with the present disclosure add one or more indicator constituents to cellulose hydrolysis in an effective amount to indicate a quality parameter of one or more enzyme(s) and/or polypeptide(s) of interest in the hydrolysis. Thus, the methods of the present disclosure are suitable for an enzyme and/or polypeptide purchaser to check, for example, product stability and/or enzyme activity. Moreover, manufacturers can check product stability and activity for quality assurance purposes.

In embodiments, the methods in accordance with the present disclosure include the addition of one or more fluorescent indicator constituents in an amount sufficient to highlight the cellulose in accordance with the present disclosure. In embodiments, fluorescent indicator constituents are added in an amount sufficient to fluoresce and/or highlight cellulose in the reaction medium. Non-limiting examples of suitable fluorescent indicator constituents for use in accordance with the present disclosure include stilbene derivatives, styryl derivatives of benzene and biphenyl, pyrazolines, bis(benzoxazol-2-yl) derivatives, coumarins, carbostyrils, and mixtures thereof. Many chemical structures of these compounds are shown and described in *Fluorescent Whitening Agents, Kirk-Othmer Encyclopedia of Chemical Technology* 1994 by Harold J. McElhone (herein incorporated by reference in its entirety).

Non-limiting examples of suitable stilbene derivatives include bistriazinyl derivatives of 4,4'-diaminostilbene-2,2'-disulfonic acid. Other stilbene derivatives include p-nitro toluene ortho-sulfonic acid, and 4,4'-dinitrostilibene-2,2'-disulfonic acid. In embodiments, diaminostilbenes are suitable for use as fluorescent indicator constituents for use in accordance with the present disclosure. Non-limiting examples of diaminostilbenes include 4,4'-bis[[4-anilino-6-bis[(2-hydroxyethyl)amino]-s-triazin-2-yl]amino]-2,2'-stilbenedisulfonic acid (Fluorescent brightener 28 or Calcofluor White M2R brand brightener available from SIGMA-ALDRICH®), and/or BLANKOPHOR® brand brighteners. 4,4'-bis[[4-anilino-6-bis[(2-hydroxyethyl)amino]-s-triazin-2-yl]amino]-2,2'-stilbenedisulfonic acid is available from SIGMA-ALDRICH®, and has a chemical structure shown below.

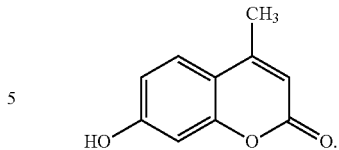

In embodiments, any compound capable highlighting or fluorescing cellulose to create a detectable signal may be suitable for use in accordance with the present disclosure. As used herein, indicator constituents are non-limiting and may also include optical brighteners, whitening agents. Non-limiting examples of additional indicator constituents include Uvitex 2B fluorescent dye from Polysciences Inc., Rylux BSU brand optical brightener, FITC-labeled WGA (wheat germ agglutinin FITC labeled) and/or ConA-lectins.

In embodiments, the indicator constituents do not alter the chemistry of the hydrolysis or make the hydrolysis more favorable. In embodiments, the indicator constituents do not highlight other constituents in the reaction medium. Thus, disruptive background highlighting is minimized or avoided.

In embodiments, 4,4'-bis[[4-anilino-6-bis[(2-hydroxyethyl)amino]-s-triazin-2-yl]amino]-2,2'-stilbenedisulfonic acid is suitable for use in accordance with the present disclosure. This chemical, also known as fluorescence brightener 28 (FB28) is a diaminostilbene compound, capable of binding to cellulose. Without being bound by the present disclosure it is believed that upon binding of fluorescent brightener 28 to cellulose the cellulosic hydroxyl groups are restricted in their vibration. Thus, the binding is mainly due to hydrogen bonds.

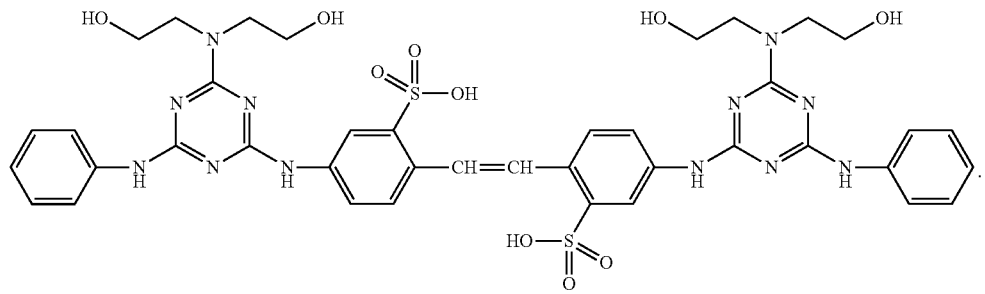 [SMILES: O=S(=O)(O)c1cc(Nc2nc(Nc3ccccc3)nc(N(CCO)CCO)n2)ccc1C=Cc1ccc(Nc2nc(Nc3ccccc3)nc(N(CCO)CCO)n2)cc1S(=O)(=O)O]
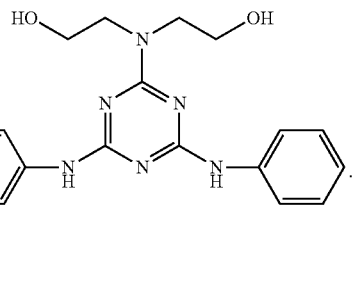

In embodiments, a suitable indicator constituent for use in accordance with the present disclosure is BLANKOPHOR® brand brightener available from Bayer and has the general chemical structure shown below.

However, the structure of the diaminostilbene brighteners may suggest that stacking between the p-electron systems of the aromatic rings and the stacked rings of the glucose units may also play a role in the binding.

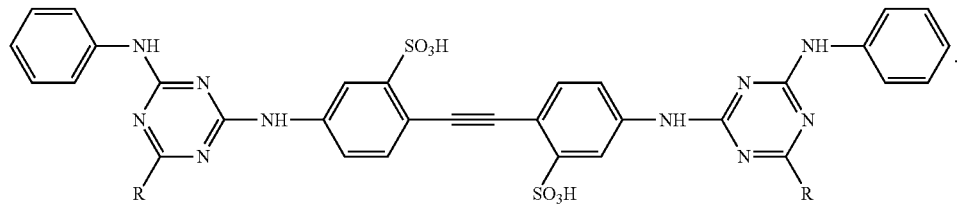

In embodiments, coumarins are suitable indicator constituents for use in accordance with the present disclosure. One non-limiting example of coumarin suitable for use in accordance with the present disclosure is 4-methylumbelliferone having the chemical formula shown below:

In embodiments, fluorescent brighteners suitable for use in washing detergents are suitable for use in accordance with the present disclosure. Without being bound by any theory, such brighteners may work due to absorption of light in the invisible UV range and its emission in the blue range. Binding to cellulose increases the quantum yield of the fluorescent brightener compared to unbound fluorescent brightener.

In embodiments, 4,4'-bis[[4-anilino-6-bis[(2-hydroxyethyl)amino]-s-triazin-2-yl]amino]-2,2'-stilbenedisulfonic acid is suitable for use in detecting cellulose, chitin, and mannans. It is believed that excellent binding of this chemical is specified for polysaccharides with β(1-3)- and β(1-4)-linked D-glucopyranosyl units.

In embodiments, other compound suitable for use as brighteners include Uvitex 2B, Rylux BSU, and FITC-labeled WGA- and ConA-lectins.

In embodiments, fluorescent dyes suitable for use as indicator constituents in accordance with the present disclosure include naphthalimide dyes, coumarin dyes, xanthenes dyes, thioxanthene dyes, naphtholactam dyes, azlactone dyes, methane dyes, oxazine and thiazine dyes, and combinations thereof. The dyes are added in an amount sufficient to highlight residual cellulose after a hydrolysis reaction. The dyes should not be added in amounts that create excessive background highlighting of other constituents of the reaction medium.

In embodiments, the indicator constituents of the present disclosure are suitable for creating a signal. The signal may be electromagnetic radiation such as light rays on the electromagnetic spectrum. For example, the signal may be characterized as having a wavelength in the UV, Vis, or NIR portion of the electromagnetic spectrum. In embodiments, the signal is characterized as luminescent, or any process in which energy is emitted from a material at a different wavelength from that at which it is absorbed. In embodiments, the signal is characterized as fluorescent or having fluorescence. Fluorescent signal incorporates a phenomenon in which electron de-excitation occurs almost spontaneously, and in which emission from a luminescent substance ceases when an exciting source is removed. Thus, it is envisioned that embodiments herein include a step of exciting the indicator constituent. For example, electromagnetic radiation may be applied to the indicator constituent so that it may emit energy or a signal such as at a predetermined intensity.

In embodiments, the signal is such that it can be detected by a microplate reader. A microplate reader is a laboratory instrument designed to detect biological, chemical, or physical events of samples in one or more microtiter plates. Sample reactions can be assayed in, inter alia, 6-1536 well format microtiter plates. Typically, a high-intensity lamp passes light to the microtiter well and the light emitted by the reaction happening in the microplate well is quantified by a detector. Common detection modes for microplate assays are absorbance, fluorescence intensity, luminescence, time-resolved fluorescence, and fluorescence polarization.

Substrate

The substrate suitable for use in accordance with the present disclosure is any material subjected to a hydrolysis reaction in a reaction medium in accordance with the present disclosure. Substrates suitable for use in accordance with the present disclosure contain cellulose. Non-limiting examples of substrate suitable for use in accordance with the present disclosure include biomass, cellulosic material, lignocellulose or lignocellulosic material, pre-treated lignocellulosic material, grassy substrates, high pectin plant, corn stover, pre-treated corn stover or PCS, or combinations of these materials.

Cellulose is generally found, for example, in the stems, leaves, hulls, husks, and cobs of plants or leaves, branches, and wood of trees. Non-limiting examples of cellulosic material include herbaceous material, agricultural residues, forestry residues, municipal solid wastes, waste paper, and/or pulp and paper mill residues, and combinations thereof. It is understood herein that the cellulose may be in the form of lignocellulose, a plant cell wall material containing lignin, cellulose, and hemicellulose in a mixed matrix. Other non-limiting examples of cellulosic material include corn stover, corn fiber, rice straw, paper and pulp processing waste, woody or herbaceous plants or bagasse. Other non-limiting examples of cellulosic material include cellulosic material subjected to pretreatment, using conventional methods known in the art. For example, physical pretreatment techniques can include various types of milling, irradiation, steaming/steam explosion, and hydrothermolysis; chemical pretreatment techniques can include dilute acid, alkaline, organic solvent, ammonia, sulfur dioxide, carbon dioxide, and pH-controlled hydrothermolysis; and biological pretreatment techniques can involve applying lignin-solubilizing microorganisms (see, for example, Hsu, T. A., 1996, *Pretreatment of biomass*, in *Handbook on Bioethanol: Production and Utilization*, Wyman, C. E., ed., Taylor & Francis, Washington, D.C., 179-212; Ghosh, P., and Singh, A., 1993, *Physicochemical and biological treatments for enzymatic/microbial conversion of lignocellulosic biomass*, Adv. Appl. Microbiol. 39: 295-333; McMillan, J. D., 1994, *Pretreating lignocellulosic biomass: a review*, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, *Ethanol production from renewable resources*, in Advances in Biochemical Engineering/Biotechnology, Scheper, T., ed., Springer-Verlag Berlin Heidelberg, Germany, 65: 207-241; Olsson, L., and Hahn-Hagerdal, B., 1996, *Fermentation of lignocellulosic hydrolysates for ethanol production*, Enz. Microb. Tech. 18: 312-331; and Vallander and Eriksson, 1990, *Production of ethanol from lignocellulosic materials*: State of the art, Adv. Biochem. Eng./Biotechnol. 42: 63-95).

In embodiments, one suitable substrate is pre-treated corn stover or "PCS". PCS refers to a cellulosic material derived from corn stover that has been subjected to one or more pretreatment step(s). Non-limiting examples of PCS is cellulosic material derived from corn stover and contacted with heat and dilute acid. In embodiments of the present disclosure, PCS may be made by the method described in Example 9 of U.S. Pat. No. 7,271,244 (herein incorporated by reference in its entirety), or variations thereof in time, temperature and amount of acid. The examples and figures also refer to PCS-A, PCS-B, and PCS-C. Here, the A, B and C are simply added to indicate that each specified PCS refers to a cellulosic material derived from corn stover that is subjected to a different pre-treatment.

As used herein the term "biomass" refers to renewable organic matter. Non-limiting examples of biomass include agricultural crops and residue, wood and wood waste, animal waste, aquatic plants and organic components of municipal and industrial wastes. Non-limiting examples of plant biomass may refer to a grassy substrate, a high cellulose substrate, a woody plant substrate, a high pectin substrate, and/or mixtures or combinations thereof.

As used herein, "grassy substrates" refer to plant biomass substrates that are grasses. Non-limiting examples of grassy substrates include, timothy grass, bermudagrass, napier grass, sorghum, and/or switchgrass, and mixtures and/or combinations thereof. Other non-limiting examples of grassy substrates include one or members of *Sorghum* spp. (e.g., *Sorghum bicolor*), *Miscanthus* spp. (e.g., *Miscanthus sinesis*), *Saccharum* spp. (e.g., *Saccharum ravennae*), *Zea* spp. (e.g., *Zea mays*), *Panicum* spp. (e.g., *Panicum virgatum*),

*Cynodon* spp. (e.g., *Cynodon dactylon, Cynodon transvaalensis, Cynodon magennissii,* etc.), *Phleum* spp. (e.g., *Phleum pratense*), or *Pennisetum* spp (e.g., *Pennisetum purpureum*). Non-limiting examples of grassy substrates also include hybrid grasses such as, for example, *Miscanthus giganteus* or hybrids of *Miscanthus* spp. and *Saccharum* spp. (e.g., miscane and/or energycane). Non-limiting examples of high cellulose substrates include plant material that include at least 50% cellulose such as, for example, cotton (*Gossypium* spp.) and wood pulp from, for example, pine (*Pinus* spp.) or poplar (*Populus* spp.). Non-limiting examples of high pectin plant biomass substrates include plant material that Includes at least 0.5% pectin such as, for example, apples, apricots, citrus, sugar beets, and other fruits and vegetables.

In embodiments, lignocellulose is a suitable substrate for use in accordance with the present disclosure. The structure of lignocellulose is not initially directly accessible to enzymatic hydrolysis. Therefore, in embodiments, lignocellulose-containing material is pre-treated, e.g., by acid hydrolysis under adequate conditions of pressure and temperature, in order to break the lignin seal and disrupt the crystalline structure of cellulose. Pre-treatment may result in solubilization of the hemicellulose and cellulose fractions. The cellulose and hemicelluloses can then be hydrolyzed enzymatically, e.g., by cellulolytic and/or hemicellulolytic enzymes or one or more enzymes of interest in accordance with the present disclosure. It may be desirable to convert the carbohydrate polymers into fermentable sugars which may be fermented into fermentation products, for example, ethanol. Optionally the fermentation product may be recovered, e.g., by distillation as also described above. The lignocellulose-containing material may according to the present disclosure be pre-treated using methods known in the art. In embodiments the pre-treated material is hydrolyzed, for example enzymatically, in accordance with the present disclosure. The goal of pre-treatment is to separate and/or release cellulose, hemicellulose and/or lignin and this way improve the rate of enzymatic hydrolysis.

According to the present disclosure pre-treatment may be a conventional pre-treatment step known in the art. Pre-treatment may take place in aqueous slurry. The lignocellulose-containing material may during pre-treatment be present in an amount between 10-80 wt. %, for example between 20-50 wt. %.

In embodiments, the lignocellulose-containing material may be chemically, mechanically and/or biologically pre-treated before hydrolysis. Mechanical treatment (often referred to as physical pre-treatment) may be used alone or in combination with subsequent or simultaneous hydrolysis, especially enzymatic hydrolysis, to promote the separation and/or release of cellulose, hemicellulose, and/or lignin.

In embodiments, the chemical, mechanical, and/or biological pre-treatment is carried out prior to the hydrolysis. Alternatively, the chemical, mechanical, and/or biological pre-treatment is carried out simultaneously with hydrolysis, such as simultaneously with addition of one or more cellulolytic enzymes, other enzyme activities mentioned below, and/or one or more enzymes of interest to release fermentable sugars, such as glucose and/or cellobiose.

In embodiments of the present disclosure, the pre-treated lignocellulose-containing material is washed and/or detoxified before or after hydrolysis step. This may improve the fermentability of, e.g., dilute-acid hydrolyzed lignocellulose-containing material, such as corn stover. Detoxification may be carried out in any suitable way, e.g., by steam stripping, evaporation, ion exchange, resin or charcoal treatment of the liquid fraction, or by washing the pre-treated material.

According to the present disclosure "chemical pre-treatment" refers to any chemical treatment which promotes the separation and/or release of cellulose, hemicelluloses, and/or lignin. Non-limiting examples of suitable chemical pre-treatment steps include treatment with; for example, dilute acid, lime, alkaline, organic solvent, ammonia, sulphur dioxide, carbon dioxide. Further, wet oxidation and pH-controlled hydrothermolysis are also contemplated chemical pre-treatments.

In embodiments, the chemical pre-treatment is acid treatment, for example, a continuous dilute and/or mild acid treatment, such as, treatment with sulfuric acid, or another organic acid, such as acetic acid, citric acid, tartaric acid, succinic acid, or mixtures thereof. Other acids may also be used. Mild acid treatment means in the context of the present disclosure that the treatment pH lies in the range from 1-5, for example from pH 1-3. In a specific embodiment the acid concentration is in the range from 0.1 to 2.0 wt % acid, for example sulphuric acid. The acid may be mixed or contacted with the material to be fermented according to the present disclosure and the mixture may be held at a temperature in the range of 160-220° C., for example 165-195° C., for periods ranging from minutes to seconds, e.g., 1-60 minutes, for example 2-30 minutes or 3-12 minutes. Addition of strong acids, such as sulphuric acid, may be applied to remove hemicellulose. This enhances the digestibility of cellulose.

Cellulose solvent treatment, also contemplated according to the present disclosure, has been shown to convert about 90% of cellulose to glucose. It has also been shown that enzymatic hydrolysis could be greatly enhanced when the lignocellulosic structure is disrupted. Alkaline $H_2O_2$, ozone, organosolv (uses Lewis acids, $FeCl_3$, $(Al)_2SO_4$ in aqueous alcohols), glycerol, dioxane, phenol, or ethylene glycol are among solvents known to disrupt cellulose structure and promote hydrolysis (Mosier et al. *Bioresource Technology* 96 (2005), p. 673-686).

Alkaline chemical pre-treatment with base, e.g., NaOH, $Na_2CO_3$, and/or ammonia, or the like, is also within the scope of the present disclosure. Pre-treatment methods using ammonia are described in, e.g., WO 2006/110891, WO 2006/11899, WO 2006/11900, WO 2006/110901, which are hereby incorporated by reference in their entirety.

Wet oxidation techniques involve use of oxidizing agents, such as: sulphite based oxidizing agents or the like. Non-limiting examples of solvent pre-treatments include treatment with DMSO (dimethyl sulfoxide) or the like. Chemical pre-treatment is generally carried out for 1 to 60 minutes, such as from 5 to 30 minutes, but may be carried out for shorter or longer periods of time depending on the material to be pre-treated.

Other non-limiting examples of suitable pre-treatment methods are described by Schell et al., 2003, *Appl. Biochem and Biotechn.* 105-108: 69-85, and Mosier et al., 2005, *Bioresource Technology* 96: 673-686, and US publication no. 2002/0164730, which references are hereby all incorporated by reference in their entirety.

As used in context of the present disclosure the term "mechanical pre-treatment" refers to any mechanical or physical pre-treatment that promotes the separation and/or release of cellulose, hemicelluloses, and/or lignin from lignocellulose-containing material. Non-limiting examples of mechanical pre-treatment include various types of milling, irradiation, steaming/steam explosion, and hydrothermolysis.

Mechanical pre-treatment includes comminution (mechanical reduction of the particle size). Comminution includes dry milling, wet milling, and vibratory ball milling.

Mechanical pre-treatment may involve high pressure and/or high temperature (steam explosion). In an embodiment of the present disclosure high pressure means pressure in the amount of 300 to 600 psi, for example 400 to 500 psi, or for example around 450 psi. In an embodiment of the present disclosure high temperature means temperatures in the range of from about 100 to 300° C., for example from about 140 to 235° C. In embodiments, mechanical pre-treatment is a batch-process, steam gun hydrolyzer system which uses high pressure and high temperature as defined above. A Sunds Hydrolyzer (available from Sunds Defibrator AB, Sweden) may be used for this.

In embodiments of the present disclosure, both chemical and mechanical pre-treatments are carried out together involving, for example, both dilute or mild acid pretreatment and high temperature and pressure treatment. The chemical and mechanical pretreatment may be carried out sequentially or simultaneously, as desired.

Accordingly, in embodiments, the lignocellulose-containing material is subjected to both chemical and mechanical pre-treatment to promote the separation and/or release of cellulose, hemicelluloses, and/or lignin.

In embodiments the pre-treatment is carried out as a dilute and/or mild acid steam explosion step. In embodiments, pre-treatment is carried out as an ammonia fiber explosion step (or AFEX pretreatment step).

As used in the present disclosure the term "biological pre-treatment" refers to any biological pre-treatment which promotes the separation and/or release of cellulose, hemicellulose, and/or lignin from the lignocellulose-containing material. Biological pre-treatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh, P., and Singh, A., 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech.* 18: 312-331; and Vallander, L., and Eriksson, K.-E. L., 1990, Production of ethanol from lignocellulosic materials: State of the art, *Adv. Biochem. Eng./Biotechnol.* 42: 63-95).

In embodiments, biological pre-treatment involves applying lignin degrading enzymes to lignin or pretreated material. Non-limiting examples of suitable lignin degrading enzymes include one or more lignolytic enzymes, one or more oxidoreductases, and combinations thereof. Non-limiting examples of lignolytic enzymes include manganese peroxidase, lignin peroxidase, and cellobiose dehydrogenase, and combinations thereof. Non-limiting examples of suitable pretreatment enzymes also include one or more laccases, one or more cellobiose dehydrogenases, and combinations thereof.

In embodiments, lignin peroxidase such as "ligninase", EC number 1.14.99, is suitable for use in accordance with the present disclosure.

In one embodiment, Ethazyme™ Pre available from Zymetis is suitable for use in pretreatment in accordance with the present disclosure.

In embodiments, pre-treated corn stover is suitable for use as a substrate in accordance with the present disclosure. Non-limiting examples of PCS is cellulosic material derived from corn stover and contacted with heat and dilute acid. In embodiments of the present disclosure, PCS may be made by the method described in Example 9 of U.S. Pat. No. 7,271,244 (herein incorporated by reference in its entirety), or variations thereof in time, temperature, and amount of acid.

Hydrolysis

In embodiments, methods in accordance with the present disclosure hydrolyze the cellulosic material in a reaction medium under conditions where the indicator constituent will bind to and/or stain the cellulose. Enzymatic hydrolysis may be carried out in a suitable aqueous environment under conditions described herein. In embodiments, hydrolysis is carried out at suitable, or optimal, conditions for the enzyme(s) and/or polypeptides of interest in question. Suitable process time, temperature, and pH conditions are described herein. In embodiments, hydrolysis is carried Out at a temperature between 25° C. and 70° C., for example between 40° C. and 60° C., or, in embodiments around 50° C. In embodiments, the step of hydrolysis is performed at 10° C. to 90° C. In embodiments, the hydrolysis step may be carried out at a pH in the range from 3-8, for example pH 4-8 or 4-6.

Hydrolysis may typically be carried out for between 1 and 150 hours, for example 60 to 80 hours, or in embodiments between 1 and 5 hours. For example, using a 96 well plate, at least 96 enzymes of interest may be subjected to hydrolysis for 72 hours.

In embodiments, the reaction medium has a volume in the amount of 10-1000 μl. However, the volume of the reaction medium can be adjusted by one of skill in the art. Non-limiting volumes of the reaction medium suitable for use in accordance with the present disclosure include volumes within 5-10,000 μl, or in embodiments 10-5000 μl, or in embodiments 20-2500 μl, or in embodiments 50-1500 μl, or in embodiments 100-900 μl, or in embodiments, 100-500 μl, or in embodiments 100-300 μl, or in embodiments 10-200 μl or in embodiments about 100 μl, 150 μl, 200 μl, 300 μl, 400 μl, 500 μl, 600 μl, or 700 μl. In embodiments, the reaction medium has a volume in the amount of 10-1000 μl. In embodiments, the reaction medium has a volume in the amount of 100-500 μl. In embodiments, the reaction medium has a volume in the amount of 250-300 μl.

In embodiments, the reaction medium is disposed within a multi-well plate including at least two wells. For example, multi-well plates including 12, 24, 96, 384, 1,536, or 3,456 wells are suitable for use in accordance with the present disclosure. Suitable plates include plates made of polypropylene. In embodiments, the wells are sealed, for example, the reaction medium may be disposed in at least two sealed wells.

In embodiments, one or more enzymes of interest are added to the reaction medium in an amount sufficient to hydrolyze 20% to 100% of the substrate. For example, if the substrate is lignocellulosic material, one or more enzymes of interest are added to the reaction medium in an amount sufficient to hydrolyze 20% to 100% of the lignocellulosic material. In embodiments, enzyme of interest is added in an amount sufficient to hydrolyze the lignocellulosic material. In embodiments, one or more polypeptides of interest are added to the reaction medium in an amount sufficient to hydrolyze 20% to 100% of the substrate.

In embodiments, one or more enzymes and/or polypeptides of interest are added to one or more wells or reaction mediums in an amount of 0.1 ng to 10 g. In embodiments, one or more enzymes of interest and/or polypeptide(s) are added to each well in an amount of 0.005 g to 10 g. In embodiments, one or more enzymes and/or polypeptide(s) of interest are added to each well or reaction in an amount of 0.1 ng to 10 mg. In embodiments, one or more enzymes and/or polypeptide(s) of interest are added to each well or reaction in an amount of 0.1 µg to 300 µg. Other non-limiting examples include amounts of one or more enzymes and/or polypeptide(s) of interest sufficient to hydrolyze 30% to 100% of the substrate, 40% to 100% of the substrate, 50% to 100% of the substrate, 60% to 100% of the substrate, 70% to 100% of the substrate, 80% to 100% of the substrate, 90% to 100% of the substrate, or about 91%, about 92%, about 93%, about 94%, about 95%, about 96%, about 97%, about 98%, about 99% of the substrate.

In embodiments, the reaction medium includes a buffer system. For example a 5 mM citric/citrate buffer is suitable for use in accordance with the present disclosure. In embodiments, 0.5 M sodium acetate at pH 5.0 with 10 mM manganese sulfate is suitable for use in the hydrolysis reaction. It is contemplated that the buffer stock may be used to dilute the hydrolysis reaction 1-30 fold, including 10-fold.

In embodiments, the reaction medium includes 0-500 mM of salt. In embodiments, the reaction medium includes 10-500 mM of salt or 50-300 mM of salt. One non-limiting example of salt suitable for use in accordance with the present disclosure is NaCl.

In embodiments, the reaction medium includes one or more surfactants. In embodiments, the surfactant is a nonionic surfactant, commercially available TWEEN® 80 brand surfactant (ICI Specialties) or any of the other TWEEN® 60 brand series products which are POE sorbitan derivatives. Other non-limiting suitable nonionic surfactants include D1600 brand surfactant from High Point Chemical Corp.; D1600 brand surfactant is an alkoxylated fatty acid. Furthermore, aryl alkyl polyetheralcohol, e.g., Union Carbide's TRITON® brand surfactant X-100 series of surfactants; alkyl phenyl ether of polyethylene glycol, e.g., Union Carbide's Tergitol brand surfactant series of surfactants; alkylphenol-ethylene oxide condensation products, e.g., Rhone Poulenc, Incorporated's Igepal brand surfactant series of surfactants. In embodiments an anionic surfactant may be used. Non-limiting examples of suitable anionic surfactants for use in accordance with the present disclosure are: ammonium or sodium salts of a sulfated ethoxylate derived from a 12 to 14 carbon linear primary alcohol; such as Vista's Alfonic brand surfactant 1412A or 1412S; and sulfonated naphthalene formaldehyde condensates, e.g., Rohm and Haas's Tamol brand surfactant SN. In embodiments, a cationic surfactant can be used. Suitable cationic surfactants include imidazole compounds, e.g., Ciba-Geigy's Amasoft brand surfactant 16-7 and Sapamine brand surfactant, P quaternary ammonium compounds; Quaker Chemicals' Quaker brand surfactant. 2001; and American Cyanamid's Cyanatex brand surfactant.

In embodiments, the reaction medium has about 0.5% to 10% total solids. In embodiments, the reaction medium includes 0.5% to 10% total solids. In embodiments, the reaction medium includes 1% to 9% total solids. In embodiments, the reaction medium includes 2% to 8% total solids. In embodiments, the reaction medium includes 3% to 7% total solids. In embodiments, the reaction medium includes 4% to 6% total solids. In embodiments, the reaction medium includes 1%, 2%, 3%, 4%, 5%, 6%, 7%, 8%, 9%, or 10% total solids. In embodiments, PCS is added in these amounts.

In embodiments, hydrolysis is carried out enzymatically using one or more enzymes of interest or mixtures of enzymes of interest.

In embodiments, hydrolysis is carried out enzymatically using one or more polypeptides of interest or mixtures of polypeptides of interest.

In embodiments, hydrolysis is carried out enzymatically using one or more enzymes and one or more polypeptides of interest or mixtures of enzymes and polypeptides of interest.

The effects of buffer, ionic strength, temperature, inhibitors, and surfactant addition are described below in Example 3. In embodiments, citrate and acetate buffer are acceptable for use in accordance with the present disclosure; the pH working range is from 5 to 6; an acceptable temperature for the methods of the present disclosure is 50° C. It has been found that the methods in accordance with the present disclosure are not affected by the addition of up to 200 mM NaCl. Further, inhibitors such as ethanol do not interfere with the methods in accordance with the present disclosure.

In embodiments, the methods in accordance with the present disclosure can be used with citrate, acetate, and BIS/TRIS buffer in the pH range of 5 to 6. In embodiments, pH 7 is workable, for example when the complete hydrolysis reaction was done.

In embodiments, the methods in accordance with the present disclosure work very well at temperatures from 50 to 60° C.

In embodiments, the total solids or "TS" of the reaction medium is in the amount of 1-5%, for example 3% or 4% TS PCS. In embodiments, PCS contains cellulose in the amount of 0.4-0.7 g cellulose per g PCS. For example PCS may contain 0.55 g cellulose per g PCS. In embodiments, for example when using an enzyme composition such as *Trichoderma reesei* cellulolytic protein composition (*Trichoderma reesei* strain RutC30 broth including GH61 polypeptide having cellulolytic enhancing activity and *Aspergillus oryzae* beta-glucosidase fusion protein) obtained according to WO 2008/151079, 0.01-200 mg EP of enzyme composition/g cellulose may be included in the hydrolysis reaction, for example 4 mg/g cellulose. In embodiments, the reaction volume is 10-1000 µL, for example 250 µL.

In embodiments, the reaction medium is a liquid, for example a substantially aqueous liquid such as water.

Enzymes and Polypeptides of Interest

It is to be understood that the methods in accordance with the present disclosure relate to analyzing, screening and/or evaluating enzyme(s) alone or in combination with polypeptides of interest and enzyme/polypeptide mixtures of interest. It is contemplated that these methods are suitable for application to one or more known enzymes or known enzyme mixtures, unknown enzymes or unknown enzyme mixtures or combinations of known and unknown enzymes or enzyme mixtures of interest. It is further contemplated that the methods of the present disclosure are suitable for application to enzyme or enzyme mixtures including one or more enzymes which are novel, or have not yet been discovered at the time of filing the present disclosure. It is also contemplated that the methods in accordance with the present invention are suitable for application to known enzymes; however such known enzymes may have unknown characteristics, for example, unknown cellulolytic activity.

It is contemplated that these methods are suitable for application to one or more known polypeptides or known polypeptide mixtures, unknown polypeptides or unknown polypeptides mixtures or combinations of known and unknown polypeptides or polypeptide mixtures of interest. It is further contemplated that the methods of the present disclosure are suitable for application to polypeptides or polypeptides mixtures including one or more polypeptides which are novel, or have not yet been discovered at the time of filing the present disclosure. It is also contemplated that the methods in accordance with the present invention are suitable for application to known polypeptides; however such known polypeptides may have unknown characteristics, for example, unknown cellulolytic enhancing activity.

Even if not specifically mentioned in context of a method or process of the present disclosure, it is to be understood that enzyme(s) of interest and/or polypeptide(s) of interest is(are) used in an effective amount. For example, an effective amount of enzyme may refer to an amount of one or more enzyme(s) in accordance with the present disclosure sufficient to induce a particular positive benefit to processes in accordance with the present disclosure. The positive benefit can be activity-related, for example, activity towards a substrate. For example, the benefit may be cellulolytic hydrolysis.

As discussed above, hydrolysis is carried out enzymatically using one or more enzymes of interest or mixtures of enzymes of interest. It is contemplated that enzyme of interest includes variant enzymes, mutant enzymes, wild-type enzymes, hybrid enzymes, or fragments thereof having activity of the enzyme of interest.

It is also contemplated that the enzyme of interest is suitable for use in the hydrolysis of cellulose as the methods of the present disclosure relate to measuring cellulolytic activity of enzyme of interest. Accordingly, enzymes of interest include, but are not limited to, those enzymes that are likely beneficial to the hydrolysis of cellulose. Non-limiting examples of enzymes of interest include new and/or known cellulase variants derived from a parental cellulase by substitution, insertion, and/or deletion. A cellulase variant in accordance with the present disclosure may be a cellulase variant or mutated cellulase, having an amino acid sequence not found in nature. Suitable cellulase variants for use in the methods of the present disclosure thus may show improved performance, in particular with respect to increased cellulolytic enzyme activity. It is also contemplated that such cellulase variants have improved performance in catalytic activity; and/or altered sensitivity to anionic tensides; and/or altered pH optimum; and/or altered thermostability. In embodiments, cellulase variants or mutated cellulase suitable for use in methods in accordance with the present disclosure include those enzymes regarded as a functional derivative of a parental cellulase (i.e., the native or wild-type enzyme), and may be obtained by alteration of a DNA nucleotide sequence of the parental gene or its derivatives, encoding the parental enzyme. The cellulase variant or mutated cellulase may be expressed and produced when the DNA nucleotide sequence encoding the cellulase variant is inserted into a suitable vector in a suitable host organism. The host organism is not necessarily identical to the organism from which the parental gene originated.

It is also contemplated that the polypeptide of interest is suitable for use in the hydrolysis of cellulose as the methods of the present disclosure relate to measuring cellulolytic activity of polypeptide of interest. Non-limiting examples of polypeptides of interest include polypeptides falling into the glycoside hydrolase Families 3, 5, 6, 7, 10, 11, and 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696 (both of which are herein incorporated by reference in their entirety).

It is also contemplated that one or more enzymes or polypeptides of interest may be derived from a parent cell that was mutagenized by methods known in the art. For example, mutagenesis of the parent cell can be achieved by irradiation, e.g., UV, X-ray, or gamma radiation of the parent cell. Furthermore, mutagenesis can be obtained by treatment with chemical mutagens, e.g., nitrous acid, nitrosamines, methyl nitrosoguanidine, and base analogues such as 5-bromouracil. It is contemplated that the mutagen may be applied to spores of the parent strain, and the surviving spores are plated out for growth on a solid medium. It will also be understood that mutants can also be naturally occurring variants in a population in the absence of a specific mutagenesis procedure, either by selection, screening, or a combination of selection and screening. See, for example, Wiebe et al., 1992, *Mycological Research* 96: 555-562 and Wiebe et al., 1991, *Mycological Research* 95: 1284-1288 for isolating morphological mutants of *Fusarium* strain A3/5. Therefore, for purposes of the present disclosure, the term "mutants" also encompasses naturally occurring variants or mutants without deliberate application of mutagens, i.e., spontaneous mutants. It is further contemplated that the parent cell that was mutagenized may be a filamentous fungal parent cell. Non-limiting examples of filamentous fungi include all filamentous forms of the subdivision Eumycota and Oomycota (as defined by Hawksworth et al., In, *Ainsworth and Bisby's Dictionary of The Fungi*, 8th edition, 1995, CAB International, University Press, Cambridge, UK). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic.

Non-limiting enzymes of interest include one or more wild-type, mutant, or variant hydrolases (class E.C. 3 according to Enzyme Nomenclature), for example one or more wild-type, mutant or variant carbohydrases including cellulolytic enzymes and hemicellulolytic enzymes, or hybrids or fragments and combinations thereof. Further, protease, alpha-amylase, glucoamylase and/or the like may also be present during hydrolysis and thus be considered enzymes of interest.

In embodiments, the enzyme preparation contains one or more of the following activities: a cellulase, a hemicellulase, an expansin, an esterase, a ligninolytic enzyme, a pectinase, a peroxidase, a protease, a swollenin, and a xyloseisomerase. In embodiments, the cellulase is preferably one or more (several) enzymes selected from the group consisting of an endoglucanase, a cellobiohydrolase, and a beta-glucosidase. In embodiments, the hemicellulase is preferably one or more (several) enzymes selected from the group consisting of an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In embodiments, non-limiting examples of suitable enzymes of interest include one or more enzymes selected from the group consisting of: (a) wild-type exo-cellobiohydrolase, wild-type endo-1,4-β-glucanase, wild-type exo-1,4-β-glucosidase, wild-type cellobiase, or combinations thereof; (b) mutated exo-cellobiohydrolase, mutated endo-1,4-β-glucanase, mutated exo-1,4-β-glucosidase, mutated cellobiase, or combinations thereof; and (c) variant exo-cellobiohydrolase, variant endo-1,4-β-glucanase, variant exo-1,4-β-glucosidase, variant cellobiase, or combinations thereof. These enzymes may be present alone or in combination with other enzymes of interest in enzyme cocktails. It is also contemplated that enzyme of interest include hybrid enzymes such as hybrids of the aforementioned enzyme of interest. It is also contemplated that enzyme of interest include fragments of the aforementioned enzyme(s) of interest, including fragments having an activity such as the activity of the enzyme of interest. For example, the fragment of a cellulase of interest would have cellulase activity, and the fragment of an amylase of interest would have amylase activity.

Enzymes and/or polypeptides having cellulolytic activity of interest

It is contemplated that enzymes of interest include one or more enzymes under the classification (EC 3.2.1.91), as well as cellobiohydrolase I and cellobiohydrolase II, endo-glucanase activity (EC 3.2.1.4) and beta-glucosidase activity (EC 3.2.1.21).

At least three categories of enzymes are important for converting cellulose into fermentable sugars: endo-glucanases (EC 3.2.1.4) that cut the cellulose chains at random; cellobiohydrolases (EC 3.2.1.91) which cleave cellobiosyl units from the cellulose chain ends, and beta-glucosidases (EC 3.2.1.21) that convert cellobiose and soluble cellodextrins into glucose. Among these three categories of enzymes involved in the biodegradation of cellulose, cellobiohydrolases seem to be the key enzymes for degrading native crystalline cellulose.

The cellulolytic activity may, in embodiments, be in the form of a preparation of enzymes of fungal origin, such as from a strain of the genus *Trichoderma*, or a strain of *Trichoderma reesei*; a strain of the genus *Humicola*, such as a strain of *Humicola insolens*; or a strain of *Chrysosporium*, or a strain of *Chrysosporium lucknowense* (see e.g., U.S. Application Publication No. 2007/0238155 from Dyadic Inc, USA).

In embodiments, the enzyme preparation is a composition concerned in co-pending application U.S. Application Ser. No. 60/941,251, which is hereby incorporated by reference in its entirety. In embodiments, the enzyme preparation comprises a polypeptide having cellulolytic enhancing activity, for example a GH61 polypeptide having cellulolytic enhancing activity, or one of the GH61 polypeptides disclosed in WO 2005/074656, WO 2008/148131, WO 2005/074656, WO 2010/065830, WO 2007/089290 WO 2009/085935, WO 2009/085859, WO 2009/085864, and WO 2009/085868 (Novozymes). The enzyme preparation may further comprise a beta-glucosidase, such as a beta-glucosidase derived from a strain of the genus *Trichoderma, Aspergillus* or *Penicillium*, including the fusion protein having beta-glucosidase activity disclosed in co-pending U.S. Application Ser. No. 60/832,511 (PCT/US2007/074038) (Novozymes). In embodiments, the enzyme preparation may also include a CBH II enzyme, for example *Thielavia terrestris* cellobiohydrolase II (CEL6A). In embodiments the enzyme preparation may also include cellulolytic enzymes, for example, those derived from *Trichoderma reesei, Humicola insolens*, and/or *Chrysosporium lucknowense*.

In embodiments, the enzyme preparation may also comprise a GH61 polypeptide having cellulolytic enhancing activity disclosed in WO 2005/074656; a beta-glucosidase (fusion protein disclosed in U.S. 60/832,511 or PCT/US2007/074038) and cellulolytic enzymes derived from *Trichoderma reesei*.

In embodiments, the enzyme preparation may include a GH61 polypeptide having cellulolytic enhancing activity disclosed in WO 2005/074656; a beta-glucosidase (fusion protein disclosed in U.S. 60/832,511 or PCT/US2007/074038); a CBH II enzyme from *Thielavia terrestris* (CEL6A; and cellulolytic enzymes derived from *Trichoderma reesei*.

In embodiments, the enzyme preparation is the commercially available product such as CELLIC™ Ctec (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.).

The cellulolytic activity may be dosed in the amount of from 0.1-100 FPU per gram total solids (TS), or in embodiments 0.5-50 FPU per gram TS, or 1-20 FPU per gram TS.

Endoglucanase (EG) of Interest

Endoglucanase is suitable enzyme of interest for use in accordance with the present disclosure. Non-limiting examples of endoglucanases include those derived from a strain of the genus *Trichoderma*, for example a strain of *Trichoderma reesei*; a strain of the genus *Humicola*, such as a strain of *Humicola insolens*; or a strain of *Chrysosporium*, for example a strain of *Chrysosporium lucknowense*.

Cellobiohydrolase (CBH) of Interest

Cellobiohydrolase enzymes are suitable enzymes of interest in accordance with the present disclosure. As used herein the term "cellobiohydrolase" means a 1,4-beta-D-glucan cellobiohydrolase (E.C. 3.2.1.91). Such enzymes are able to catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain.

Non-limiting examples of cellobiohydrolases are mentioned above including CBH I and CBH II from *Trichoderma reesei; Humicola insolens*; and CBH II from *Thielavia terrestris* cellobiohydrolase (CELL6A).

Cellobiohydrolase activity may be determined according to the procedures described by Lever et al., 1972, *Anal. Biochem.* 47: 273-279 and by van Tilbeurgh et al., 1982, *FEBS Letters* 149: 152-156; van Tilbeurgh and Claeyssens, 1985, *FEBS Letters* 187: 283-288. The Lever et al. method is suitable for assessing hydrolysis of cellulose in corn stover and the method of van Tilbeurgh et al. is suitable for determining the cellobiohydrolase activity on a fluorescent disaccharide derivative, 4-methylumbelliferyl-β-D-lactoside.

Beta-Glucosidase of Interest

Beta-glucosidase enzymes are suitable as enzymes of interest in accordance with the present disclosure especially during hydrolysis. As used herein term "beta-glucosidase" refers to a beta-D-glucoside glucohydrolase (E.C. 3.2.1.21). Such enzymes are typically suited to catalyze the hydrolysis of terminal non-reducing beta-D-glucose residues with the release of beta-D-glucose. For purposes of the present disclosure, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 μmole of p-nitrophenol produced per minute at 50° C., pH 5 from 4 mM p-nitrophenyl-beta-D-glucopyranoside as substrate in 100 mM sodium citrate, 0.01% TWEEN® 20.

In embodiments, beta-glucosidase in accordance with the present disclosure is of fungal origin, for example a strain of the genus *Trichoderma, Aspergillus* or *Penicillium*. Non-limiting examples of beta-glucosidase includes those derived from *Trichoderma reesei*, such as the beta-glucosidase encoded by the bgl1 gene (see FIG. 1 of EP 562003), or beta-glucosidase derived from *Aspergillus oryzae* (recombinantly produced in *Aspergillus oryzae* according to WO 02/095014), *Aspergillus fumigatus* (recombinantly produced in *Aspergillus oryzae* according to Example 22 of WO 02/095014; WO 2005/047499), *Aspergillus niger* (Dan et al., 2000, *J. Biol. Chem.* 275: 4973-4980), *Aspergillus aculeatus* (Kawaguchi et al., 1996, *Gene* 173: 287-288), or *Penicillium brasilianum* (WO 2007/019442).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Polypeptide Having Cellulolytic Enhancing Activity of Interest

The polypeptides having cellulolytic enhancing activity enhance the hydrolysis of a lignocellulose derived material catalyzed by proteins having cellulolytic activity by reducing the amount of cellulolytic enzyme required to reach the same degree of hydrolysis by at least 1.01-fold, or at least 1.05-fold, or at least 1.10-fold, or at least 1.25-fold, or at least 1.5-fold, or at least 2-fold, or at least 3-fold, or at least 4-fold, or at least 5-fold, or at least 10-fold, or at least 20-fold.

In embodiments the hydrolysis and/or fermentation is carried out in the presence of a cellulolytic enzyme in combination with a polypeptide having enhancing activity. In embodiments, the polypeptide having enhancing activity is a Family GH61 polypeptide. WO 2005/074647 and WO 2008/148131 disclose isolated polypeptides having cellulolytic enhancing activity and the polynucleotides thereof from *Thielavia terrestris*. WO 2005/074656 and WO 2010/065830 disclose isolated polypeptides having cellulolytic enhancing activity and the polynucleotides thereof from *Thermoascus aurantiacus*. WO 2007/089290 discloses an isolated polypeptide having cellulolytic enhancing activity and the polynucleotide thereof from *Trichoderma reesei*. WO 2009/085935, WO 2009/085859, WO 2009/085864, and WO 2009/085868 disclose isolated polypeptides having cellulolytic enhancing activity and the polynucleotides thereof from *Myceliophthora thermophila*. WO 2008/151043 discloses methods of increasing the activity of a polypeptide having cellulolytic enhancing activity by adding a soluble activating divalent metal cation to a composition comprising the polypeptide having cellulolytic enhancing activity.

Hemicellulolytic Enzymes of Interest

Hemicellulolytic enzymes are suitable enzymes of interest in accordance with the present disclosure. For example, the pre-treated lignocellulose-containing material may further be subjected to one or more hemicellulolytic enzymes, e.g., one or more hemicellulases.

Hemicellulose can be broken down by hemicellulases and/or acid hydrolysis to release its five and six carbon sugar components.

In an embodiment of the present disclosure the lignocellulose derived material may be treated with one or more hemicellulases.

Any hemicellulase suitable for use in hydrolyzing hemicellulose, for example into xylose, may be used. Non-limiting examples of hemicellulases include xylanases, arabinofuranosidases, acetyl xylan esterase, feruloyl esterase, glucuronidases, endo-galactanase, mannases, endo or exo arabinases, exo-galactanses, and mixtures of two or more thereof. In embodiments, the hemicellulase for use in the present disclosure is an exo-acting hemicellulase. In embodiments, the hemicellulase is an exo-acting hemicellulase which has the ability to hydrolyze hemicellulose under acidic conditions of below pH 7, or in embodiments pH 3-7. A non-limiting example of hemicellulase suitable for use in the present disclosure includes VISCOZYME™ (available from Novozymes A/S, Denmark).

In an embodiment the hemicellulase is a xylanase. In an embodiment the xylanase may be of microbial origin, such as of fungal origin (e.g., *Trichoderma, Meripilus, Humicola, Aspergillus, Fusarium*) or from a bacterium (e.g., *Bacillus*). In embodiments the xylanase is derived from a filamentous fungus, for example derived from a strain of *Aspergillus*, such as *Aspergillus aculeatus* (GeneSeqP:AAR63790; WO 94/21785) or *Aspergillus fumigatus* (WO 2006/078256); a strain of *Thielavia*, for example, *Thielavia terrestris* (WO 2009/079210); or a strain of *Humicola*, for example *Humicola lanuginosa*. The xylanase may be an endo-1,4-beta-xylanase, or an endo-1,4-beta-xylanase of GH10 or GH11.

Non-limiting examples of commercial xylanases include SHEARZYME™ (Novozymes A/S), CELLIC™ Htec (Novozymes A/S), BIOFEED WHEAT (Novozymes A/S), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

In an embodiment the hemicellulase is a beta-xylosidase. In embodiments the beta-xylosidase is derived from *Trichoderma reesei* beta-xylosidase (UniProtKB/TrEMBL accession number Q92458), *Talaromyces emersonii* (SwissProt accession number Q8X212), and *Neurospora crassa* (SwissProt accession number Q7SOW4).

In an embodiment the hemicellulase is an acetylxylan esterase. In embodiments the acetylxylan esterase is derived from *Hypocrea jecorina* (WO 2005/001036), *Neurospora crassa* (UniProt accession number q7s259), *Thielavia terrestris* NRRL 8126 (WO 2009/042846), *Chaetomium globosum* (Uniprot accession number Q2GWX4), *Chaetomium gracile* (GeneSeqP accession number AAB82124), *Phaeosphaeria nodorum* (Uniprot accession number Q0UHJ1), and *Humicola insolens* (WO 2009/073709).

In an embodiment the hemicellulase is a ferulic acid esterase. In embodiments the ferulic acid esterase is derived from *Humicola insolens* (WO 2009/076122), *Neurospora crassa* (UniProt accession number Q9HGR3), and *Neosartorya fischeri* (UniProt Accession number A1D9T4).

In an embodiment the hemicellulase is an arabinofuranosidase. In embodiments the arabinofuranosidase is derived from *Humicola insolens* (WO 2009/073383) and *Aspergillus niger* (GeneSeqP accession number AAR94170).

In an embodiment the hemicellulase is an alpha-glucuronidasee. In embodiments the alpha-glucuronidase is derived from *Aspergillus clavatus* (UniProt accession number alcc12), *Trichoderma reesei* (Uniprot accession number Q99024), *Talaromyces emersonii* (UniProt accession number Q8X211), *Aspergillus niger* (Uniprot accession number Q96WX9), *Aspergillus terreus* (SwissProt accession number Q0CJP9), and *Aspergillus fumigatus* (SwissProt accession number Q4WW45).

In embodiments, hemicellulase is added in an amount effective to hydrolyze hemicellulose, for example, in amounts from about 0.001 to 0.5 wt.-% of total solids (TS), or in embodiments in an amount of from about 0.05 to 0.5 wt.-% of TS.

Xylanases may be added in amounts of 0.001-1.0 g/kg DM or dry matter) substrate, or in the amounts of 0.005-0.5 g/kg DM substrate, or in embodiments from 0.05-0.10 g/kg DM substrate.

Additional non-limiting examples of enzymes of interest that may be used in the hydrolysis include wild-type, mutants, or variants of the enzymes below:

Alpha-Amylase of Interest

In accordance with the present disclosure any alpha-amylase may be used as an enzyme of interest, such as of fungal, bacterial or plant origin. For example the alpha-amylase may be an acid alpha-amylase, e.g., acid fungal alpha-amylase or acid bacterial alpha-amylase. The term "acid alpha-amylase" means an alpha-amylase (E.C. 3.2.1.1) which added in an effective amount has activity optimum at a pH in the range of 3 to 7, or in embodiments from 3.5 to 6, or in embodiments from 4-5.

Bacterial Alpha-Amylase of Interest

In embodiments, suitable bacterial alpha-amylase for use in accordance with the present disclosure as enzyme of interest includes those derived from the genus Bacillus.

In embodiments, the Bacillus alpha-amylase is derived from a strain of Bacillus licheniformis, Bacillus amyloliquefaciens, Bacillus subtilis or Bacillus stearothermophilus, but may also be derived from other Bacillus sp. Non-limiting examples of contemplated alpha-amylases include the Bacillus licheniformis alpha-amylase shown in SEQ ID NO: 1, the Bacillus amyloliquefaciens alpha-amylase SEQ ID NO: 2 and the Bacillus stearothermophilus alpha-amylase shown in SEQ ID NO: 3. In embodiments, the alpha-amylase may be an enzyme having a degree of identity of at least 60%, or at least 70%, or at least 80%, or at least 90%, or at least 95%, or at least 96%, or at least 97%, or at least 98% or at least 99% to any of the sequences shown in SEQ ID NOS: 1, 2 or 3.

The Bacillus alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference in their entirety). Specifically contemplated alpha-amylase variants are disclosed in U.S. Pat. Nos. 6,093,562, 6,297, 038 or U.S. Pat. No. 6,187,576 (hereby incorporated by reference in their entirety) and include Bacillus stearothermophilus alpha-amylase (BSG alpha-amylase) variants having a deletion of one or two amino acid in positions R179 to G182, or a double deletion disclosed in WO 1996/023873—see e.g., page 20, lines 1-10 (hereby incorporated by reference in its entirety), for example corresponding to delta (181-182) compared to the wild-type BSG alpha-amylase amino acid sequence set forth in SEQ ID NO:3 or deletion of amino acids R179 and G180 using SEQ ID NO:3 for numbering (WO 99/19467 which is hereby incorporated by reference in its entirety). Other non-limiting examples include Bacillus alpha-amylases, for example, Bacillus stearothermophilus alpha-amylase, which have a double deletion corresponding to delta (181-182) and further includes a N193F substitution (also denoted I181*+G182*+N193F) compared to the wild-type BSG alpha-amylase amino acid sequence set forth in SEQ ID NO:3.

Bacterial Hybrid Alpha-Amylase of Interest

Bacterial hybrid alpha-amylase are suitable for use in accordance with the present disclosure as enzymes of interest. For example, a hybrid alpha-amylase specifically contemplated comprises 445 C-terminal amino acid residues of the Bacillus licheniformis alpha-amylase (shown in SEQ ID NO: 1) and the 37 N-terminal amino acid residues of the alpha-amylase derived from Bacillus amyloliquefaciens (shown in SEQ ID NO: 2), with one or more, especially all, of the following substitutions:

G48A+T49I+G107A+H156Y+A181T+N190F+I201F+A209V+Q264S (using the Bacillus licheniformis numbering in SEQ ID NO: 1). Other non-limiting examples include variants having one or more of the following mutations (or corresponding mutations in other Bacillus alpha-amylase backbones): H154Y, A181T, N190F, A209V, and Q264S and/or deletion of two residues between positions 176 and 179, preferably deletion of E178 and G179 (using SEQ ID NO: 2 for numbering).

In an embodiment the bacterial alpha-amylase is dosed in an amount of 0.0005-5 KNU per g DS, or 0.001-1 KNU per g DS, or in embodiments around 0.050 KNU per g DS.

Fungal Alpha-Amylase of Interest

Fungal alpha-amylases are suitable for use as enzymes in accordance with the present disclosure. Non-limiting examples include alpha-amylases derived from a strain of the genus Aspergillus, such as, Aspergillus oryzae, Aspergillus niger, and Aspergillus kawachii alpha-amylases.

In embodiments, acidic fungal alpha-amylase includes a FUNGAMYL®-like alpha-amylase which is derived from a strain of Aspergillus oryzae. According to the present disclosure, the term "FUNGAMYL®-like alpha-amylase" indicates an alpha-amylase which exhibits a high identity, e.g., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 4.

Another non-limiting example of an acid alpha-amylase derived from a strain Aspergillus niger. In embodiments the acid fungal alpha-amylase is the one from Aspergillus niger disclosed as "AMYA_ASPNG" in the Swiss-prot/TeEMBL database under the primary accession no. P56271 and described in WO 89/01969 (See Example 3 therein—hereby incorporated by reference in its entirety). In embodiments, a commercially available acid fungal alpha-amylase derived from Aspergillus niger is SP288 (available from Novozymes A/S, Denmark) is suitable for use in accordance with the present disclosure as enzyme of interest.

Other non-limiting examples include contemplated wild-type alpha-amylases include those derived from a strain of the genera Rhizomucor and Meripilus, or a strain of Rhizomucor pusillus (See WO 2004/055178 incorporated by reference in its entirety) or Meripilus giganteus.

In embodiments the alpha-amylase is derived from Aspergillus kawachii and disclosed by Kaneko et al., 1996, J. Ferment. Bioeng. 81: 292-298, "Molecular-cloning and determination of the nucleotide-sequence of a gene encoding an acid-stable alpha-amylase from Aspergillus kawachii"; and further as EMBL: #AB008370.

In embodiments, the fungal alpha-amylase may also be a wild-type enzyme including a starch-binding domain (SBD) and an alpha-amylase catalytic domain (e.g., none-hybrid), or a variant thereof. In embodiments the wild-type alpha-amylase is derived from a strain of Aspergillus kawachii.

Fungal Hybrid Alpha-Amylase of Interest

Fungal hybrid alpha-amylase enzymes are suitable for use in accordance with the present disclosure. In embodiments, the fungal acid alpha-amylase is a hybrid alpha-amylase. Non-limiting examples of fungal hybrid alpha-amylases for use in accordance with the present disclosure include the hybrid alpha-amylases disclosed in WO 2005/003311 or U.S. Application Publication No. 2005/0054071 (Novozymes) or U.S. Application Ser. No. 60/638,614 (Novozymes) which is hereby incorporated by reference in its entirety. A hybrid alpha-amylase may include an alpha-amylase catalytic domain (CD) and a carbohydrate-binding domain/module (CBM), such as a starch binding domain, and optional a linker.

Non-limiting examples of contemplated hybrid alpha-amylases include those disclosed in Table 1 to 5 of the examples in U.S. Application Ser. No. 60/638,614, including FUNGAMYL® variant with catalytic domain JA118 and *Athelia rolfsii* SBD (SEQ ID NO: 5), *Rhizomucor pusillus* alpha-amylase with *Athelia rolfsii* AMG linker and SBD (SEQ ID NO: 6), *Rhizomucor pusillus* alpha-amylase with *Aspergillus niger* glucoamylase linker and SBD (which is a combination of amino acid sequences SEQ ID NO: 7, SEQ ID NO: 8, and SEQ ID NO: 9) or as V039 in Table 5 in WO 2006/069290, and *Meripilus giganteus* alpha-amylase with *Athelia rolfsii* glucoamylase linker and SBD (SEQ ID NO: 10). Other non-limiting examples of hybrid alpha-amylases are any of those listed in Tables 3, 4, 5, and 6 in Example 4 in U.S. application Ser. No. 11/316,535 and WO 2006/069290 (hereby incorporated by reference in their entirety).

Other non-limiting examples of contemplated hybrid alpha-amylases include those disclosed in U.S. Application Publication No. 2005/0054071, including those disclosed in Table 3 on page 15, such as *Aspergillus niger* alpha-amylase with *Aspergillus kawachii* linker and starch binding domain.

In embodiments, alpha-amylases include those which exhibit a high identity to any of above mention alpha-amylases, e.g., at least 70%, at least 75%, at least 80%, at least 85%, at least 90%, at least 95%, at least 96%, at least 97%, at least 98%, at least 99% or even 100% identity to the mature enzyme sequences.

An acid alpha-amylases may according to the present disclosure be added in an amount of 0.001 to 10 AFAU/g DS, or in embodiments from 0.01 to 5 AFAU/g DS, or 0.3 to 2 AFAU/g DS or 0.001 to 1 FAU-F/g DS, or in embodiments 0.01 to 1 FAU-F/g DS.

Commercial Alpha-Amylase Products of Interest

Commercial alpha-amylase enzymes are suitable for use in accordance with the present disclosure. Non-limiting examples of commercial compositions including alpha-amylase include MYCOLASE™ from DSM (Gist Brocades), BAN™, TERMAMYL™ SC, FUNGAMYL™, LIQUOZYME™ X, LIQUOZYME™ SC and SAN™ SUPER, SAN™ EXTRA L (Novozymes A/S) and CLAR-ASE™ L-40,000, DEX-LO™, SPEZYME™ FRED, SPEZYME™ AA, and SPEZYME™ DELTA AA (Genencor Int.), FUELZYME™ (from Verenium Corp, USA), and the acid fungal alpha-amylase sold under the trade name SP288 (available from Novozymes A/S, Denmark).

Carbohydrate-Source Generating Enzyme of Interest

As used herein the term "carbohydrate-source generating enzyme" includes glucoamylase (being glucose generators), beta-amylase and maltogenic amylase (being maltose generators), and also pullulanase and alpha-glucosidase. A carbohydrate-source generating enzyme is capable of producing a carbohydrate that can be used as an energy-source by the fermenting organism(s) in question, for instance, when used in a process of the present disclosure for producing a fermentation product, for example, ethanol. The generated carbohydrate may be converted directly or indirectly to the desired fermentation product, for example, ethanol. According to the present disclosure a mixture of carbohydrate-source generating enzymes may be used. Especially contemplated blends are mixtures including at least a glucoamylase and an alpha-amylase, for example, an acid amylase, or an acid fungal alpha-amylase. The ratio between glucoamylase activity (AGU) and acid fungal alpha-amylase activity (FAU-F) (e.g., AGU per FAU-F) may in embodiments of the present disclosure be in an amount of 0.1 and 100 AGU/FAU-F, or in embodiments 2 and 50 AGU/FAU-F, such as in an amount of 10-40 AGU/FAU-F, especially when enzyme of interest is desired for ultimately doing one-step fermentation (Raw Starch Hydrolysis—RSH), e.g., when saccharification and fermentation are carried out simultaneously (e.g., without a liquefaction step).

In a conventional starch-to-ethanol process (e.g., including a liquefaction step (a)) the ratio may be as defined in EP 140,410-B1, especially when saccharification in step ii) and fermentation in step iii) are carried out simultaneously.

Glucoamylase of Interest

Glucoamylase enzymes are suitable for use in accordance with the present disclosure. Non-limiting examples include a glucoamylase derived from any suitable source, e.g., derived from a microorganism or a plant. Non-limiting examples of glucoamylases are of fungal or bacterial origin, selected from the group consisting of *Aspergillus* glucoamylases, in particular *Aspergillus niger* G1 or G2 glucoamylase (Boel et al., 1984, *EMBO J.* 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (*Agric. Biol. Chem.* 55: 941-949, 1991), or variants or fragments thereof. Other *Aspergillus* glucoamylase variants include variants with enhanced thermal stability: G137A and G139A (Chen et al., 1996) *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry*, 35: 8698-8704; and introduction of Pro residues in position A435 and S436 (Li et al., 1997, *Protein Eng.* 10" 1199-1204.

Other non-limiting examples of glucoamylases include *Athelia rolfsii* (previously denoted *Corticium rolfsii*) glucoamylase (see U.S. Pat. No. 4,727,026 and (Nagasaka, Y. et al., 1998, "Purification and properties of the raw-starch-degrading glucoamylases from *Corticium rolfsii, Appl. Microbiol. Biotechnol.* 50: 323-330), *Talaromyces* glucoamylases, in particular derived from *Talaromyces emersonfi* (WO 99/28448), *Talaromyces leycettanus* (U.S. Pat. No. Re. 32,153), *Talaromyces duponti, Talaromyces thermophilus* (U.S. Pat. No. 4,587,215).

Non-limiting examples of bacterial glucoamylases include glucoamylases from the genus *Clostridium*, in particular *C. thermoamylolyticum* (EP 135,138), and *C. thermohydrosulfuricum* (WO 86/01831), and *Trametes cingulata, Pachykytospora papyracea*; and *Leucopaxillus giganteus* all disclosed in WO 2006/069289; or *Peniophora rufomarginata* disclosed in PCT/US2007/066618; or a mixture thereof. Also hybrid glucoamylase may be suitable for use in accordance with the present disclosure. Non-limiting examples include the hybrid glucoamylases disclosed in WO 2005/045018 and the hybrid glucoamylase disclosed in Table 1 and 4 of Example 1 (which hybrids are hereby incorporated by reference in their entirety).

In embodiments, glucoamylases suitable for use in accordance with the present disclosure include those which exhibit a high identity to any of above mention glucoamylases, e.g., at least 70%, at least 75%, at least 80%, at least 85%, at least 90%, at least 95%, at least 96%, at least 97%, at least 98%, at least 99% or even 100% identity to the mature enzymes sequences mentioned above.

Non-limiting examples of commercially available compositions including glucoamylase include AMG 200L; AMG 300 L; SAN™ SUPER, SAN™ EXTRA L, SPIRIZYME™

PLUS, SPIRIZYME™ FUEL, SPIRIZYME™ B4U, SPIRIZYME ULTRA™, and AMG™ E (from Novozymes A/S); OPTIDEX™ 300, GC480™ and GC147™ (from Genencor Int., USA); AMIGASET™ and AMIGASE™ PLUS (from DSM); G-ZYME™ G900, G-ZYME™ and G990 ZR (from Genencor Int.).

In embodiments, glucoamylases may be added in an amount of 0.0001-20 AGU/g DS, or in embodiments 0.001-10 AGU/g DS, or 0.01-5 AGU/g DS, for example 0.1-2 AGU/g DS.

Beta-Amylase of Interest Beta-amylase enzymes are suitable for use in accordance with the present disclosure. A beta-amylase (E.C. 3.2.1.2) is the name traditionally given to exo-acting maltogenic amylases, which catalyze the hydrolysis of 1,4-alpha-glucosidic linkages in amylose, amylopectin, and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (W. M. Fogarty and C. T. Kelly, 1979, *Progress in Industrial Microbiology* 15: 112-115). These beta-amylases are characterized by having optimum temperatures in the range from 40° C. to 65° C. and optimum pH in the range from 4.5 to 7. Non-limiting examples of beta-amylase suitable for use in accordance with the present disclosure include the commercially available beta-amylase from barley called NOVOZYM™ WBA from Novozymes A/S, Denmark and SPEZYME™ BBA 1500 from Genencor Int., USA.

Maltogenic Amylase of Interest

Maltogenic amylase is an enzyme suitable for use in accordance with the present disclosure. A "maltogenic alpha-amylase" (glucan 1,4-alpha-maltohydrolase, E.C. 3.2.1.133) is able to hydrolyze amylose and amylopectin to maltose in the alpha-configuration. Non-limiting examples of maltogenic amylase includes those from *Bacillus stearothermophilus* strain NCIB 11837 which is commercially available from Novozymes A/S. Additional examples of maltogenic alpha-amylases include those described in U.S. Pat. Nos. 4,598,048, 4,604,355 and 6,162,628, which are hereby incorporated by reference in their entity.

In embodiments, maltogenic amylase may be added in an amount of 0.05-5 mg total protein/gram DS or in embodiments in an amount of 0.05-5 MANU/g DS.

Proteases of Interest

Protease enzymes are suitable as enzymes of interest in accordance with the present disclosure and may be included in enzyme mixtures of interest. The protease may be any protease. In embodiments the protease is an acid protease of microbial origin, for example, of fungal or bacterial origin. In embodiments, an acid fungal protease is suitable for use in accordance with the present disclosure, but also other proteases can be used.

Non-limiting examples of suitable proteases include microbial proteases, for example, fungal and bacterial proteases. In embodiments, proteases are acidic proteases, e.g., proteases characterized by the ability to hydrolyze proteins under acidic conditions below pH 7.

Non-limited examples of acid fungal proteases include fungal proteases derived from *Aspergillus, Mucor, Rhizopus, Candida, Coriolus, Endothia, Enthomophtra, Irpex, Penicillium, Sclerotium* and *Torulopsis*. Additional non-limiting examples include proteases derived from *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc.*

*Japan* 28: 66), *Aspergillus awamori* (Hayashida et al., 1977, *Agric. Biol. Chem.* 42: 927-933, *Aspergillus aculeatus* (WO 95/02044), or *Aspergillus oryzae*, such as the pepA protease; and acidic proteases from *Mucor pusillus* or *Mucor miehei*.

Additional non-limiting examples of proteases include neutral or alkaline proteases, for example a protease derived from a strain of *Bacillus*. A particular protease contemplated for the present disclosure is protease derived from *Bacillus amyloliquefaciens* and has the sequence obtainable at Swiss-prot as Accession No. P06832. Also contemplated are the proteases having at least 90% identity to amino acid sequence obtainable at Swiss-prot as Accession No. P06832 such as at least 92%, at least 95%, at least 96%, at least 97%, at least 98%, or particularly at least 99% identity.

Non-limiting examples of proteases also include the proteases having at least 90% identity to amino acid sequence disclosed as SEQ ID NO: 11 such as at 92%, at least 95%, at least 96%, at least 97%, at least 98%, or particularly at least 99% identity.

Non-limiting examples of proteases also include papain-like proteases such as proteases within E.C. 3.4.22.*(cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase), and EC 3.4.22.30 (caricain).

In embodiments the protease is a protease preparation derived from a strain of *Aspergillus*, for example *Aspergillus oryzae*. In another embodiment the protease is derived from a strain of *Rhizomucor*, for example *Rhizomucor mehei*. In another embodiment the protease is a protease preparation, for example, a mixture of a proteolytic preparation derived from a strain of *Aspergillus*, (e.g., *Aspergillus oryzae*) and a protease derived from a strain of *Rhizomucor*, for example *Rhizomucor mehei*.

Other suitable proteases include aspartic acid proteases, for example, those described in, *Hand-book of Proteolytic Enzymes*, Edited by A. J. Barrett, N. D. Rawlings and J. F. Woessner, Aca-demic Press, San Diego, 1998, Chapter 270). Non-limiting examples of aspartic acid protease include, e.g., those disclosed in R. M. Berka et al., 1990, *Gene* 96: 313); R. M. Berka et al., 1993, *Gene* 125: 195-198; and Gomi et al., 1993, *Biosci. Biotech. Biochem.* 57: 1095-1100, which are hereby incorporated by reference in their entirety.

Non-limiting examples of commercially available protease products include ALCALASE®, ESPERASE™, FLAVOURZYME™, PROMIX™, NEUTRASE®, RENNILASE®, NOVOZYM™ FM 2.0L, and NOVOZYM™ 50006 (available from Novozymes A/S, Denmark) and GC106™ and SPEZYME™ FAN from Genencor Int., Inc., USA. Additional enzymes include FERMGEN™ and GC 212 from Genencor.

In embodiments, protease may be present in an amount of 0.0001-1 mg enzyme protein per g DS, or in some embodiments an amount of 0.001 to 0.1 mg enzyme protein per g DS. Alternatively, the protease may be present in an amount of 0.0001 to 1 LAPU/g DS, or in embodiments in an amount of 0.001 to 0.1 LAPU/g DS and/or 0.0001 to 1 mAU-RH/g DS, or 0.001 to 0.1 mAU-RH/g DS.

Non-Limiting Commercial Enzymes of Interest

In embodiments, granular starch hydrolyzing enzymes are suitable for use as enzymes in accordance with the present disclosure. For example, alpha-amylase and/or glucoamylase may be blending for the processing of uncooked starch. Commercially available blends include STARGEN™ 001 and STARGEN™ 002 available from Genencor.

In embodiments, enzymes suitable for use in accordance with the present disclosure include enzymes for starch liquefaction such as SPEZYME® ALPHA, SPEZYME® FRED L, SPEZYME® HPA and SPEZYME® XTRA brand enzymes from Genencor.

In embodiments, enzymes suitable for use in accordance with the present disclosure include enzymes such as FERMENZYME® C and FERMENZYME® L-400 brand enzymes available from Genencor.

Other commercially available enzymes for use in accordance with the present disclosure include enzymes such as DISTILLASE® L-400, DISTILLASE® L-500, DISTILLASE® VHP, G-ZYME®480 ETHANOL, OPTIMASE TBG, OPTIMASH VR, OPTIMASH XL and OPTIMASH BG brand enzymes available from Genencor.

It is also contemplated that enzymes of interest and/or polypeptides of interest include enzymes and/or polypeptides related to any of the aforementioned enzymes or polypeptides of interest by family, as well as a degree of identity. For example enzymes and polypeptides of interest include any enzyme or polypeptide having 50%, 60%, 70%, 80%, 90%, 95%, 96%, 97%, 98%, or 99% amino acid sequence identity to any of the aforementioned enzymes or polypeptides.

It is specifically contemplated that the methods in accordance with the present disclosure evaluate enzymes and/or polypeptides of interest and combinations thereof which are unknown. Accordingly, the enzymes and polypeptides listed above are non-limiting examples of suitable enzymes and/or polypeptides of interest which may be used alone or in combination as enzymes of interest and/or polypeptides of interest in accordance with the present disclosure.

Detecting

After hydrolyzing the substrate in accordance with the present disclosure, a signal is detected from cellulose remaining in the reaction medium. In embodiments, a microplate reader can be used to detect a signal from the cellulose in the reaction medium. For example, one of skill in the art can use any detector suitable for detecting a signal in a fluorescence or luminescence based assay.

In embodiments, the SPECTRAmax GEMINI XS Microplate Spectrofluorometer from Molecular Devices is a microplate reader suitable for use in accordance with the present disclosure. This device is capable of detecting signal from either fluorescence or luminescence based assays. This device includes standard microplate reader features including temperature control and shaker. The sensitivity is suitable for obtaining precise and reproducible measurements even wherein enzyme of interest had low enzymatic activities. In embodiments, software suitable for running this device includes the SOFTmax PRO Software that is sold with the spectrofluorometer.

In embodiments, the Beckmann DTX microplate reader is suitable for use in detecting residual cellulose in accordance with the present disclosure. This device runs in various modes detecting fluorescence Intensity, Absorbance (Visible), Luminescence (Glow) Integrated Shaking; Excitation Filters: Abs 405 nm, 450 nm, 492 nm, 620 nm Fl. 360 nm 485 nm Emission Filters: Fl. 465 nm, 535 nm Multimode Detection Software. Accordingly, it is envisioned that embodiments of the present disclosure include a step of exciting a reaction medium such as contacting it or subjecting it to excitation.

In embodiments, a robot is used with one or more pipettes for handling the following:
  Reaction medium
  Substrate
  Indicator constituent
  Plate (with one or more wells)
  Plate cover
  Incubator
  Plate reader In embodiments, the step of detecting occurs from below the reaction medium.

In embodiments, a system is provided to incorporate methods of the present disclosure including a combination of laboratory modules that complete sample preparation, analysis, and evaluation to provide chemical information. In embodiments, a system is provided for performing the methods of the present disclosure. The system includes a number of modules having standardized communications and system interfaces, allowing interchange of data, status information, and material. It is contemplated that the modules may be either hardware or software entity designed to be remotely controlled by another machine. Modules are capable of carrying out their operations autonomously, independent of the environment.

Figure 1B:
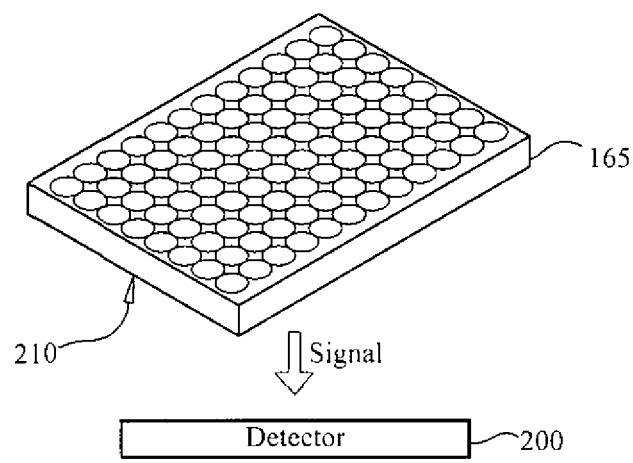
FIG. 1B is a diagram showing one embodiment of a plate reader module in the system of the present disclosure.

Referring now to FIG. 1A and FIG. 1B, a system in accordance with an embodiment of the present disclosure is shown. FIG. 1A shows system 100 operations and how a plurality of SLMs (130, 135, 140, 145) and SSMs (108 and 110) are employed to implement these operations. The system includes a plurality of standard modules including one or more standard laboratory modules (SLMs) and one or more standard support modules (SSMs). Standard laboratory modules are logical groupings of laboratory unit operations which perform a subtask of an analytical protocol. SLM also refers to hardware and/or software module which performs a complete subtask in an analytical protocol.

SSM 110 is a robotic articulated arm that provides transport modality or other means for moving objects within the system. SSM 110 can work alone or in combination with SSM 108 to manipulate specimens or supplies such as substrate, reaction medium, plates 165 (such as 96 well plate), plate cover(s) 160, one or more enzymes and/or polypeptides of interest, and indicator constituent from storage 120, preparing them, making them available to SLMs 130, 135, 140, 145, removing specimens and eliminating waste.

SLMs 130, 135, 140 and 145 have knowledge of the availability of the SSMs 108 and 110. For example, a SLM 130 "knows" whether there are enough supplies or other materials for it to function. This is because before the SLM can be directed by a task controller to perform a function, it first must ascertain whether it has enough materials to complete the task. For example, SLM 130, checks the SSM 108 tasked with providing the materials, and either proceed or report that it cannot do so and state a cause.

Both SLMs 130, 135, 140 and 145 and SSMs 108 and 110 have low-level controllers which drive components like actuators, detectors, and servomotors (not shown). The controllers also coordinate the internal electromechanical activities of the SLMs 130, 135, 140 and 145 and SSMs 108 and 110. Controllers also comprise software packages that provide a menu of programmable "configurations" and each one of these "configurations" corresponds to a customized task carried out by the module. For example, in liquid-dispensing SLMs, a configuration may supply fresh tubes (not shown), adding several aliquots of reagent to each, and capping them afterwards. In incubation modules, a configuration may specify the predetermined temperature and duration of the incubation. Programmable configurations are defined by certain physical parameters (volumes, times, temperatures, etc.) and well-designed controllers disallow situations that are operationally improper, such as overfilling tubes and centrifuging upside-down tubes. For enzyme research, certain high-level tools could program SLM controllers dynamically, enabling one instrument to perform any number of unique assays.

The SLMs 130, 135, 140 and 145 and SSMs 108 and 110 are communicatively coupled to one or more task sequence controllers 136. Task sequence controllers 136 are intermediate level devices which use tools from operations research to govern intricate flows of supplies and samples through automated instruments. Before performing actual tests, computer simulations mimic SSMs 108 and 110 controllers and adhere to critical timing events of the candidate tests procedures. This virtual instrument then generates start-up times and optimizes the sequence by which all tasks take place. Task sequence controller 136 users include laboratory technicians who load materials into automated instruments and supervise their performance on a daily basis and engineers who develop and debug new instruments or look for ways to improve on existing ones. Task sequence controller 136 is capable of dynamic retasking, which, for example allows adding and subtracting assays while automated instruments are up and running.

The task sequence controller 136 is communicatively coupled to a process controller 128. The system 100 includes an input and supply SSM 108. This module retrieves supply materials and reactants, such as well plates 165 to the system 100 SLMs. In one embodiment, the input and supply SSM can be realized with only minor modifications to an SSM incorporated in a robot. Similarly, inter-SLM transport SSM 110 passes samples among the different modules. In one embodiment, the intermodule transport SSM 110 comprises a robotic/articulated arm. These articulated arms travel along linear tracks, and have acceptable positioning tolerances, degrees of freedom and controller software for high precision manipulations.

Plate preparation SLM 130 combines fresh substrate, liquid reagents, and indicator constituent, then adds a plate cover 160 to plate 165. This module comprises single-tip pipette tools, tip disposal units, and integrated software for process control.

Incubation SLM 135 provides a temperature controlled environment for the sealed reaction plates 165. The temperature profile selected can be constant or varying as required. The incubation SLM 135 stores information regarding the incubation environment history, such as the time that each plate or set of plates spends under specified incubation conditions. Commercially available instruments, such as those available from Lab-Line Instruments can perform most of the functions required, but may require modification, for example, to add motorized doors for opening and closing the incubator on command.

Plate reader 145 SLM is provided for use in detecting residual cellulose in accordance with the present disclosure. In embodiments, this device runs in various modes detecting fluorescence Intensity. In embodiments, the device is modified or adjusted so that the detector is located below the reaction plate. For example, referring to FIG. 1B, a diagram of the detector 200 positioned below the reaction plate bottom 210 is shown.

Sample output and waste disposal SSM 145 disposes of waste materials including contaminated plates, pipette tips, reaction media, and other plastic ware and liquids.

Other system embodiments may be assembled accordingly to automated methods known in the art. Guidance for system assembly of embodiments may be obtained by referring to U.S. Pat. Nos. 5,968,731 and 5,366,896 (herein incorporated by reference in their entirety). See also, T. J. Beugelsdijk et al., *The standard laboratory module: an integrated approach to standardization in the analytical laboratory*, Lab. If. Manage. 21 (1993) (herein incorporated by reference in its entirety).

It is envisioned that standard analysis methods including sample preparation, analysis, and data interpretation are also suitable for use in practicing the methods of the present disclosure. One of ordinary skill in the art, may adopt the methods of in accordance with the present disclosure to various assay procedures and protocols.

The following non-limiting examples further illustrate methods in accordance with the present disclosure.

EXAMPLES

Materials and Methods

Indicator Constituents

Fluorescent brightener 28 (F3543, Sigma-Aldrich), 4-methylumbelliferone (M-1381, Sigma-Aldrich®), and BLANKOPHOR® brand brightener (B-1003, A.G. Scientific) were provided as indicator constituents. As buffer, a stock of 0.5 M sodium acetate at pH 5.0 with 10 mM manganese sulfate was diluted 10-fold in the hydrolysis reaction.

Analysis

For initial fluorescence spectra 10×FB28 stocks were prepared from a 2 mM stock solution in water and 20 μl of the stock were added to 80 μl of the carbohydrate, lignin or PCS solution. Fluorescence spectra without FB28 and absorption spectra were measured prior to FB28 addition.

PCS hydrolysis was done in 1 ml scale in AXYGEN® deep well plates. Hydrolysis was performed by combining the following: 1) 800 μl 6.25% dry weight biomass with pH adjusted to 5.0 by buffer addition; 2) 100 μl 500 mM acetate final mixture pH 5.0 including any additives such as metal, detergents, etc.; and 3) 100 μl enzyme mixture. Dosing of enzyme was in the amount of 01 to 50 mg/g cellulose. Values and volumes were suitable for a 1 g assay. The plate was sealed and inverted sharply to mix. Incubation was suitable at 50° C. for 3 days.

At 5% WGS-NREL PCS (also referred to herein simply as "PCS-A") 200 μM FB28 was used and at 3% 150 μM. In assays with 3% total solids in standard microtiter plates 240 μl of 3.75% WGS-NREL PCS, 30 μl of sodium acetate buffer, and 30 μl of the enzyme mix were mixed by pipetting 3 times up and down. The plates were sealed on an ALPS 3000 (165° C. for 1.5 seconds) and incubated at 50° C. for 72 hours with a manual inversion twice a day. Fluorescence was read at certain time points. At 72 hours the samples were filtered and analyzed by HPLC for glucose and cellobiose.

For statistical analysis the JMP package from SAS, Cary, N.C., USA was used.

Equipment

For top reading of fluorescence either Molecular Device GEMINI or a Beckmann DTX was used as a monochromator or filter based plate reader, respectively. Bottom reading was implemented in the Beckman DTX. For excitation a 360 nm filter with a 35 nm bandwidth and for emission a 465 nm filter with a 35 nm bandwidth were used. Absorbance spectra were read in a Molecular Device Spectramax. Prior to reading the spectra the plate was orbitally shaken for 20 seconds at highest speed.

For 96 well microtiter plates a polypropylene AXYGEN® 2 ml deep well plate, a polystyrene COSTAR® 9017 and a polypropylene 3364 μlate were used. These plates were sealed with an Abgene ALP3000 at 165° C. for 1.5 seconds for polystyrene and 160° C. for 7 seconds for polystyrene plates.

HPLC analysis of released glucose was used to assess the total amount of PCS pipetted into the well.

Substrates/Buffers

Washed ground sieved—NREL PCS from two different lots (KCMF1752-81 and -96), ground sieved NREL PCS and washed ground sieved PCS-C were used.

AVICEL® PH101 (11365, Fluka), xylan from birch wood (X0502, Sigma), Kelig 100 and VANISPERSE (lignin derivative) CB (Lignotech USA, Rothschild, Wis., USA) were diluted in purified water. Suspensions were thoroughly mixed before pipetting.

Enzymes

The following enzyme preparations were used:

1) a *Trichoderma reesei* cellulolytic protein composition (*Trichoderma reesei* strain RutC30 cellulase including GH61 polypeptide having cellulolytic enhancing activity and *Aspergillus oryzae* beta-glucosidase fusion protein) obtained according to WO 2008/151079 (also referred to herein as "CP1"). Enzyme was obtained from batch CZP0003 and CZP0001 of SaMe MF268; and 2) a mixture CELLUCLAST® 1.5L (Novozymes A/S, Bagsværd, Denmark) and 3% *Aspergillus oryzae* beta-glucosidase (recombinantly produced in *Aspergillus oryzae* according to WO 02/095014) (also referred to herein as "CP2"). The composition also included *Trichoderma reesei* strain RutC30 cellulase including GH61 polypeptide having cellulolytic enhancing activity.

Example 1

Spectroscopy of Fluorescent Brightener Mixed PCS Ingredients

Figure 2:
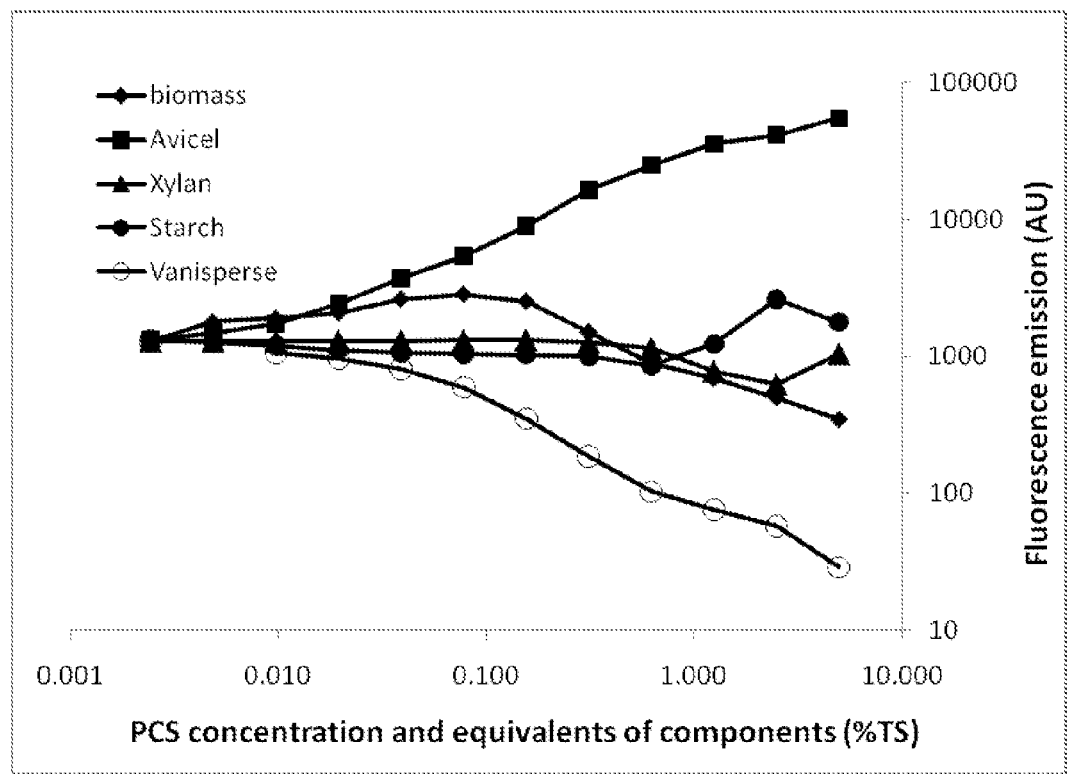
FIG. 2 is a pictorial view of a graph displaying fluorescence emission of various dilution series with 3.8 µM FB28 collected in a top read at 460 nm after excitation at 360 nm.

When FB 28 was added to beta 1-4 glucans the fluorescence intensity was reported to increase with beta 1-4 glucan concentration. Hence, a constant FB28 concentration was added to different amounts of WGS-NREL PCS (PCS-A), cellulose, lignin and other possible components of PCS. A prior UV-A irradiation decreased the background fluorescence significantly. Referring now to FIG. 2, fluorescence emission of dilution series with 3.8 mM FB28 collected in a top read at 460 nm after excitation at 360 nm is shown. Here, FB28 was added to a two-fold dilution series from 5 to 0.005% PCS-A. Similar dilutions series were tested starting from 26 g/l dispersed AVICEL® brand cellulose material, xylan, starch and 10 g/l of VANISPERSE brand lignin derivative. Prior to the fluorescence emission reading the plate was irradiated for 15 minutes with a UV-A lamp. FIG. 2 shows a cellulose dependent signal for insoluble AVICEL® cellulose fibers. Similar results were obtained with carboxymethylcellulose. Lignin absorbs or quenches the base emission of the FB28 fluorophore. Xylan and starch do not change the FB28 signal intensity considerably. For xylan this might be due to a strong substitution of the xylan core hindering the attachment of FB28. The PCS signal was a composition of the positive cellulose dependent and the negative lignin dependent signal.

Figure 3A:
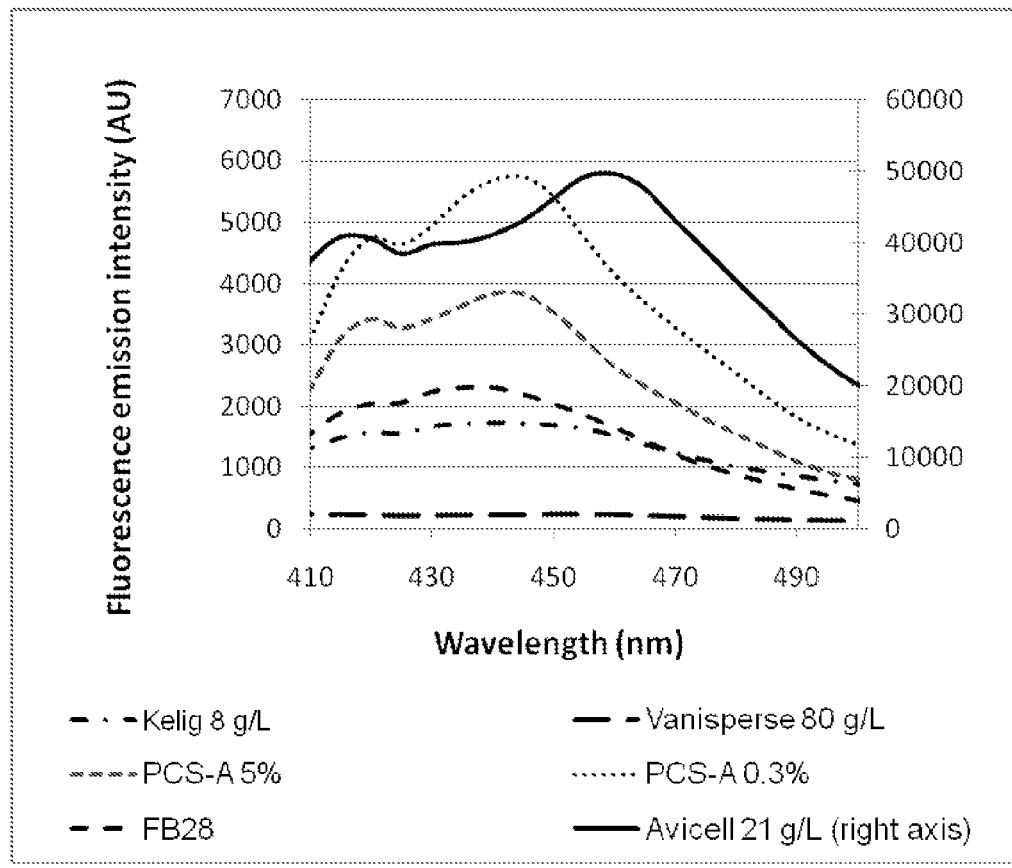
FIG. 3A is a pictorial view of a graph displaying fluorescence spectra measured at 360 nm excitation in UV transmissible microtiter plates with a volume of 80 µl.
Figure 3B:
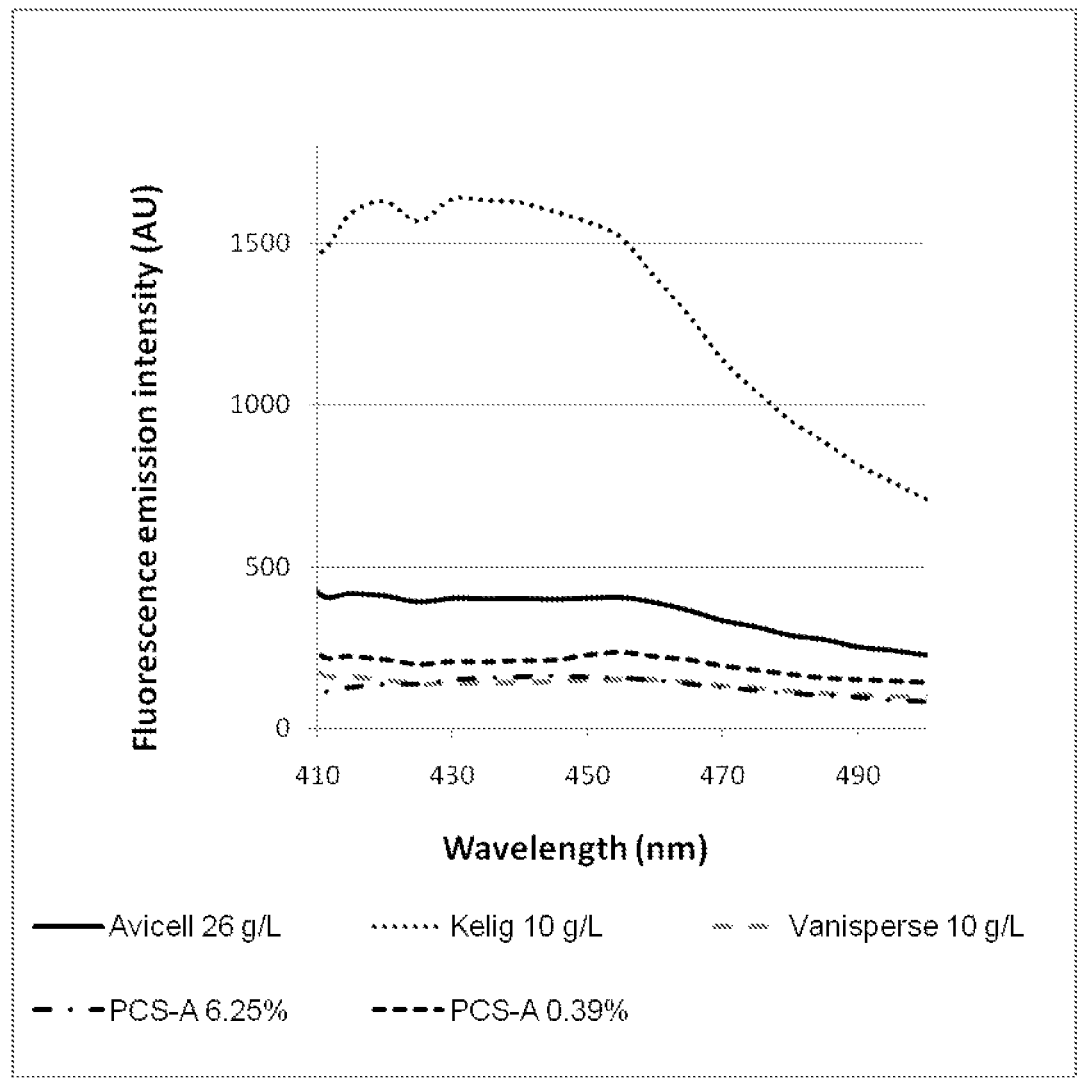
FIG. 3B is a pictorial view of a graph displaying fluorescence spectra measured at 360 nm excitation in UV transmissible microtiter plates with a volume of 100 µl with 8 µM fluorescent brightener 28.

Referring now to FIG. 3A, fluorescence spectra were measured at 360 nm excitation in UV transmissible microtiter plates with a volume of 80 µl per well without fluorescent brightener 28. It was observed that cellulose actually had a weak concentration dependent autofluorescence with a maximum 410 to 460 nm. Referring now to FIG. 3B, fluorescence spectra were measured at 360 nm excitation in UV transmissible microtiter plates with a volume of 100 µl per well with 3.8 µM fluorescent brightener 28. Cellulose fluorescence increased strongly after FB28 binding accompanied by a red shift of the emission maximum of 30 nm. This shift was less pronounced when FB28 bound to PCS. Although also about 21 g/l cellulose were present in 5% PCS-A the signal was only 1.7 fold increased compared to 22 fold for pure AVICEL® cellulose. Due to the lignin in the sample an inverse relationship between PCS concentration and the signal intensity was observed—with a decrease in PCS concentration the signal increased. Representing lignaceous residues commercial lignin fractions were tested. Kelig (lignosulfonate) showed strong autofluorescence with an emission maximum of 440 nm and a similar emission intensity to the signal from 3.8 µM FB28. When FB28 was added to the lignin fractions a decrease in the FB28 was observed. It was very strong for the non autofluorescent lignin VANISPERSE brand lignin derivative. Kelig mainly showed the same autofluorescence as without FB28 addition.

Figure 3C:
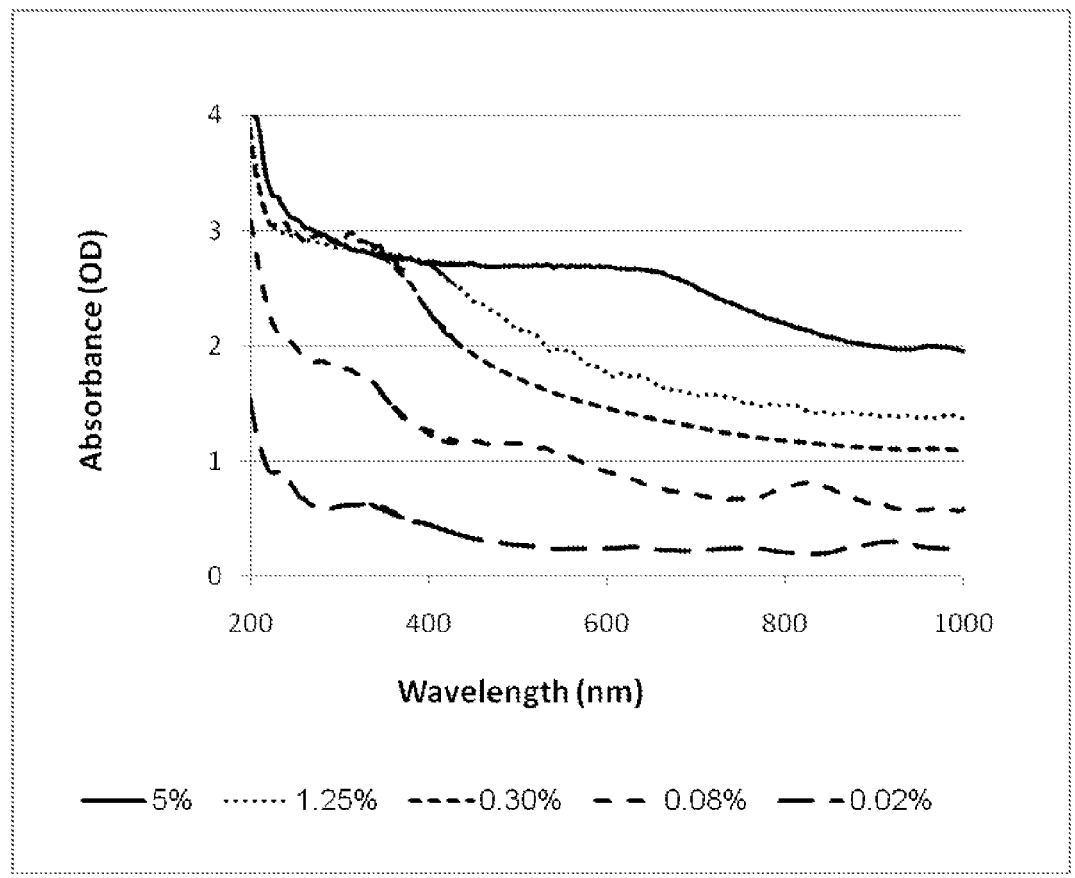
FIG. 3C is a pictorial graph displaying absorbance spectra of pretreated corn stover collected at a volume of 80 µl.
Figure 3D:
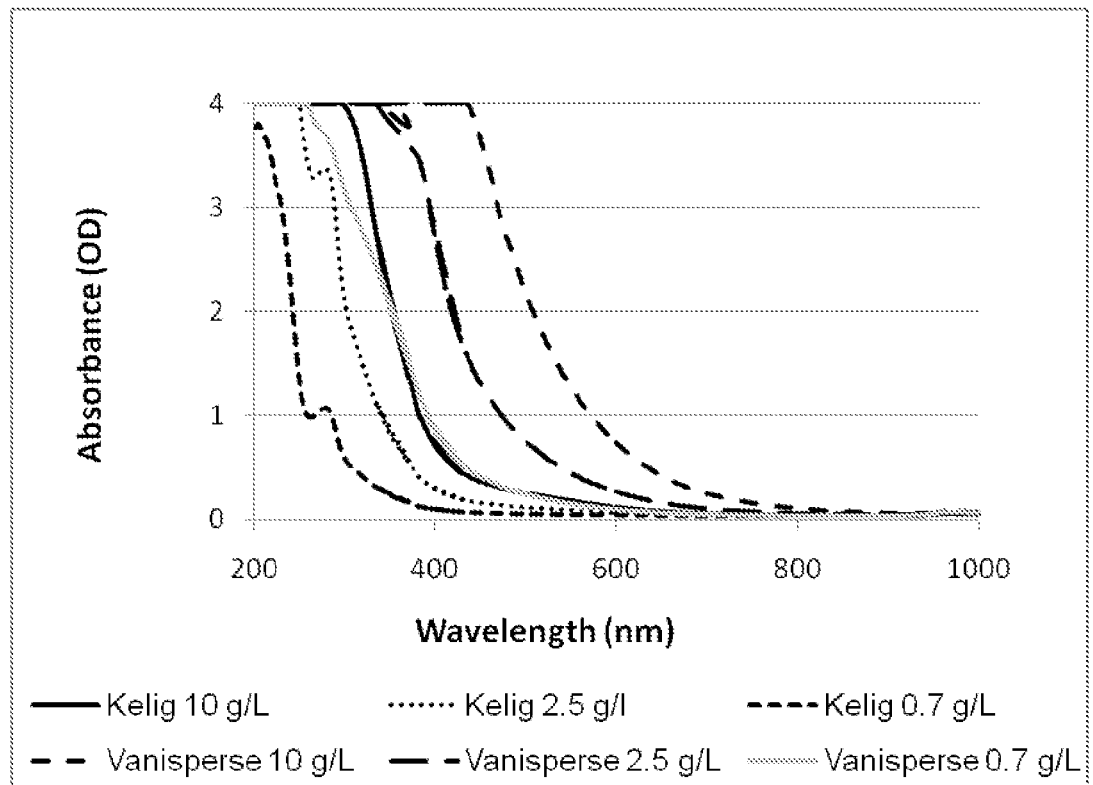
FIG. 3D is a pictorial graph displaying absorbance spectra of commercial lignins collected at a volume of 80 µl.

Referring now to FIGS. 3C and 3D, absorbance spectra were collected at a volume of 80 µl per well. The absorbance spectra of PCS-A (FIG. 3C) and the commercial lignins (FIG. 3D) showed a strong absorbance at the relevant excitation and emission wavelengths. At 5% total solids the PCS-A absorption was never below an OD of 2. Even a dilution of the PCS to below 1% total solids still showed a strong absorbance of above 1 OD in the relevant wavelength range. Measuring absorbance of the commercial lignins showed that VANISPERSE (lignin derivative) absorbed at higher wavelengths than Kelig did. Lower lignin concentrations showed a blue shift of the absorbance spectra still reaching maximal OD levels. Altogether this indicates that the emission of fluorescent brightener 28 was absorbed strongly by lignaceous residues, which was also called an inner filter effect. A similar effect could be caused by collisional quenching, but this was unlikely because an increase of FB28 concentration led to higher signal intensity and a cellulose dependent signal. This would be not expected when quenching was involved, because the increase of the fluorophore would only increase the rate of quenching.

Testing Fluorescent Brighteners in PCS Hydrolysis

After 72 hours of hydrolysis of 5% PCS-A with different loadings of CP1 FB28 was added to a final concentration of 8 µM. A cellulose dependent decrease of the signal could be observed, but the scatter was higher than the signal.

Figure 4:
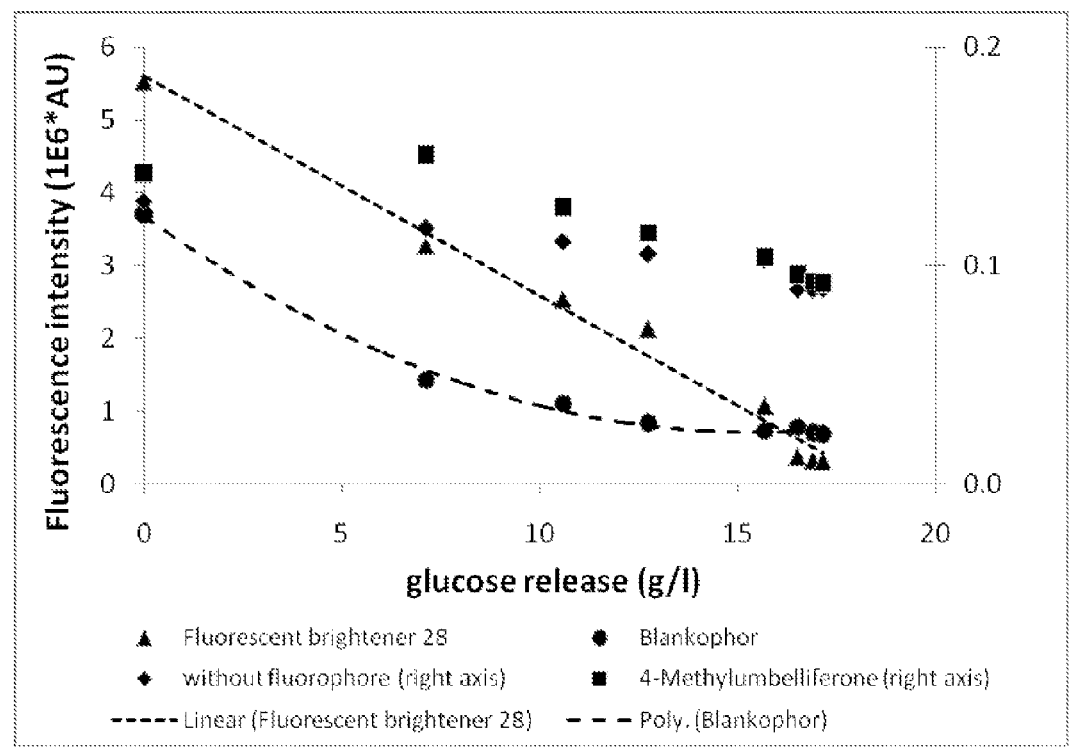
FIG. 4 is a pictorial view of a graph of fluorescent intensity in relation to glucose release where fluorescent indicator constituent is added to hydrolyzed PCS samples.
Figure 5A:
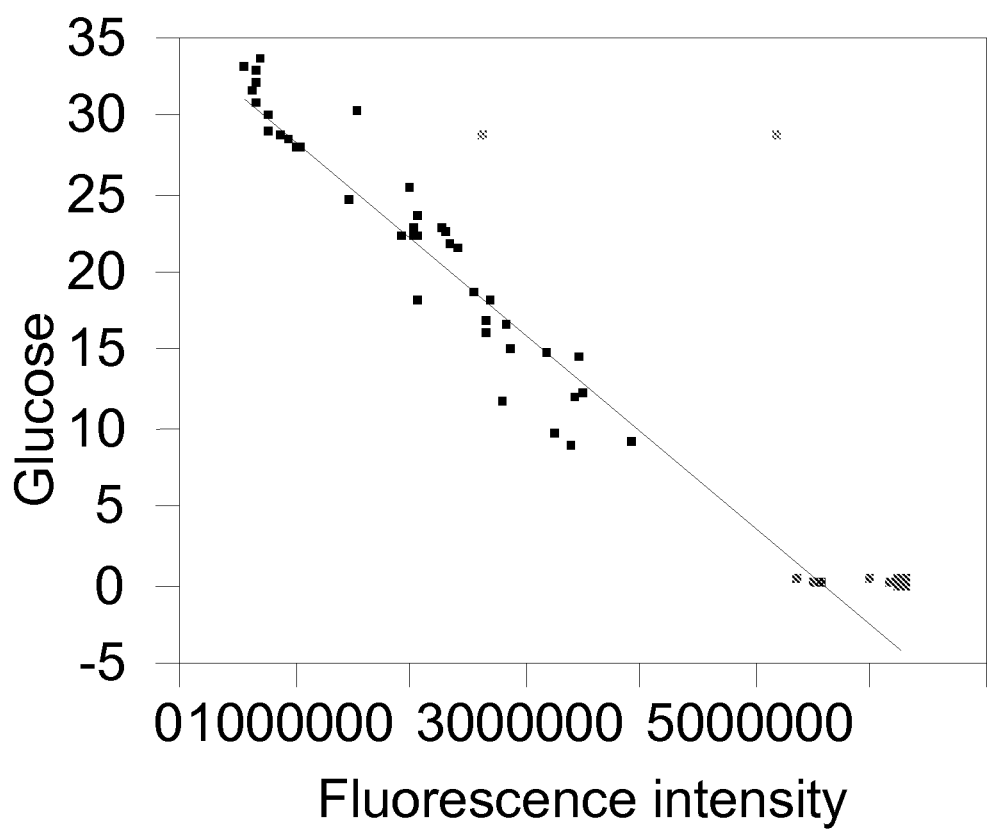
FIG. 5A is a pictorial view of a graph showing HPLC measured released glucose and corresponding fluorescence emission intensity using PCS-A samples.
Figure 5B:
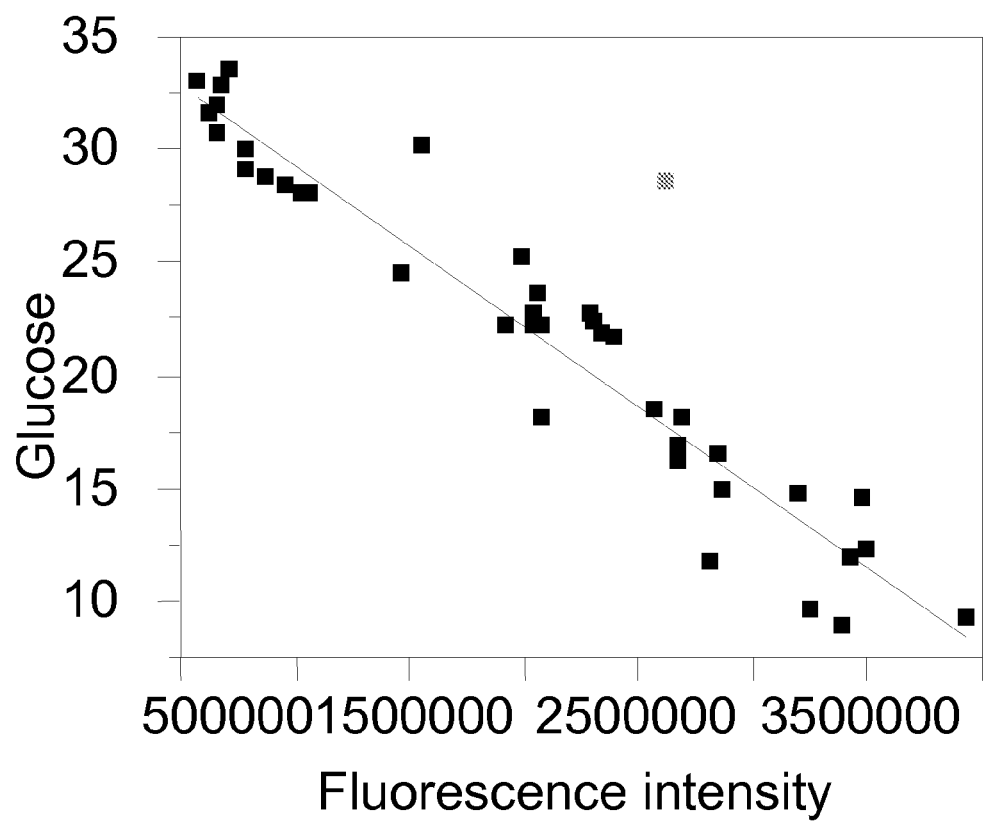
FIG. 5B is a pictorial view of a graph showing HPLC measured released glucose and corresponding fluorescence emission intensity using PCS-A samples.
Figure 5C:
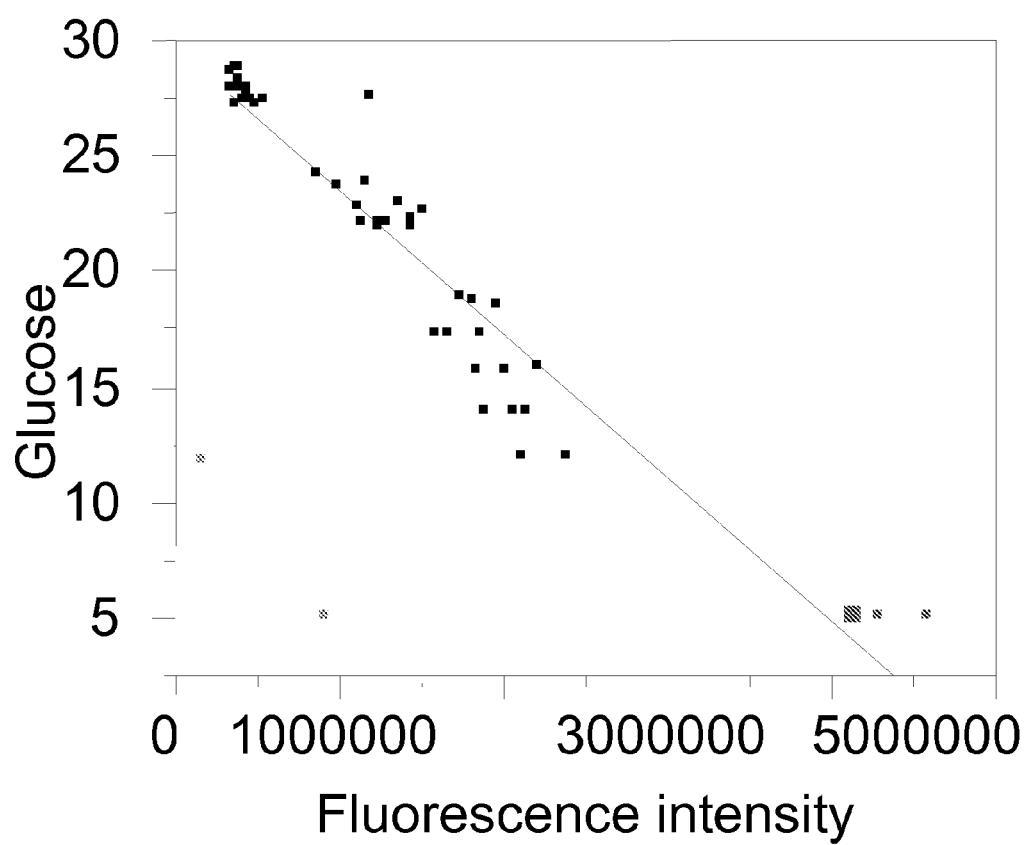
FIG. 5C is a pictorial view of a graph showing HPLC measured released glucose and corresponding fluorescence emission intensity using PCS-B samples.
Figure 5D:
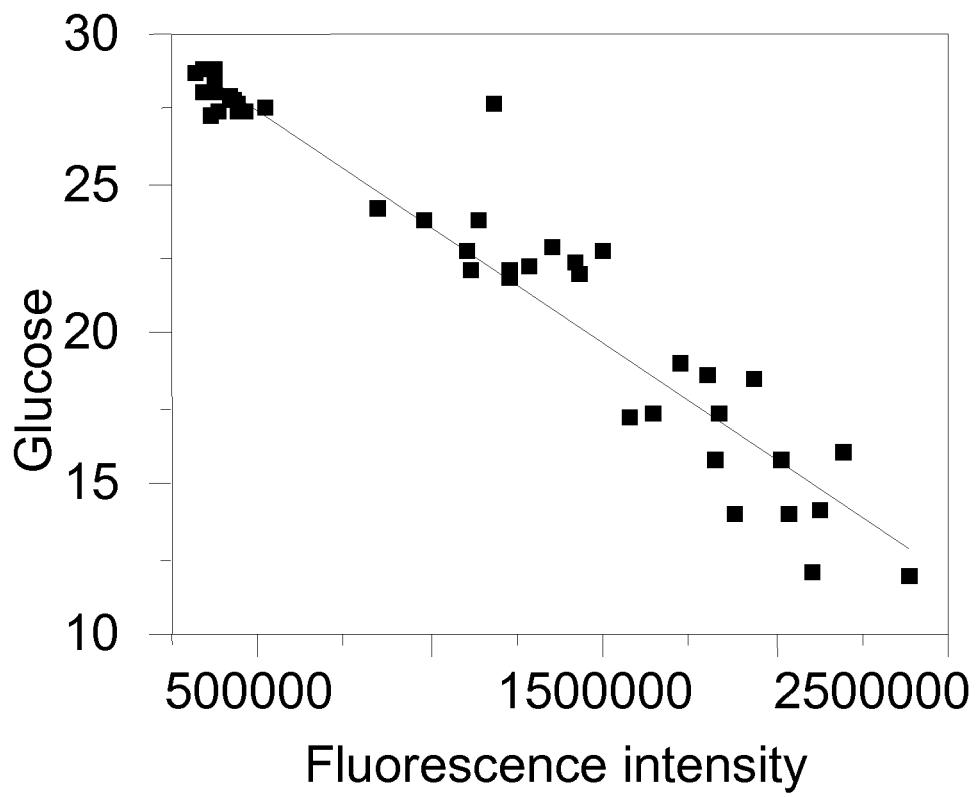
FIG. 5D is a pictorial view of a graph showing HPLC measured released glucose and corresponding fluorescence emission intensity using PCS-B samples.
Figure 5E:
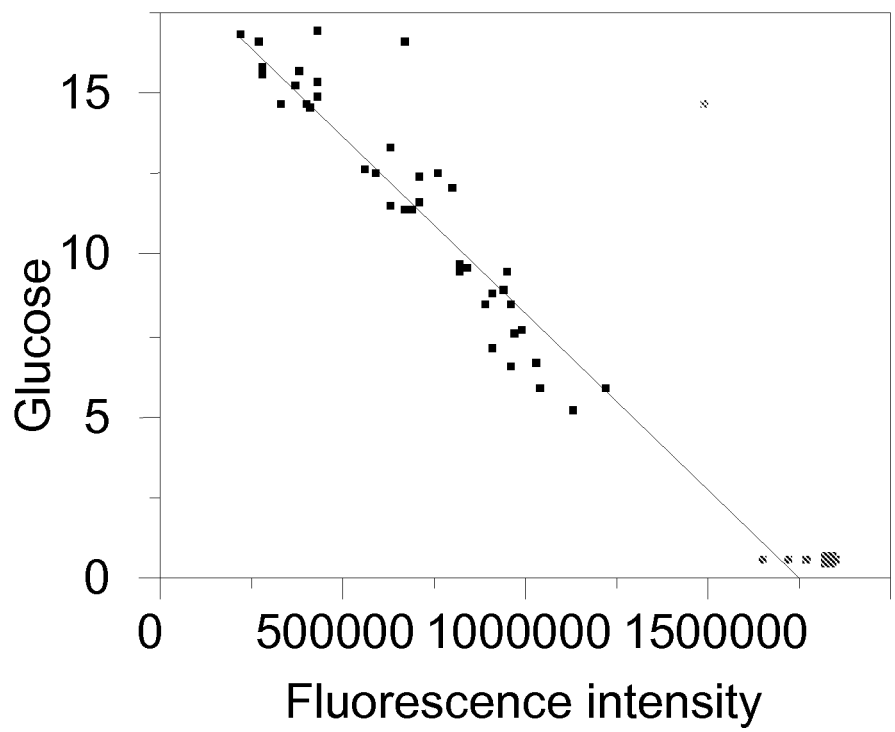
FIG. 5E is a pictorial view of a graph showing HPLC measured released glucose and corresponding fluorescence emission intensity using PCS-B samples.
Figure 5F:
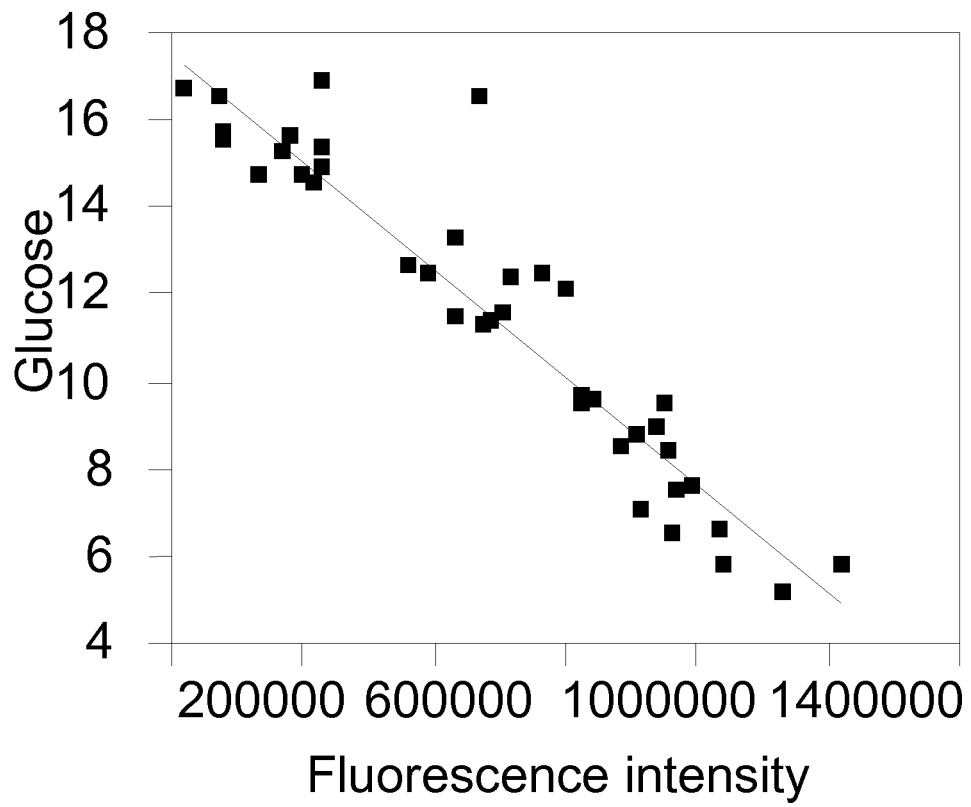
FIG. 5F is a pictorial view of a graph showing HPLC measured released glucose and corresponding fluorescence emission intensity using PCS-C samples.

Next three different fluorescent brighteners were tested at a higher concentration. Referring now to FIG. 4, addition of fluorescent brighteners to hydrolyzed PCS-A samples with indicated release glucose is shown. Closed symbols refer to the left axis, whereas open symbols are plotted on the right axis. Fluorescence emission was read through the well bottom at 465 nm with an excitation of 360 nm. More specifically, 4-methylumbelliferone, fluorescent brightener FB28 or BLANKOPHOR® brand brightener were added at concentrations of 200 µM, 380 µM, and 480 µM, respectively, to samples from a 72 hours hydrolysis of PCS-A. Alteration of the CP1 doses caused difference in the released amounts of glucose. In order to obtain a correlation between the released glucose and the emission intensity the fluorescence emission was read through the bottom. Without addition of fluorescent brighteners only a small decrease in fluorescence emission intensity was observed due to autofluorescence of cellulose. The samples with fluorescent brightener all showed a decrease of the signal at a higher release of glucose. Fluorescent brightener 28 had the highest signal ratio. Hence, it was further used at a final concentration of 200 µM. A top read showed a strongly increased emission at high degrees of hydrolysis. The hydrolysis decreased the amount of insoluble matter leading to a settling of the remaining insoluble matter. This settling insoluble matter contained the light absorbing lignin. Hence, in the topmost liquid layer the absorbance of remaining FB28 was reduced leading to a strong FB28 fluorescence signal. UV-A irradiation was also investigated, but did not significantly improve the signal to noise ratio.

Fluorescence emission was read from the bottom of, or below the reaction medium.

In embodiments, for measuring cellulose concentrations during PCS hydrolysis it is important that the lignin concentration stays constant. If in a screen on PCS hydrolysis enzyme activities destroying lignin was added, a false positive would be identified. However, this would identify a depolymerisation of the lignin, which could still be of benefit to the biomass hydrolysis.

Measuring Cellulose Decay in Hydrolysates of Different PCS

A dose response using CP1 according to a 1 ml assay was run on three different biomass samples—PCS- and GS-NREL (referred to herein simply as PCS-B) and PCS-C. Eighty μl of hydrolysis after 3 days were mixed with 10 μl of 0.5 M sodium acetate buffer at pH 5.0 and 10 μM of 2 mM FB28. Referring now to FIGS. 5A, 5B, 5C, 5D, 5E and 5F, JMP-graphs show HPLC measured released glucose and corresponding fluorescence emission intensity. Some data points showed values without addition of enzyme and were excluded in the lower graphs. A linear regression is shown as a line. FIGS. 5A, 5B, 5C, 5D, 5E and 5F show that the measured fluorescence emission was proportional to the amount of remaining cellulose, which means it was inversely proportional to the released glucose concentration measured by HPLC. In Jump, a model was built including (PCS-C) or excluding (PCS-A) the values without addition of enzyme. The average coefficient of variation or "CVs" for the fluorescence emission intensity ranged from 5.8 to 13.3%, which was high compared to 0.7 to 3.5% for the glucose measurement by HPLC.

TABLE 1

Models obtained from JMP by a linear regression

| Linear | Model m | y = mx + b standard error | y x b | Glucose Fluorescence standard error | Comment |
|---|---|---|---|---|---|
| WGS-NREL (PCS-A) | −7.14E−06 | 3.24E−07 | 36.38 | 0.72 | w/o enz. Excluded |
| GS-NREL (PCS-B) | −7.71E−06 | 3.69E−07 | 31.29 | 0.50 | w/o enz. Excluded |
| PCS-C | −1.09E−05 | 4.39E−07 | 19.07 | 0.40 | |

Under the same experimental conditions, additional testing for each biomass was conducted with and without GH61 polypeptide having cellulolytic enhancing activity. The enzyme addition was based on PCS-A with 4 mg CP2 per g cellulose. When GH61 polypeptide having cellulolytic enhancing activity was added 3.2 mg CP2 and 0.8 mg GH61 were used. The second set of conditions was with double the total enzyme concentration regarding to the latter. From the measured fluorescence emission intensities the corresponding glucose concentrations were predicted using the model equations in Table 1. These were compared to the actual glucose concentration and an average deviation of 10.4% was observed. Predicted glucose was calculated from measured fluorescence emission intensity based on the model described in Table 1. The mean plus/minus the standard deviation were plotted. The plot showed the predicted values against the actual values. The plot showed an excellent correlation between the prediction and the actual value.

Addition of Indicator Constituent to Hydrolysis

Figure 6A:
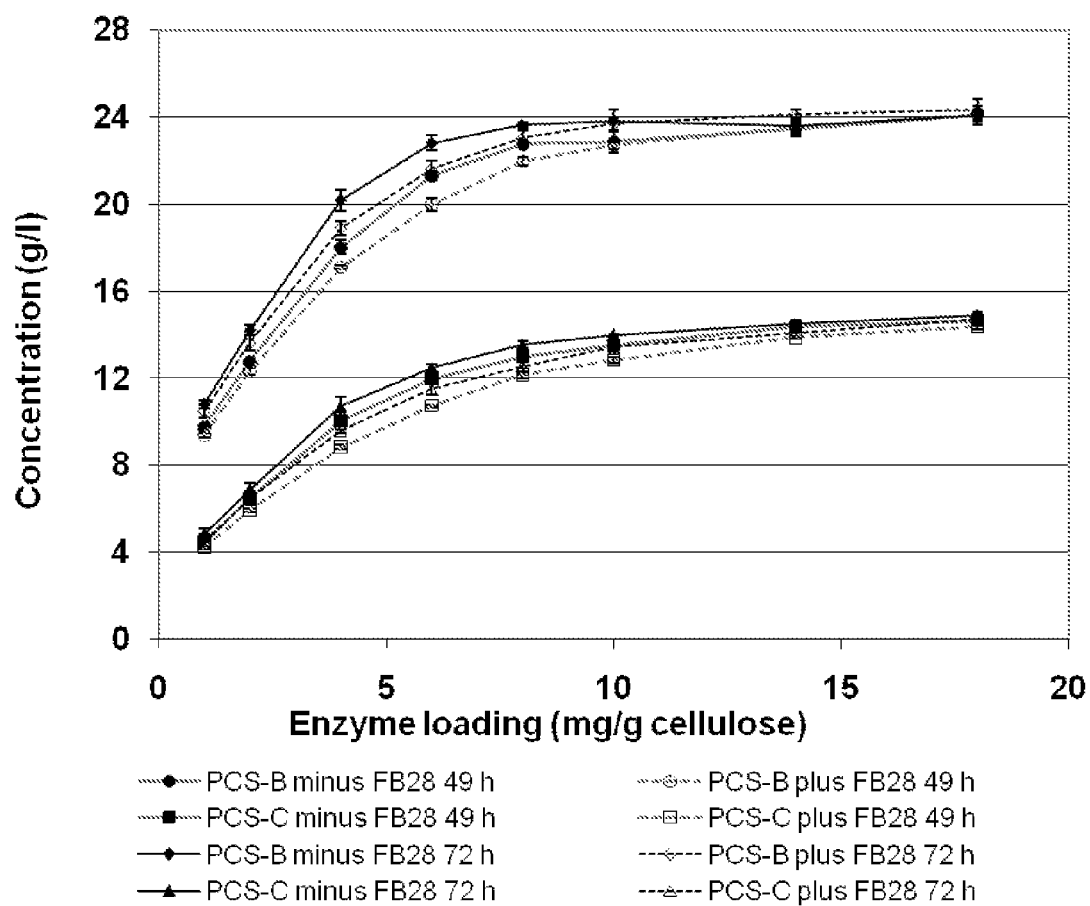
FIG. 6A is a pictorial view of a graph showing glucose concentration versus enzyme loading in various hydrolysis reactions on PCS-A and PCS-B with and without the addition of 200 µM indicator constituent.
Figure 6B:
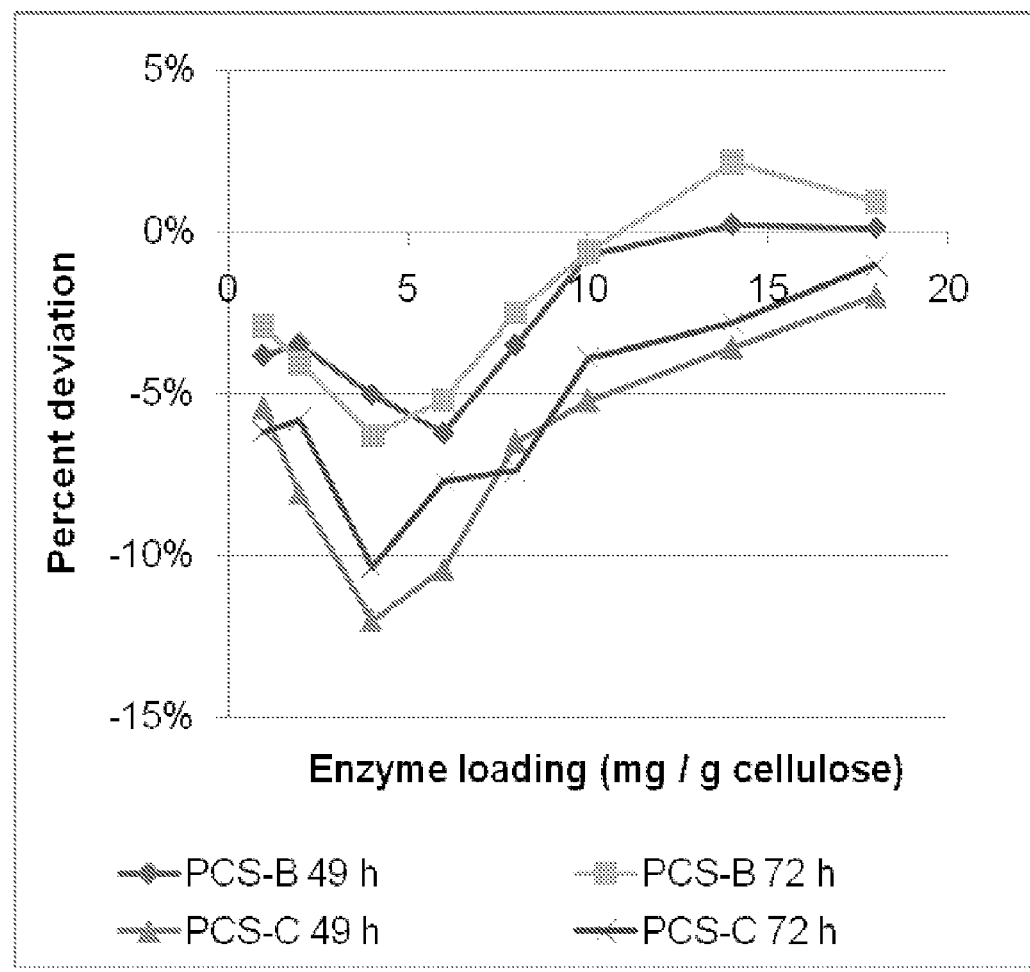
FIG. 6B is a pictorial view of a graph showing deviation of the hydrolysis with indicator constituent to the hydrolysis without indicator constituent.

The assay in accordance with the present disclosure is suitable for high-throughput screening of biomass hydrolysis because brightener such as, e.g., FB28 may be added directly to the hydrolysis reaction. This allows direct measuring during the hydrolysis reaction and not only at the endpoint. Hence, the effect of brightener addition on hydrolysis was investigated by comparing the released glucose measured by HPLC. Also, fluorescence emission intensity was measured. Referring to FIGS. 6A and 6B, PCS-B and PCS-C hydrolysis of varying CP1 dosages with and without addition of 200 μM FB28 is shown. Samples were taken at 49 hours and 72 hours and released glucose was measured by HPLC. More specifically, FIG. 6A shows glucose concentration versus enzyme loading (mg/g cellulose) during hydrolysis. FIG. 6A shows that at medium enzyme loading, the addition of FB28 caused a reduction of released glucose. Referring now to FIG. 6B, deviation of the hydrolysis with FB28 to the hydrolysis without FB28 is shown. The trend in the reduction of glucose release was also visible. The amount of released glucose was maximally reduced by 5% for PCS-B and 10% for PCS-C.

Referring now to Table 2 below, data showing glucose concentration (g/l) versus fluorescence intensity (Mio Au) in hydrolysis reaction (varying CP1 dosages with and without addition of 200 μM FB28) on PCS-B and PCS-C is shown. Fluorescence emission intensity was measured at 49 and 72 hours and samples taken for measuring released glucose by HPLC. Each average fluorescence intensity and glucose concentration measured by HPLC originates from three replicates of one enzyme dosage. Eight different enzyme doses were used in the range from 0 to 50 mg cellulose/g cellulose.

TABLE 2

| PCS - type | hydrolysis time (h) | Fluorescence intensity (Mio AU) | | Glucose concentration (g/l) | |
|---|---|---|---|---|---|
| | | Average | Standard deviation | Average | Standard deviation |
| B | 49 | 2.88 | 0.06 | 9.38 | 0.10 |
| | | 2.45 | 0.06 | 12.30 | 0.15 |
| | | 1.68 | 0.03 | 17.11 | 0.07 |
| | | 1.02 | 0.08 | 19.98 | 0.29 |
| | | 0.48 | 0.02 | 21.96 | 0.18 |
| | | 0.37 | 0.02 | 22.72 | 0.20 |
| | | 0.34 | 0.02 | 23.51 | 0.29 |
| | | 0.31 | 0.02 | 24.12 | 0.25 |
| C | 49 | 1.05 | 0.02 | 4.20 | 0.09 |
| | | 0.95 | 0.02 | 5.93 | 0.09 |
| | | 0.74 | 0.00 | 8.83 | 0.12 |
| | | 0.57 | 0.03 | 10.73 | 0.05 |
| | | 0.39 | 0.01 | 12.16 | 0.16 |
| | | 0.30 | 0.01 | 12.82 | 0.12 |
| | | 0.21 | 0.01 | 13.87 | 0.05 |
| | | 0.19 | 0.01 | 14.38 | 0.15 |
| B | 72 | 2.57 | 0.07 | 10.48 | 0.30 |
| | | 2.15 | 0.05 | 13.62 | 0.35 |
| | | 1.27 | 0.01 | 18.90 | 0.32 |
| | | 0.56 | 0.02 | 21.63 | 0.38 |
| | | 0.32 | 0.02 | 23.04 | 0.35 |
| | | 0.32 | 0.02 | 23.68 | 0.28 |
| | | 0.33 | 0.05 | 24.11 | 0.21 |
| | | 0.30 | 0.03 | 24.33 | 0.51 |
| C | 72 | 0.95 | 0.02 | 4.52 | 0.30 |
| | | 0.85 | 0.01 | 6.48 | 0.32 |
| | | 0.65 | 0.01 | 9.58 | 0.08 |
| | | 0.48 | 0.03 | 11.49 | 0.25 |
| | | 0.33 | 0.01 | 12.54 | 0.39 |
| | | 0.28 | 0.01 | 13.44 | 0.22 |
| | | 0.20 | 0.00 | 14.09 | 0.22 |
| | | 0.18 | 0.00 | 14.74 | 0.08 |

The data above was plotted. For the hydrolysis with FB28 the fluorescence emission intensity curve was similar to previous runs showing a nearly linear behavior over the examined range. The coefficient of variation (CV) was reduced to 3.9% compared to 1.6% for HPLC. When the glucose was predicted from the fluorescence data these CVs were comparable, because the glucose range was smaller than the range of the fluorescence emission signal.

Combination of Reaction and Measurement in the Same Standard Microtiter Plate

Polypropylene (PP, COSTAR® 3364) standard microtiter plates with a flat transparent bottom are well suited for running the assays in accordance with the present disclosure at a total reaction volume of 300 μl. Referring to Table 3 below, the 300 μl volume did not significantly affect hydrolysis. This was investigated at three enzyme loadings (2, 5 and 8 mg/g cellulose) without addition of FB28 and the deviation was below 3%.

TABLE 3

| | Released glucose (CV in %) | | |
|---|---|---|---|
| CP1 loading | 2 | 5 | 8 |
| 1 ml in AXYGEN ® | 4.4 (1.0) | 8.7 (0.5) | 11.4 (0.5) |
| 300 μl in COSTAR ® 3364 | 4.5 (1.5) | 8.9 (0.7) | 11.6 (0.8) |
| Deviation | 3% | 2% | 1% |

PCS-A (5%) with 200 μM FB28 was hydrolyzed by addition of different CP1 doses. The testing was performed either in 1 ml in polystyrene deep well plates or in 300 μl in polystyrene and polypropylene plates. The use of polystyrene (PS, COSTAR® 9107) standard microtiter plates was not preferred as sealing cannot be performed well leading to a weight loss of 1.8%. The mean released glucose was the same as in PP plates, but much higher scattering of the fluorescence emission intensity was observed (CV 9.3%). Without being bound by the present disclosure, it is believed that the scatter is likely caused by binding of FB28 to the PS surface via hydrophobic interactions.

In the polypropylene (PP) plates the hydrolysis in a volume of 1000 and 300 μl released similar glucose amounts. Furthermore, the normalized fluorescence emission correlated well with the glucose release measured by HPLC. Here, the fluorescence emission was normalized by subtracting it from the average intensity of a hydrolysis reaction without addition of enzyme. This sample had the highest cellulose content. For the 1 ml assay the average coefficient of variation (CV) of each of the three replicates was 6% for the HPLC measurement and 5.9% for the normalized fluorescence emission. The 300 μl assay had a CV of only 5.0% and also yielded a more linear curve.

Referring now to Table 4, PCS-A was hydrolyzed at 50° C. for 72 hours by addition of different amounts of CP1; 200 and 150 μM FB28 were added prior to hydrolysis for assays at a final of 5% and 3% total solids, respectively. The cellulose concentration dependent FB28 fluorescence emission was measured through the bottom of the microtiter plates at 465 nm after excitation at 360 nm. These values were normalized by subtraction from the mean emission intensity of unhydrolysed samples and division by a million. The glucose release was measured via HPLC. Still referring to Table 4, data is provided showing normalized fluorescence emission ($AU_0$–AU) versus glucose release of a hydrolysis reaction of PCS-A hydrolyzed at 50° C. for 72 hours by addition of different amounts of enzyme and 200 and 150 μM FB28 added prior to hydrolysis for assays at a final of 5% total solids with hydrolysis setup of 1000 μl in AXYGEN® deep well plates and 300 μl in PP standard plates (COSTAR® 3364), respectively.

TABLE 4

| | | normalized fluorescence emission in million AU of samples from | |
|---|---|---|---|
| Condition | Glucose release (g/l) | 1000 μl deep well PP | 300 μl Costar PP 3364 |
| 1 | 0.45 | 0.12 | 0.10 |
| 2 | 1.74 | 0.47 | 0.54 |
| 3 | 4.54 | 0.72 | 0.75 |
| 4 | 6.97 | 0.89 | 1.15 |
| 5 | 11.28 | 1.20 | 1.42 |
| 6 | 15.74 | 1.72 | 1.82 |
| 7 | 10.81 | 2.08 | 2.06 |
| 8 | 20.16 | 2.41 | 2.35 |
| 9 | 16.90 | 1.97 | 1.85 |
| 10 | 20.62 | 2.51 | 2.17 |
| 11 | 23.60 | 2.86 | 2.55 |
| 12 | 25.97 | 3.22 | 3.22 |
| 13 | 29.34 | 4.08 | 3.45 |
| 14 | 35.40 | 4.42 | 3.93 |
| 15 | 11.32 | 1.23 | 1.31 |
| 16 | 24.50 | 2.98 | 2.69 |
| 1 | 0.07 | −0.21 | −0.11 |
| 2 | 1.99 | 0.52 | 0.63 |
| 3 | 4.60 | 0.69 | 0.88 |
| 4 | 7.31 | 0.84 | 1.15 |
| 5 | 11.87 | 1.11 | 1.51 |
| 6 | 15.28 | 1.55 | 1.92 |
| 7 | 18.28 | 1.82 | 2.06 |
| 8 | 21.25 | 2.46 | 2.23 |
| 9 | 17.14 | 1.88 | 1.95 |
| 10 | 20.82 | 2.47 | 2.44 |
| 11 | 24.07 | 2.77 | 2.99 |
| 12 | 25.77 | 3.45 | 3.37 |
| 13 | 28.38 | 3.96 | 3.68 |
| 14 | 35.28 | 4.41 | 3.89 |
| 15 | 10.52 | 1.15 | 1.37 |
| 16 | 22.72 | 2.82 | 2.73 |
| 1 | 0.16 | 0.09 | 0.01 |
| 2 | 2.07 | 0.50 | 0.53 |
| 3 | 4.94 | 0.57 | 0.89 |
| 4 | 7.69 | 0.70 | 1.23 |
| 5 | 12.25 | 1.07 | 1.58 |
| 6 | 16.80 | 1.63 | 1.93 |
| 7 | 18.61 | 1.94 | 2.09 |
| 8 | 21.40 | 2.34 | 2.32 |
| 9 | 18.41 | 2.24 | 2.10 |
| 10 | 21.65 | 2.61 | 2.37 |
| 11 | 24.70 | 3.12 | 2.89 |
| 12 | 26.55 | 3.60 | 2.98 |
| 13 | 29.81 | 4.20 | 3.74 |
| 14 | 36.16 | 4.41 | 3.96 |
| 15 | 13.04 | 1.33 | 1.46 |
| 16 | 24.90 | 3.07 | 2.88 |

Further, the final of 3% total solids with 300 μl in PP standard plates measured directly after removal from 50° C. or after 1.5 hours at 4° C. was obtained. The results indicated that the 300 μl volume can be used for the biomass hydrolysis and the fluorescence assay was even slightly more accurate than the HPLC. After adding the enzyme to the biomass the plates were sealed at 165° C. for 1.5 seconds. This also worked excellent with only 0.1% weight loss of a full assay plate over 72 hours. Referring to Table 5, data was obtained showing normalized fluorescence emission ($AU_0$–AU) versus glucose release of a hydrolysis reaction of PCS-A hydrolyzed at 50° C. for 72 hours by addition of different amounts of enzyme and 150 μM FB28 added prior to hydrolysis for assays at a final of 3% total solids with 300 μl in PP standard plates measured directly after removal from 50° C. or after 1.5 hours at 4° C.

TABLE 5

| Condition | Glucose release (g/l) | normalized fluorescence emission in million AU measured | |
|---|---|---|---|
| | | directly after hydrolysis at 50° C. | after storage for 1.5 hours at 4° C. |
| 1 | 0.18 | 0.11 | 0.01 |
| 2 | 1.23 | 0.72 | 0.80 |
| 3 | 1.96 | 0.88 | 1.01 |
| 4 | 2.78 | 0.99 | 1.18 |
| 5 | 4.80 | 1.26 | 1.47 |
| 6 | 6.41 | 1.50 | 1.71 |
| 7 | 7.83 | 1.81 | 1.95 |
| 8 | 8.63 | 1.97 | 2.09 |
| 9 | 9.31 | 2.04 | 2.16 |
| 10 | 9.53 | 2.16 | 2.23 |
| 11 | 11.32 | 2.60 | 2.69 |
| 12 | 11.88 | 2.81 | 2.87 |
| 13 | 13.52 | 3.40 | 3.34 |
| 14 | 17.32 | 4.35 | 4.18 |
| 15 | 5.32 | 1.45 | 1.55 |
| 16 | 10.91 | 2.46 | 2.49 |
| 1 | 0.15 | −0.08 | −0.03 |
| 2 | 1.12 | 0.83 | 0.87 |
| 3 | 1.83 | 0.97 | 1.01 |
| 4 | 2.81 | 1.12 | 1.21 |
| 5 | 4.44 | 1.39 | 1.42 |
| 6 | 5.97 | 1.53 | 1.70 |
| 7 | 7.18 | 1.77 | 1.86 |
| 8 | 8.09 | 1.85 | 2.07 |
| 9 | 8.97 | 2.02 | 2.08 |
| 10 | 9.65 | 2.23 | 2.29 |
| 11 | 11.09 | 2.64 | 2.65 |
| 12 | 11.63 | 2.85 | 2.80 |
| 13 | 13.39 | 3.34 | 3.27 |
| 14 | 17.26 | 4.33 | 4.17 |
| 15 | 5.15 | 1.43 | 1.57 |
| 16 | 10.64 | 2.44 | 2.51 |
| 1 | 0.15 | −0.03 | 0.02 |
| 2 | 1.13 | 0.74 | 0.80 |
| 3 | 1.80 | 0.99 | 1.08 |
| 4 | 2.86 | 1.18 | 1.28 |
| 5 | 4.70 | 1.40 | 1.47 |
| 6 | 6.29 | 1.67 | 1.76 |
| 7 | 7.56 | 1.91 | 2.02 |
| 8 | 8.51 | 2.00 | 2.13 |
| 9 | 8.85 | 1.95 | 2.13 |
| 10 | 9.42 | 2.18 | 2.25 |
| 11 | 10.93 | 2.64 | 2.58 |
| 12 | 11.78 | 2.83 | 2.78 |
| 13 | 13.40 | 3.42 | 3.32 |
| 14 | 17.49 | 4.34 | 4.19 |
| 15 | 5.20 | 1.57 | 1.63 |
| 16 | 10.53 | 2.46 | 2.52 |

Time Courses to Evaluate Earlier Assessment of Hydrolysis

Figure 7:
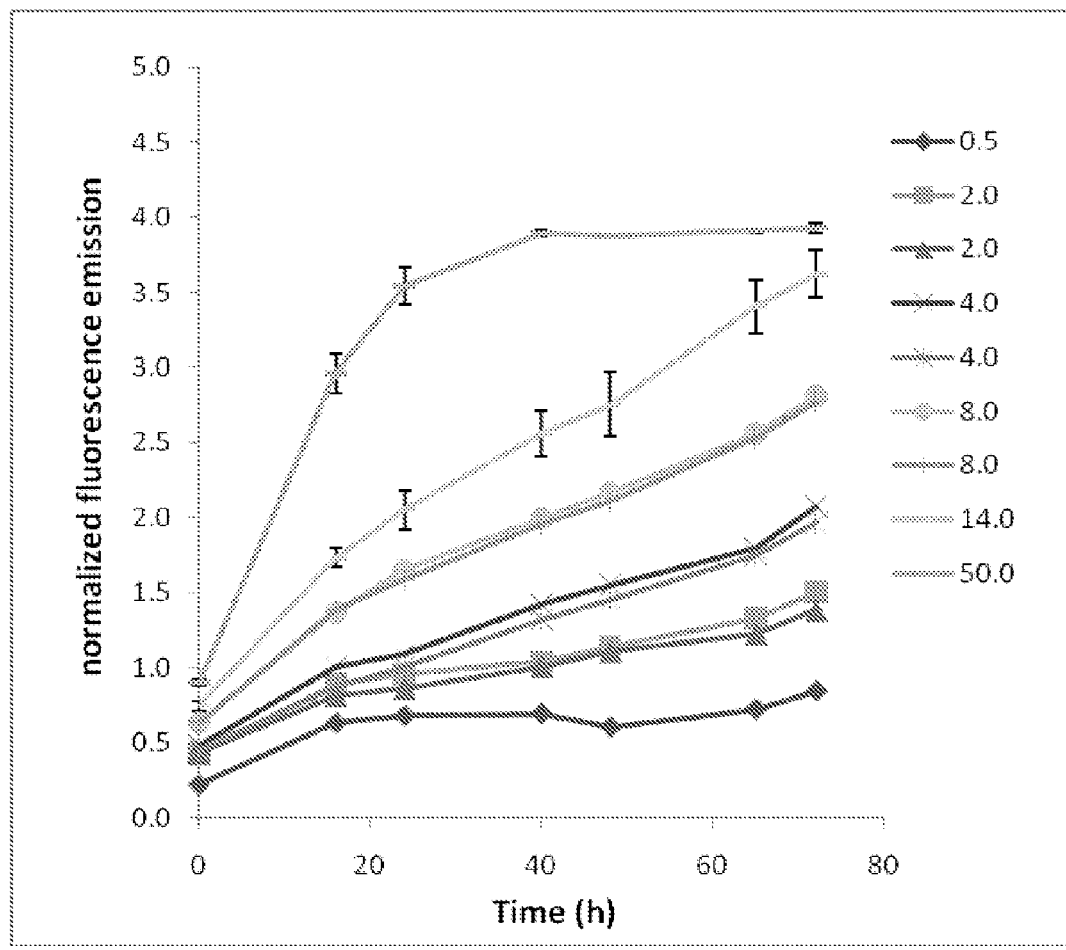
FIG. 7 is a pictorial view of a graph showing normalized fluorescence emission versus time (h) where 5% PCS-A with 200 µM FB28 was hydrolyzed at 50° C. over 72 hours by loading indicated amounts of cellulase (mg/g cellulose). Error bars show one standard deviation.

A fluorescence based assay in the PP standard plates with a flat transparent bottom can be measured more frequently and without pipetting steps compared to the current sample preparation for HPLC analysis with mixing, removal, and filtration. Referring now to FIG. 7, a time course for different enzyme loadings of CP1 is shown. More specifically, 5% WGS NREL PCS with 200 µM FB28 was hydrolyzed at 50° C. over 72 hours by loading indicated amounts of CP1 (mg/g cellulose). Normalized fluorescence emission was measured and calculated at different time point as indicated in FIG. 7. Error bars showed one standard deviation. Duplicates lined up nicely.

Checking Different Total Solid Loadings and Respective FB28 Concentrations

Because pipetting of PCS with the robot for 5% final total solids is difficult, lower total solid loadings at 3% and 1% were investigated. The FB28 concentration had to be adjusted to each total solids loading due to the varying lignin concentration, which quenches the FB28 emission. Optimal or improved results were obtained using 3% total solids loading with 150 µM FB28. The measurement was either done directly after removal from the 50° C. incubator or after 1.5 hours storage at 4 C. The CVs were improved significantly compared to the 5% total solids assay. At 3% total solids the CV of the HPLC glucose determination was 2.5%, the CV of the direct fluorescence measurement was 3.6% and after storage at 4° C. it was even reduced to 2.3%. A nearly linear correlation between normalized fluorescence emission and released glucose was observed. The correlation coefficient was 0.97. For the direct fluorescence measurement the glucose can be calculated from the following formula:

$$\text{glucose (g/l)} = 4.576 * \text{normalized fluorescence emission} - 1.250. \quad \text{Model 1}$$

Figure 8:
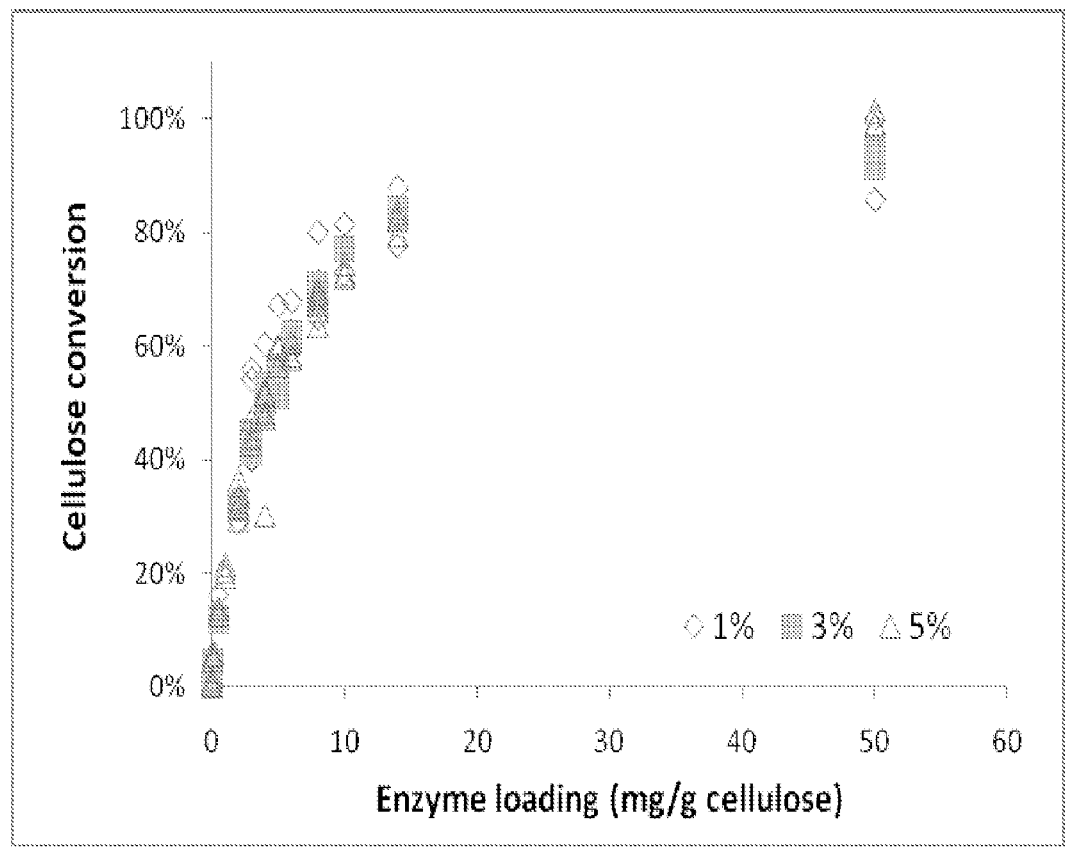
FIG. 8 is a pictorial view of a graph showing 1%, 3%, and 5% PCS-A with 4, 16 and 204 µM FB28, respectively, hydrolyzed at 50° C. over 72 hours by addition of different amounts of Trichoderma reesei cellulolytic protein composition (Trichoderma reesei strain RutC30 broth including GH61 polypeptide having cellulolytic enhancing activity and Aspergillus oryzae beta-glucosidase fusion protein) obtained according to WO 2008/151079. Released glucose was measured by HPLC and cellulose conversion was based on maximal glucose release at 5% total solids.

Referring now to FIG. 8, 1%, 3%, and 5% PCS-A with 4, 16, and 204 µM FB28, respectively, was hydrolyzed at 50° C. over 72 hours by addition of different amounts of CP1. Released glucose was measured by HPLC and cellulose conversion was based on maximal glucose release at 5% total solids. The assays at 3% and 5% total solids showed similar dose response curves of the HPLC measured cellulose conversion. As a major difference 7% less released glucose was observed only at the highest enzyme loading. At 1% total solids a high scattering of the released glucose was observed. At 1% also the total release of glucose was only a third of that at 3%. At lower glucose amounts the error of the HPLC measurement increased. Furthermore, smaller amounts of enzyme were pipetted leading to higher errors in the pipetting. These two reasons could lead to higher errors in determined conversion.

Also the volume in the assay was tested because 300 µl was the filling limit of the polypropylene microtiter plates (COSTAR® 3364). When a total assay volume of 150 to 300 µl was tested, the fluorescence signal and its noise increased at lower volumes. Excellent results were obtained with volumes between 250 and 300 µl. The data was obtained and is shown in Table 6 below:

TABLE 6

| Total solids of PCS | total enzyme loading (mg total enzyme/g cellulose) | cellulose conversion |
|---|---|---|
| 5.0% | 0.00 | 1.28% |
| 5.0% | 0.10 | 4.88% |
| 5.0% | 0.50 | 12.76% |
| 5.0% | 1.00 | 19.58% |
| 5.0% | 2.00 | 31.68% |
| 5.0% | 3.00 | 44.19% |
| 5.0% | 4.00 | 30.36% |
| 5.0% | 5.00 | 56.61% |
| 5.0% | 4.00 | 47.47% |
| 5.0% | 6.00 | 57.90% |
| 5.0% | 8.00 | 66.28% |
| 5.0% | 10.00 | 72.94% |
| 5.0% | 14.00 | 82.39% |
| 5.0% | 50.00 | 99.40% |
| 5.0% | 2.00 | 31.78% |
| 5.0% | 8.00 | 68.79% |
| 5.0% | 0.00 | 0.20% |
| 5.0% | 0.10 | 5.59% |
| 5.0% | 0.50 | 12.92% |
| 5.0% | 1.00 | 20.53% |
| 5.0% | 2.00 | 33.33% |
| 5.0% | 3.00 | 42.90% |
| 5.0% | 4.00 | 51.32% |
| 5.0% | 5.00 | 59.68% |
| 5.0% | 4.00 | 48.12% |
| 5.0% | 6.00 | 58.48% |
| 5.0% | 8.00 | 67.59% |
| 5.0% | 10.00 | 72.38% |
| 5.0% | 14.00 | 79.70% |

TABLE 6-continued

| Total solids of PCS | total enzyme loading (mg total enzyme/g cellulose) | cellulose conversion |
|---|---|---|
| 5.0% | 50.00 | 99.06% |
| 5.0% | 2.00 | 29.54% |
| 5.0% | 8.00 | 63.79% |
| 5.0% | 0.00 | 0.44% |
| 5.0% | 0.10 | 5.80% |
| 5.0% | 0.50 | 13.88% |
| 5.0% | 1.00 | 21.59% |
| 5.0% | 2.00 | 34.39% |
| 5.0% | 3.00 | 47.19% |
| 5.0% | 4.00 | 52.27% |
| 5.0% | 5.00 | 60.10% |
| 5.0% | 4.00 | 51.70% |
| 5.0% | 6.00 | 60.79% |
| 5.0% | 8.00 | 69.35% |
| 5.0% | 10.00 | 74.57% |
| 5.0% | 14.00 | 83.71% |
| 5.0% | 50.00 | 101.54% |
| 5.0% | 2.00 | 36.62% |
| 5.0% | 8.00 | 69.91% |
| 3.0% | 0.00 | 0.13% |
| 3.0% | 0.10 | 4.31% |
| 3.0% | 0.50 | 12.43% |
| 3.0% | 0.00 | 0.25% |
| 3.0% | 3.00 | 45.12% |
| 3.0% | 3.00 | 44.80% |
| 3.0% | 4.00 | 51.76% |
| 3.0% | 5.00 | 56.57% |
| 3.0% | 4.00 | 50.18% |
| 3.0% | 6.00 | 60.66% |
| 3.0% | 8.00 | 69.32% |
| 3.0% | 10.00 | 77.16% |
| 3.0% | 14.00 | 82.72% |
| 3.0% | 50.00 | 91.29% |
| 3.0% | 2.00 | 31.85% |
| 3.0% | 8.00 | 68.96% |
| 3.0% | 0.00 | 0.07% |
| 3.0% | 0.10 | 4.16% |
| 3.0% | 0.50 | 12.15% |
| 3.0% | 0.00 | 0.11% |
| 3.0% | 3.00 | 43.37% |
| 3.0% | 3.00 | 42.69% |
| 3.0% | 4.00 | 48.96% |
| 3.0% | 5.00 | 51.81% |
| 3.0% | 4.00 | 53.15% |
| 3.0% | 6.00 | 62.28% |
| 3.0% | 8.00 | 70.67% |
| 3.0% | 10.00 | 77.05% |
| 3.0% | 14.00 | 84.26% |
| 3.0% | 50.00 | 94.05% |
| 3.0% | 2.00 | 31.29% |
| 3.0% | 8.00 | 67.41% |
| 3.0% | 0.00 | 0.18% |
| 3.0% | 0.10 | 4.32% |
| 3.0% | 0.50 | 11.63% |
| 3.0% | 0.00 | 0.12% |
| 3.0% | 3.00 | 41.20% |
| 3.0% | 3.00 | 42.98% |
| 3.0% | 4.00 | 48.53% |
| 3.0% | 5.00 | 51.01% |
| 1.0% | 0.00 | 0.38% |
| 1.0% | 0.10 | 4.12% |
| 1.0% | 0.50 | 11.57% |
| 1.0% | 0.00 | 0.23% |
| 1.0% | 3.00 | 41.77% |
| 1.0% | 3.00 | 43.99% |
| 1.0% | 4.00 | 50.43% |
| 1.0% | 5.00 | 55.09% |
| 1.0% | 4.00 | 51.91% |
| 1.0% | 6.00 | 67.88% |
| 1.0% | 8.00 | 80.15% |
| 1.0% | 10.00 | 81.44% |
| 1.0% | 14.00 | 87.90% |
| 1.0% | 50.00 | 100.08% |
| 1.0% | 2.00 | 32.92% |
| 1.0% | 8.00 | 71.35% |
| 1.0% | 0.00 | 0.10% |
| 1.0% | 0.10 | 5.74% |
| 1.0% | 0.50 | 16.15% |
| 1.0% | 0.00 | 0.10% |
| 1.0% | 3.00 | 56.08% |
| 1.0% | 3.00 | 54.10% |
| 1.0% | 4.00 | 60.26% |
| 1.0% | 5.00 | 67.13% |
| 1.0% | 4.00 | 50.38% |
| 1.0% | 6.00 | 62.73% |
| 1.0% | 8.00 | 71.06% |
| 1.0% | 10.00 | 77.67% |
| 1.0% | 14.00 | 83.33% |
| 1.0% | 50.00 | 92.78% |
| 1.0% | 2.00 | 31.28% |
| 1.0% | 8.00 | 68.63% |
| 1.0% | 0.00 | 0.26% |
| 1.0% | 0.10 | 3.98% |
| 1.0% | 0.50 | 12.18% |
| 1.0% | 0.00 | 0.21% |
| 1.0% | 3.00 | 40.20% |
| 1.0% | 3.00 | 39.80% |
| 1.0% | 4.00 | 47.90% |
| 1.0% | 5.00 | 53.45% |
| 1.0% | 4.00 | 48.44% |
| 1.0% | 6.00 | 59.40% |
| 1.0% | 8.00 | 67.88% |
| 1.0% | 10.00 | 72.86% |
| 1.0% | 14.00 | 77.71% |
| 1.0% | 50.00 | 85.82% |
| 1.0% | 2.00 | 28.96% |
| 1.0% | 8.00 | 65.06% |

Pipetting PCS with Robot

A procedure for filling 4 COSTAR® 3364 PP plates twice with 120 μl each was developed. Fifty mg CP1/g cellulose enzyme and buffer were added resulting in a final volume of 300 μl. After incubation for 72 hours the coefficient of variation (CV) of the total amount released glucose was 0.4 to 0.5% for the inner wells. This indicated that the PCS pipetting was very consistent. AXYGEN® widebor tips and Beckman brand tips were tested. A slightly lower CV for the Beckman brand tips was found, but occasionally outliers appeared. In embodiments, widebor tips with a broader opening are recommended.

Evaluation with Known and Unknown Enzyme Mixtures of Interest

The assay using indicator constituent, such as FB28, for measuring the cellulose amount in 3% PCS hydrolysis in COSTAR® 3364 microtiter plates was tested for its prediction capability. Three known enzyme preparations were tested. The known enzyme mixes were CP1, CP2, *Trichoderma reesei* strain RutC30 cellulase. On each plate the three enzyme preparations were analyzed in triplicate with 2, 5, 6, 7, or 8 mg enzyme per g cellulose dose. In addition, at 5 mg/g cellulose loading 20% of the enzyme preparation was substituted by GH61 polypeptide having cellulolytic enhancing activity. In addition, in the outer wells 2 and 8 mg/g cellulose were loaded for each enzyme in order to compare between inner and outer well performance. As standards the assay needs triplicates of no enzyme addition and 50 mg CP1/g cellulose. Incubation was performed at 50° C. with daily inversion for 72.5 hours. The plates were read at an excitation of 360 nm and an emission of 465 nm from the bottom. HPLC analysis was performed to obtain real conversion data based on glucose and cellobiose.

*Trichoderma reesei* strain RutC30 cellulase contained only low amounts of beta-glucosidase. The assay in accordance with the present disclosure measures residual cellulose and generally does not distinguish between glucose, cellobiose, or short beta 1,4-glucans. Hence, for calculation of the conversion the HPLC measured glucose and cellobiose were taken into account, whereas previously the cellobiose was often neglected as it was low in CP1 and CP2 hydrolysates due to a higher content of *A. oryzae* beta glucosidase.

Figure 9A:
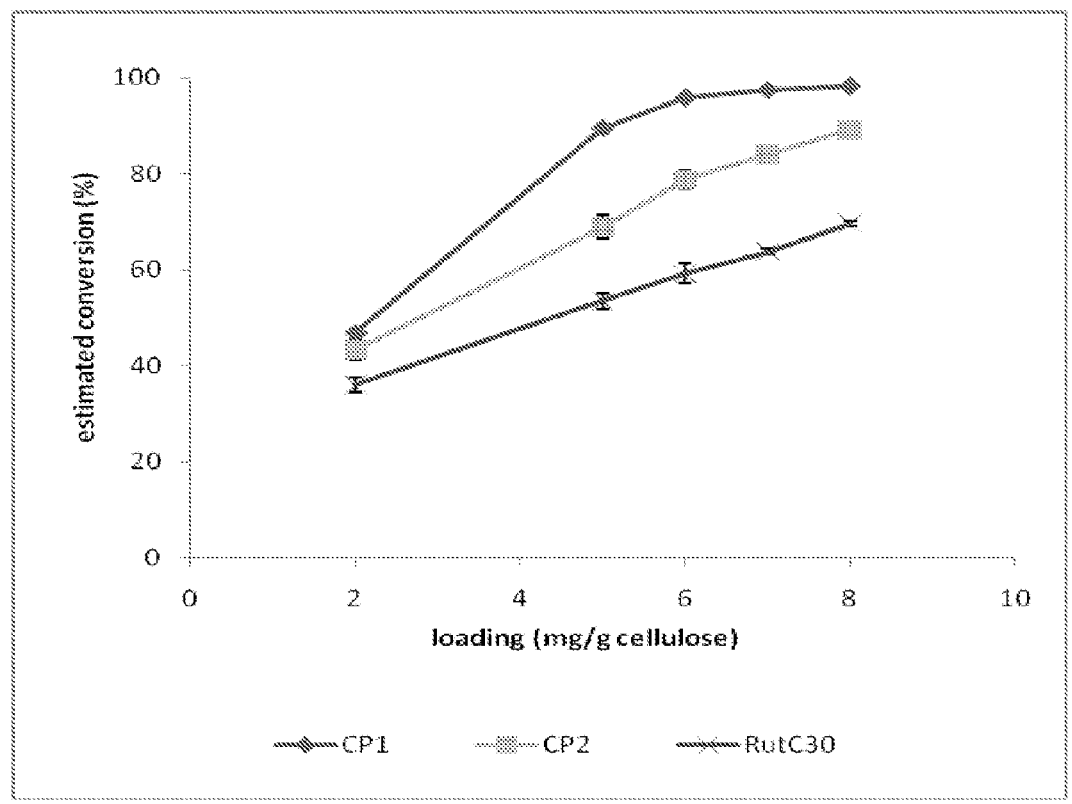
FIG. 9A is a pictorial view of a graph showing estimated conversion (%) versus loading (mg/g cellulose) where PCS-A was hydrolyzed at 50° C. for 72 hours using 300 µl reaction in COSTAR® 3364 plates with 3% PCS and 150 µM FB28.
Figure 9B:
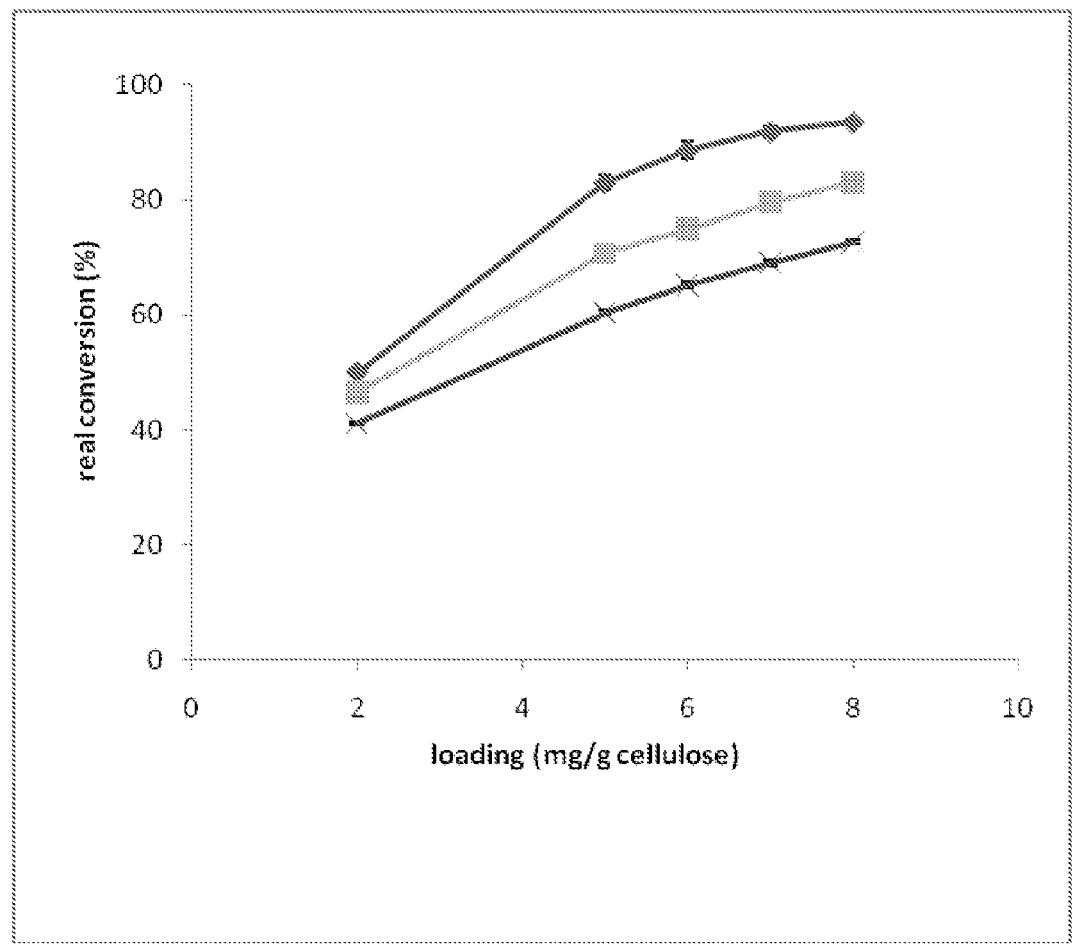
FIG. 9B is a pictorial view of a graph showing real conversion (%) versus loading (mg/g cellulose) where real conversion was based on glucose and cellobiose measured by HPLC form the reaction in FIG. 9A.

Referring now to FIG. 9A, washed ground sieved PCS-A was hydrolyzed at 50° C. for 72 hours in 300 µl reaction in COSTAR® 3364 plates with 3% PCS and 150 µM FB28. Conversion was estimated from fluorescence emission measurement at 360 nm excitation and 465 nm emission. The following model equation was used: glucose (g/l)=4.593* (AU0−AU)/1E6−1.379. This model equation was used to estimate glucose based conversion and similar results to the glucose and cellobiose based conversion from HPLC were obtained. See for example FIG. 9B showing real conversion based on glucose and cellobiose measured by HPLC form the reaction in FIG. 9A. Earlier cellobiose was not taken into account, because it was negligibly low in CP1 and CP2 dose responses. In *Trichoderma reesei* strain cellulase beta-glucosidase (BG) was missing and high cellobiose levels were obtained. In the assay the FB28 measures the amount of cellulose and cannot distinguish between glucose and cellobiose. In the comparison total conversion is not the same, but all samples can be classified in the right order, i.e.:

CP1>CP2>*Trichoderma reesei* strain RutC30

Figure 10A:
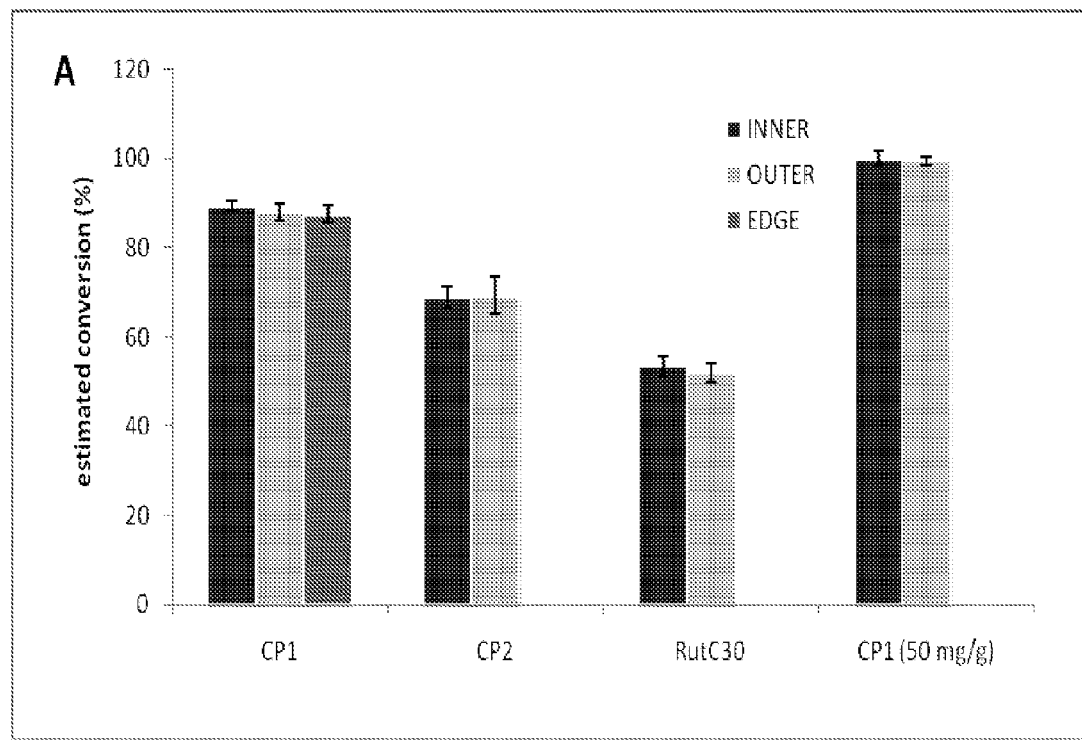
FIG. 10A is a pictorial view of a histogram showing analysis of one embodiment of the present disclosure with estimated conversion in inner, outer, and edge wells with a loading of 5 mg/g cellulose.
Figure 10B:
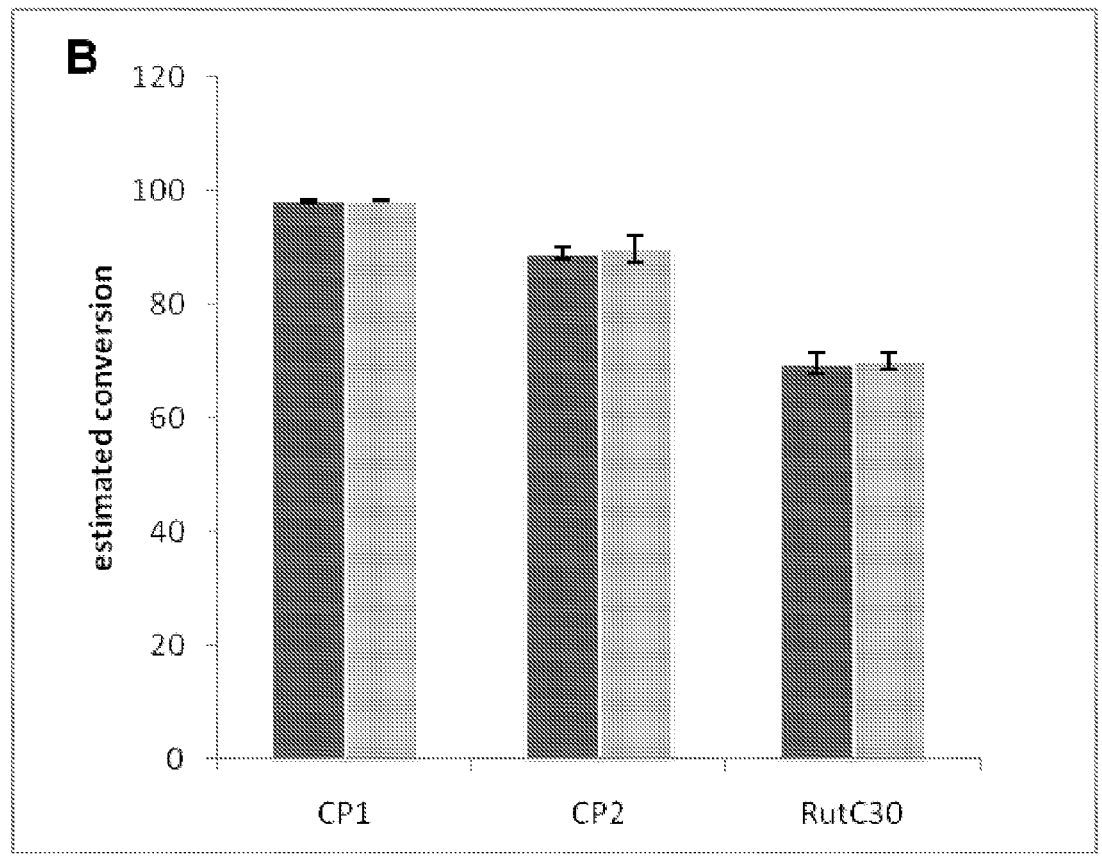
FIG. 10B is a pictorial view of a histogram showing analysis of one embodiment of the present disclosure with estimated conversion in inner, outer and edge wells with a loading of 8 mg/g cellulose. Note: RutC30 refers to Trichoderma reesei strain RutC30.
Figure 11:
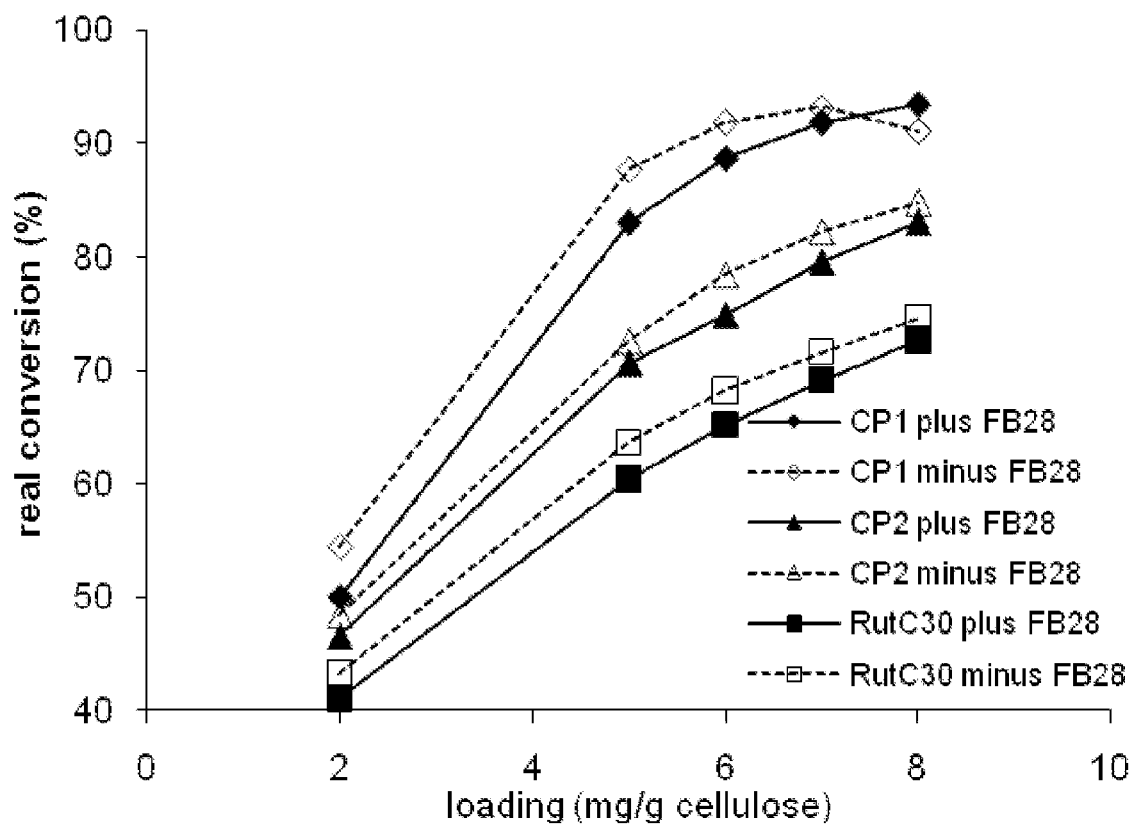
FIG. 11 is a pictorial view of a graph showing real conversion (%) versus loading (mg/g cellulose) in a 3% PCS-A reaction hydrolyzed with a first set of enzymes for 72 hours at 50° C. with (+) or without (−) 150 µM FB28. Real conversion was calculated from HPLC measurements of glucose and cellobiose. Real conversion was calculated from HPLC measurements of glucose and cellobiose.

Referring now to FIGS. 10A and 10B, an analysis of assay estimated conversion in inner, outer, and edge wells with a loading of 5 and 8 mg/g cellulose is shown, respectively. Inner and outer wells showed the same performance, so the whole plate can be utilized. Also the influence of FB28 on the conversion was investigated again. Plates without addition of FB28 showed about 5% higher conversion. The dose response curves with FB28 were nearly always simply shifted downwards in the conversion by 5%. See FIG. 11, where 3% WGS-NREL PCS was hydrolyzed for 72 hours at 50° C. with (+) or without (−) 150 µM FB28. Real conversion was calculated from HPLC measurements of glucose and cellobiose. FIG. 11 show different sets of enzymes with (solid line, closed symbol) and without FB28 (dashed line, open symbol).

Prediction Modeling

The present data was used to develop models based on a new normalization of the fluorescence emission signal. The normalization included a division by the maximal signal after 72 hours hydrolysis for a 50 mg/g loading of CP1:

$$100 \cdot \frac{\overline{AU}_0 - AU}{(\overline{AU}_0 - \overline{AU}_{50})_{72h}} \quad \text{Model 2}$$

with AU as the arbitrary units of fluorescence emission intensity at the measurement time, $\overline{AU}_0$ as the average of wells without enzyme addition (highest AU value), and $\overline{AU}_{50}$ as the average of wells with 50 mg CP1/g cellulose.

This normalization requires a complete digest ($\overline{AU}_{50,min}$) as performed by 50 mg CP1/g cellulose in 72 hours. This new normalization (model 2) is basically the percentage of conversion when the conversion of 50 mg/g cellulose at 72 hours is set to 100% and the relationship between the fluorescence signal and the cellulose content is linear. The aim was to make this normalized value more independent of the measuring apparatus, because actual measured values of the fluorescence emission intensity can vary significantly between readers. This worked well, so that when a plate with varying conversion in PCS hydrolysis was measured on different Beckmann DTX plate readers the average deviation from the reference reader was below 6%. See e.g., Table 7 showing data for a plate with varying degrees of PCS hydrolysis measured at excitation 360 nm and emission at 465 nm with different Beckmann DTX readers. The Zero values in Reader #3 were not measured data points.

The data from Table 7 below shows normalized signal ($100*(AU_0-AU)/(AU_0-AU_{50})_{72h}$) of different Beckmann DTX readers (#1-™4) where a plate with varying degrees of PCS hydrolysis was measured at excitation 360 nm and emission at 465 nm.

TABLE 7

| reader #1 | reader #2 | reader #2, repeated read | reader #3 | reader #4 |
|---|---|---|---|---|
| 98.1 | 99.1 | 99.3 | 98.4 | 99.4 |
| 28.4 | 27.1 | 27.4 | 29.8 | 33.3 |
| 45.0 | 46.8 | 46.8 | 48.5 | 51.7 |
| 63.0 | 63.4 | 63.7 | 65.7 | 67.8 |
| 60.4 | 60.5 | 60.9 | 63.1 | 65.5 |
| 44.4 | 46.0 | 46.4 | 47.1 | 50.0 |
| 31.8 | 34.6 | 35.0 | 33.9 | 36.2 |
| 67.4 | 68.6 | 69.0 | 70.2 | 72.8 |
| 52.4 | 52.9 | 53.0 | 53.4 | 56.7 |
| 50.1 | 52.3 | 51.9 | 52.1 | 56.5 |
| 47.5 | 47.8 | 47.7 | 49.7 | 51.3 |
| 55.9 | 57.9 | 57.8 | 57.5 | 60.6 |
| 52.9 | 53.6 | 54.1 | 55.8 | 58.0 |
| 50.2 | 52.8 | 53.3 | 52.1 | 55.2 |
| 47.7 | 51.0 | 50.9 | 49.6 | 53.4 |
| 45.9 | 45.8 | 46.0 | 47.5 | 51.8 |
| 60.5 | 58.5 | 59.2 | 61.1 | 64.2 |
| 62.0 | 62.7 | 63.2 | 64.5 | 66.6 |
| 22.0 | 14.0 | 14.6 | 16.3 | 20.6 |
| 17.3 | 15.0 | 15.2 | 14.3 | 16.3 |
| 18.9 | 15.0 | 15.5 | 17.5 | 20.0 |
| 40.7 | 39.0 | 39.1 | 41.9 | 45.9 |
| 54.5 | 53.8 | 53.8 | 54.6 | 58.8 |
| 55.0 | 54.2 | 54.7 | 56.8 | 59.7 |
| 57.9 | 57.9 | 58.3 | 59.8 | 62.4 |
| 102.2 | 101.0 | 100.8 | 102.3 | 101.5 |
| 29.0 | 26.5 | 26.3 | 29.3 | 32.7 |
| 51.2 | 49.3 | 48.9 | 51.2 | 54.9 |
| 64.1 | 63.5 | 63.5 | 64.1 | 68.0 |
| 61.7 | 61.5 | 61.0 | 62.7 | 65.3 |
| 19.6 | 16.7 | 16.6 | 16.6 | 19.3 |
| 46.4 | 45.7 | 45.4 | 44.7 | 50.2 |
| 49.5 | 50.9 | 50.9 | 51.5 | 54.7 |
| 48.0 | 47.0 | 47.9 | 46.9 | 52.2 |
| 47.1 | 44.7 | 44.3 | 45.8 | 50.5 |
| 58.8 | 58.0 | 57.9 | 57.8 | 62.4 |
| 56.1 | 57.5 | 57.5 | 58.1 | 60.8 |
| 52.5 | 53.1 | 53.2 | 52.9 | 55.6 |
| 48.6 | 48.3 | 48.3 | 48.4 | 51.4 |
| 46.3 | 45.7 | 46.0 | 46.5 | 50.8 |
| 63.9 | 61.6 | 61.9 | 63.8 | 66.3 |
| 66.2 | 65.6 | 66.2 | 66.2 | 69.2 |
| 20.3 | 16.3 | 16.3 | 18.0 | 20.0 |
| 15.9 | 11.6 | 11.7 | 12.6 | 13.7 |
| 17.1 | 10.3 | 10.6 | 13.5 | 14.8 |
| 20.8 | 14.5 | 15.1 | 18.8 | 20.4 |
| 41.6 | 37.7 | 38.1 | 41.1 | 44.4 |
| 53.6 | 52.7 | 52.4 | 53.7 | 56.8 |
| 55.8 | 54.8 | 54.9 | 56.4 | 59.0 |
| 56.7 | 56.5 | 57.0 | 57.3 | 60.7 |
| 99.7 | 99.8 | 99.9 | 99.4 | 99.1 |
| 31.0 | 27.0 | 27.2 | 27.8 | 30.0 |
| 47.0 | 46.9 | 47.2 | 48.3 | 50.7 |
| 64.3 | 62.4 | 62.7 | 64.3 | 66.6 |
| 63.2 | 61.1 | 61.0 | 61.9 | 64.5 |
| 47.5 | 47.9 | 47.5 | 48.1 | 50.3 |
| 52.6 | 55.0 | 55.2 | 54.4 | 55.6 |
| 46.8 | 48.3 | 48.3 | 47.0 | 49.2 |
| 43.3 | 43.2 | 42.7 | 43.7 | 46.1 |
| 44.0 | 42.9 | 43.2 | 42.8 | 44.5 |
| 55.2 | 56.9 | 57.0 | 56.9 | 59.3 |
| 54.4 | 53.9 | 54.2 | 54.8 | 57.3 |
| 50.4 | 51.3 | 51.7 | 51.5 | 51.6 |
| 45.3 | 46.9 | 46.7 | 46.9 | 46.9 |
| 44.2 | 43.6 | 43.9 | 44.5 | 46.3 |
| 59.9 | 59.2 | 58.5 | 61.3 | 62.7 |

TABLE 7-continued

| reader #1 | reader #2 | reader #2, repeated read | reader #3 | reader #4 |
|---|---|---|---|---|
| 61.7 | 64.2 | 63.9 | 63.5 | 64.6 |
| 16.5 | 13.2 | 13.3 | 16.5 | 15.7 |
| 14.3 | 10.4 | 10.7 | 12.4 | 10.3 |
| 37.2 | 39.5 | 39.5 | 38.4 | 38.9 |
| 51.3 | 52.9 | 53.3 | 52.0 | 52.3 |
| 52.8 | 54.3 | 54.6 | 52.8 | 53.9 |
| 52.4 | 54.8 | 54.9 | 54.4 | 53.6 | prediction was invalid. From 20 to 85% the prediction was for both biomass lots slightly to low. Above 85% to 100% the assay in accordance with the present disclosure predicted very well for lot 96 and yielded slightly too low values for lot 81. In the range above 20% the average deviation from the real value was 5.6% for lot 91 and 8.8% for lot 96.

The data below in Table 8 shows the estimated conversion (%) from fluorescence intensity versus HPLC measured conversion (%) after 72 hours hydrolysis of two different PCS-A lots.

TABLE 8

| | total enzyme loading | | | | | | | | | | | |
|---|---|---|---|---|---|---|---|---|---|---|---|---|
| (mg | KCMF 1752-81 | | | | | | KCMF 1752-96 | | | | | |
| protein/g | Replicate 1 | | Replicate 2 | | Replicate 3 | | Replicate 1 | | Replicate 2 | | Replicate 3 | |
| cellulose) | HPLC | estimate | HPLC | estimate | HPLC | estimate | HPLC | estimate | HPLC | estimate | HPLC | estimate |
| 0 | 0.04 | −3.66 | 0.03 | 2.84 | 0.04 | 0.82 | 0.28 | −3.49 | 0.00 | 1.85 | 0.03 | 1.63 |
| 50 | 100.00 | 99.52 | 99.91 | 100.35 | 98.97 | 100.12 | 100.00 | 99.72 | 105.89 | 99.99 | 103.42 | 100.30 |
| 2 | 44.39 | 35.99 | 43.88 | 41.23 | 43.56 | 39.31 | 43.33 | 36.65 | 43.26 | 38.74 | 42.49 | 37.37 |
| 5 | 73.08 | 68.89 | 74.87 | 72.07 | 73.91 | 72.66 | 75.17 | 65.09 | 75.16 | 66.81 | 73.89 | 67.53 |
| 8 | 91.12 | 94.23 | 87.26 | 93.82 | 87.28 | 94.94 | 87.31 | 86.76 | 88.40 | 86.65 | 90.04 | 87.33 |
| 5 | 85.72 | 82.18 | 84.41 | 83.52 | 84.85 | 83.42 | 86.02 | 78.95 | 85.39 | 77.10 | 85.08 | 80.06 |
| 0.1 | 2.37 | 8.02 | 2.22 | 16.56 | 2.12 | 12.69 | 2.11 | 7.69 | 1.72 | 14.99 | 2.24 | 14.82 |
| 0.2 | 8.30 | 14.66 | 8.09 | 15.93 | 8.57 | 16.16 | 8.41 | 14.36 | 8.18 | 18.68 | 8.08 | 18.37 |
| 0.5 | 14.78 | 14.07 | 16.18 | 18.77 | 14.10 | 15.70 | 14.22 | 15.09 | 13.77 | 20.37 | 13.99 | 16.05 |
| 1 | 28.31 | 24.38 | 31.27 | 30.50 | 28.63 | 27.53 | 27.52 | 25.52 | 27.27 | 25.78 | 27.26 | 21.99 |
| 2 | 43.71 | 37.00 | 47.40 | 44.70 | 42.34 | 36.87 | 42.19 | 35.66 | 41.57 | 36.91 | 41.25 | 34.50 |
| 3 | 56.48 | 50.47 | 62.94 | 59.89 | 55.17 | 49.12 | 55.35 | 48.23 | 54.72 | 51.82 | 54.52 | 47.16 |
| 4 | 66.63 | 60.80 | 72.29 | 71.81 | 63.64 | 58.84 | 64.28 | 54.84 | 64.33 | 58.57 | 64.48 | 56.61 |
| 5 | 76.55 | 71.14 | 81.09 | 84.26 | 74.76 | 69.35 | 73.51 | 65.97 | 72.80 | 65.61 | 73.00 | 64.50 |
| 8 | 89.68 | 90.15 | 88.49 | 95.81 | 84.87 | 88.28 | 85.04 | 0.00 | 83.84 | 82.97 | 86.94 | 83.26 |
| 10 | 91.71 | 96.26 | 91.88 | 97.98 | 89.49 | 95.49 | 90.93 | 91.06 | 91.27 | 90.99 | 93.13 | 90.29 |
| 14 | 96.18 | 98.38 | 94.64 | 98.43 | 94.82 | 98.19 | 98.34 | 94.79 | 97.42 | 96.43 | 96.92 | 95.26 |
| 18 | 97.94 | 98.93 | 98.30 | 98.94 | 96.68 | 99.19 | 100.56 | 97.57 | 99.42 | 97.91 | 98.28 | 97.30 |
| 50 | 99.39 | 100.52 | 99.66 | 101.04 | 99.57 | 100.02 | 105.72 | 99.90 | 103.81 | 100.21 | 102.91 | 99.93 |

Figure 12:
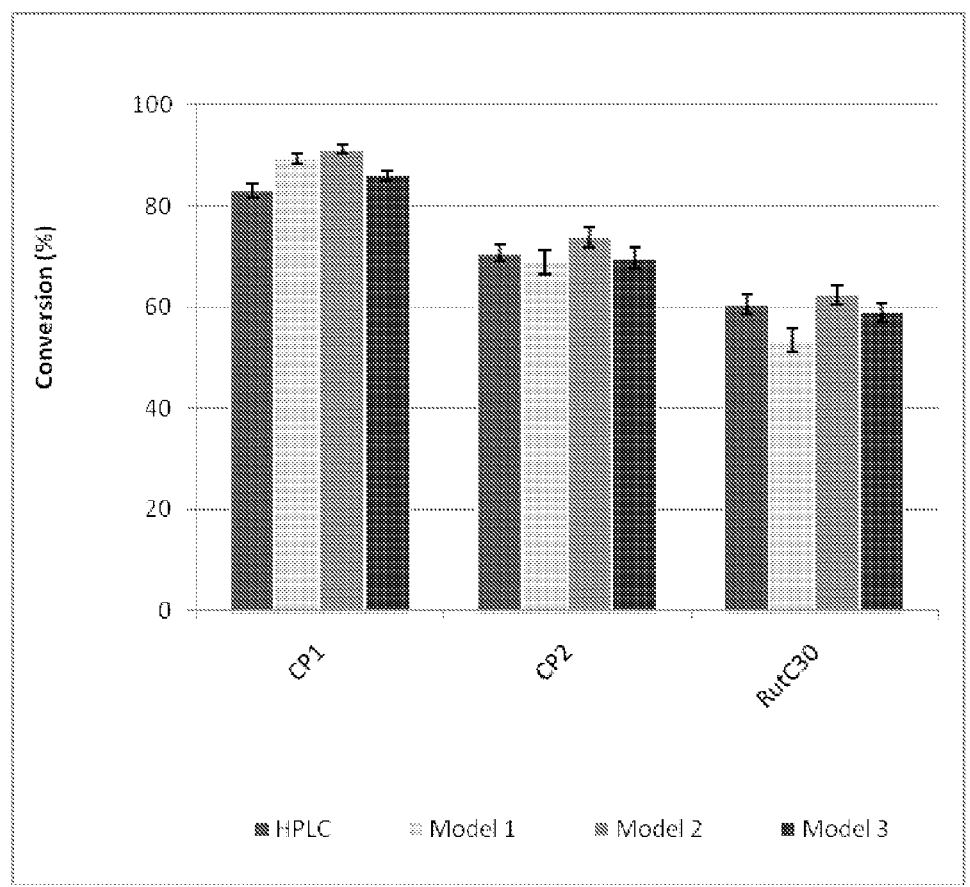
FIG. 12 is a pictorial view of a histogram showing conversion (%) versus different enzymes using various models. Comparison of real HPLC measured conversion of cellulose into glucose and cellobiose with models from fluorescence emission intensity measurements is shown. Note: RutC30 refers to Trichoderma reesei strain RutC30.

The actual cellulose content of PCS-A KCMF 1752-81 in a 50 mg/g loading at 50° C. in 168 hours was determined in a 50 g assay as 59.17%. In the 300 µl scale only 94.3% of this cellulose was degraded in 72 hours. When the normalized signal was multiplied by 0.943 an excellent fit of the data was obtained (model 3) describing the data better than model 1 and 2. See FIG. 12 which shows a comparison of real HPLC measured conversion of cellulose into glucose and cellobiose with models from fluorescence emission intensity measurements. Model 1 uses ($AU_0-AU$) as variable in a linear model with intercept. Model 2 is $100*(AU_0-AU)/(AU_0-AU_{50})_{72h}$ and model 3 corrects this value by 94.3%, which is the maximal cellulose conversion reached in this assay by 50 mg CP1 per g cellulose. In embodiments, model 2 would be used if the maximal digestion in the assay in accordance with the present disclosure is set to 100% and would then have the same prediction power as model 3.

Figure 13A:
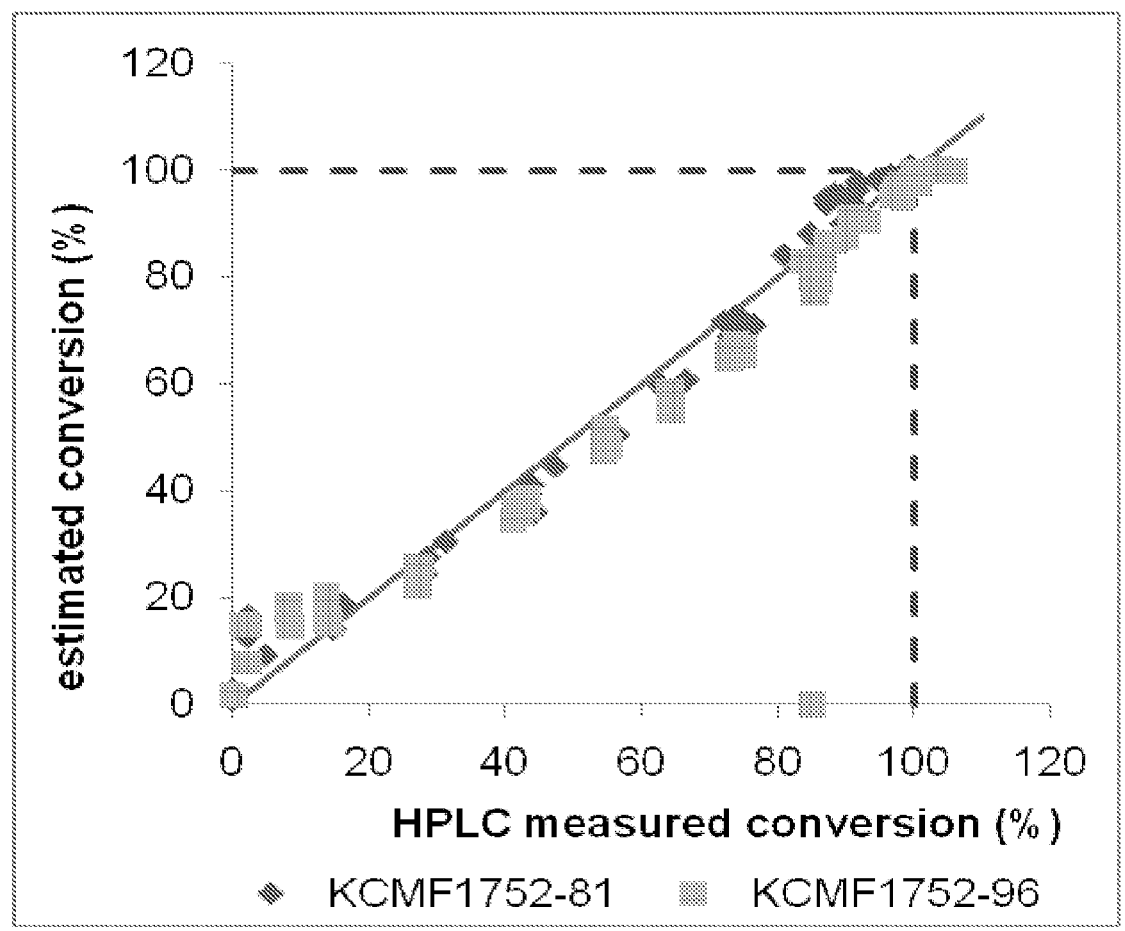
FIG. 13A is a pictorial view of a graph showing estimated conversion (%) versus HPLC measured conversion (%) after 72 hours hydrolysis of two different PCS-A lots.
Figure 13B:
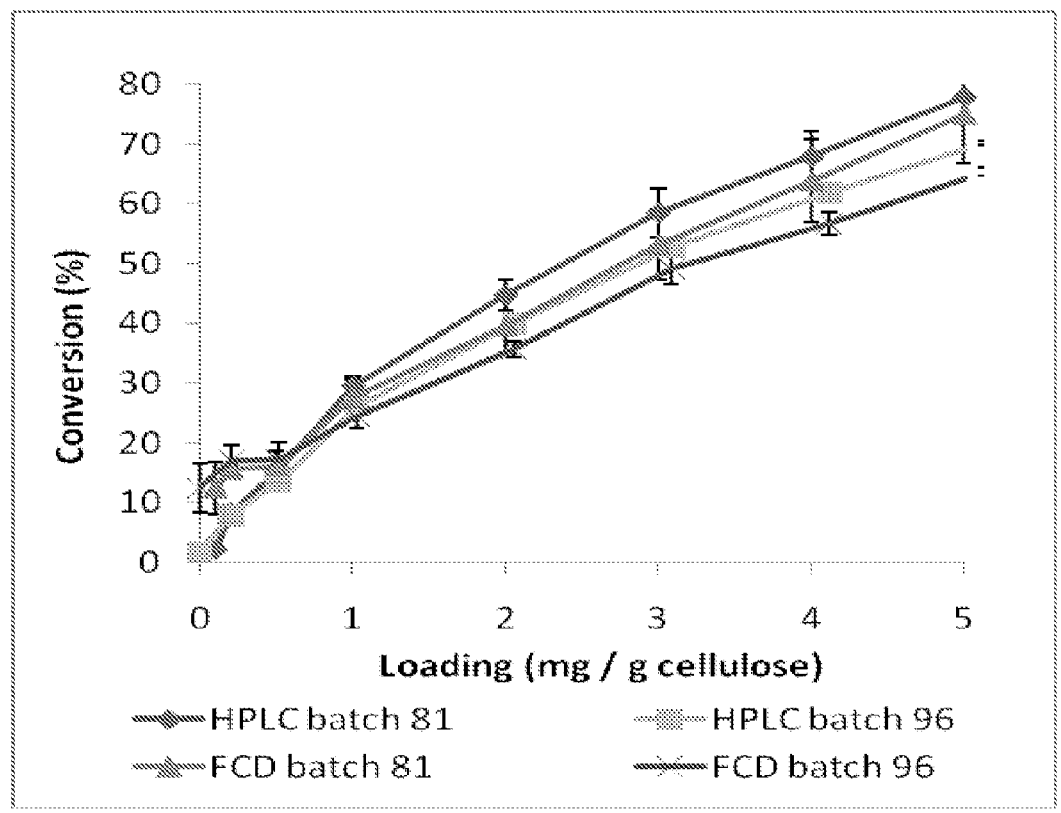
FIG. 13B is a pictorial view of a graph showing estimated conversion (%) versus loading (mg/g cellulose) plotted as magnification of certain doses.
Figure 13C:
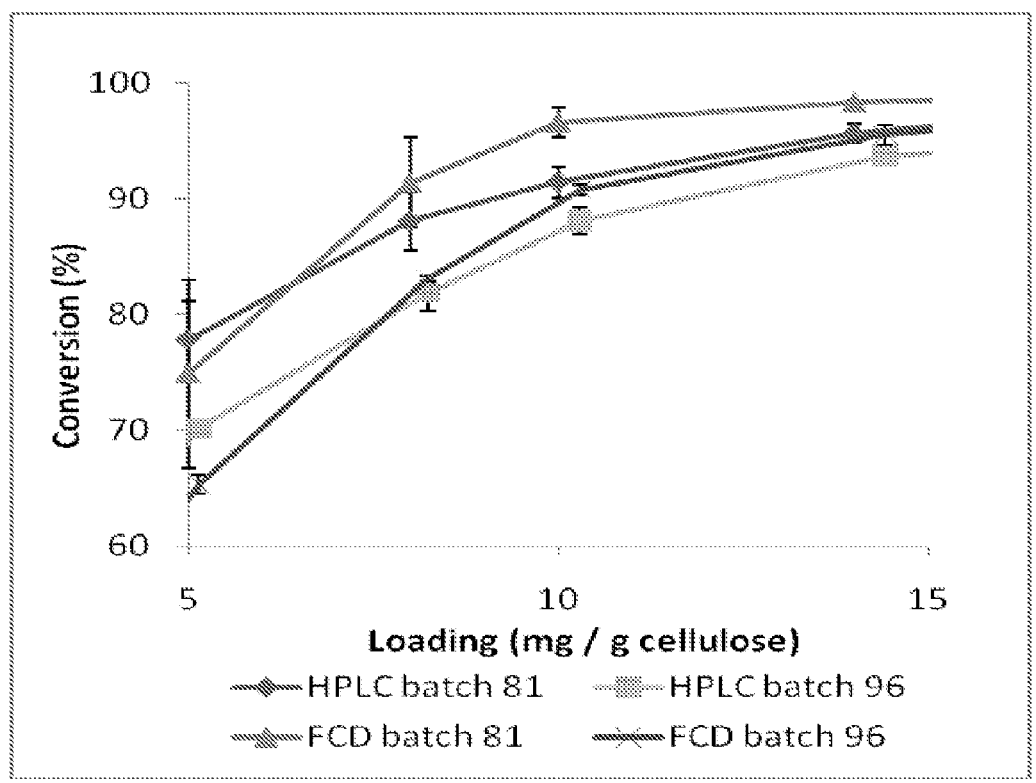
FIG. 13C is a pictorial view of a graph showing estimated conversion (%) versus loading (mg/g cellulose) plotted as magnification of certain doses.

PCS-A from the current lot (KCMF1752-81) and from a new lot (KCMF1752-96) was tested in a new PCS hydrolysis experiment in which CP1 was again used at different dosages. After 72 hours the maximal HPLC measured cellulose conversion of 50 mg CP1 per g cellulose was set to be 100% for both biomasses, so that simply model 2 could be applied. A comparison of the estimated conversion versus the real HPLC measured conversion is shown in FIG. 13A. Below 20% the A dose response curve of the HPLC measured conversion showed that the WGS-NREL-PCS from lot 96 needed a higher amount of enzyme for 80% conversion than lot 81 (See FIG. 13B). At higher and lower conversions the curves merged again (See FIG. 13C). This was also observed in the assay estimate, but some deviations from the HPLC measured conversion were present. Accordingly, the assay in accordance with the present disclosure was excellent to compare different enzyme mixes to each other on one biomass sample and also between different biomasses.

The above results show that fluorescent brightener 28 can be used to rank the hydrolysis performance of different enzyme mixes on the same PCS with the same buffer system. Other indicator constituents were useful.

This assay may also be used with other biomass samples. A correlation for unwashed ground sieved PCS-C and NREL PCS was already shown, but other biomass samples such as corn fiber, corn cobs, switchgrass, bagasse, etc. were suitable for use in accordance with the present disclosure.

Example 2

Studies were performed on various indicator constituents suitable for use in the methods in accordance with the present disclosure. More specifically, various dyes and their fluorescence behavior coupled with different biomass substrate were studied. FB28 dye showed excellent qualities.

In embodiments, methods of the present disclosure encounter small amounts of background absorbance from lignin (represented below by Kelig). Such background absorbance from lignin is best minimized or avoided, thus studies were performed to identify reaction conditions. The goal was to identify an indicator constituent that emits at an alternate wavelength and hence reduces any disturbance from lignin. Various spectra of various dye-biomass combinations were reviewed.

The dyes and biomass evaluated are summarized in Tables 9 and 10, respectively. The dyes were prepared as 0.6 g/L solution, the substrates being 36 g/L, both in DDI water. To obtain spectra, appropriate dye solution was mixed with either corresponding substrate or DDI water (Dye only) at a ratio of 1:5. Similarly, 1:5 ratio of water:biomass was used to make substrate only samples. Then 300 µl of such samples was placed into one of the wells in a 96-well COSTAR® 3364 µlate for fluorescence detection on a fluorescent plate reader purchased from Molecular Devices, model M5. All spectra were obtained by exciting the material at 360 nm and then recording fluorescence over the wavelength from 400-500 nm.

pared to those of the dyes, which were typically stretching in the range of 20 k to 120 k fluo units or above.

Most of the dye spectra have λmax in the area around 450 nm, similar to FB28. However, it was found that FB28 was superior in lowering the influence of lignin (e.g., Kelig) fluorescene in the region.

Spectra of Various Dyes with WGS 3% PCS

WGS PCS (30 g/L; 3%) was mixed with a range of fluorescent dyes and their spectra were created. Compared to the dye alone spectra, all the dyes suffered quenching of fluorescence upon addition of 3% WGS PCS, partially caused by the pigment and known or unknown chemicals that were contained in the liquor of PCS solution. From the results, BLANKOPHOR® brand brightener, Tinopal 5BM-GX, Tinopal CBS-X and FB28 were identified as excellent for fluorescence studies on WGS PCS. These 4 dyes have λmax of 450 nm or less.

The fluorescence of FB28 was examined upon mixing with various substrates: (a) overall spectra; and (b) spectra with fluorescence units ranging from 10-100 k were illustrated.

TABLE 9

| Dye | Manufacturer | Cat.# | M.W. | Light sensitive Y/N |
| --- | --- | --- | --- | --- |
| rhodamine b | Sigma-Aldrich ® | r-6626 | 479 | Y |
| tinopal 5BM-GX | Ciba ® | 0871651V6 | N/A | Y |
| fb28 | Sigma-Aldrich ® | f3543—5 g | N/A | Y |
| fluorescein puriss | Riedel-de haen ® | 32615 | 332.31 | Y |
| solophenyl flavine 7GFE 500% | Huntsman International LLS | 1485385V6 | N/A | N |
| pontamine fast orange 6RN | pylam products ™ | N/A | N/A | N |
| rose Bengal | Sigma-Aldrich ® | 330000—1 g | 1017.65 | Y |
| sulforhodamine 101 | Sigma-Aldrich ® | S7635—100 mg | 606.7 | Y |
| tinopal CBS-X | Ciba ® | 0292830V6 | N/A | N |
| congo red | Sigma-Aldrich ® | C-6767 | 696.7 | Y |
| pontamine sky blue 6BX | Pylam Products ™ | N/A | N/A | N |
| permalite flavine 7GFF | N/A | N/A | N/A | Y |
| | A.G. Scientific Inc. | B-1003 | N/A | Y |

TABLE 10

| Substrates | Description |
| --- | --- |
| VANISPERSE (lignin derivative) | Lignin mimics |
| Xylan | Hemi-cellulosic biomass |
| Starch | Alpha-linked carbohydrate polymer |
| AVICEL ® | Beta-linked crystalline carbohydrate polymer |
| Kelig | Lignin mimics |
| Glucose | Product of hydrolysis |
| WGS Biomass 3% | FCD assay substrate |
| Cellobiose | Intermediate of hydrolysis |
| Xylose | Product of hydrolysis |
| beta-glucan | Biomass-like carbohydrate polymer |
| AZCL-HE-cellulose | Biomass-like carbohydrate polymer |

Pre-Scan of all the Dyes and Substrates.

The spectra of only the substrates of Table 10 or fluorescent dyes of Table 9 were obtained. Spectra were plotted as fluorescence units over the wavelength range of 400-500 nm. The results indicated that the substrates have low fluorescence in the wavelength range in general, only reaching approximately 1500 fluorescence units except Kelig and AVICEL®, which were able to max at 4000-5000. However, the Kelig and AVICEL® spectra were considered background com- Surprisingly, the mixture of AVICEL® and FB28 achieved a highly fluorescent material, with λmax at 450 nm and reaching up to 500 k fluorescene units. This indicated excellent parameters to review the digestion of AVICEL® using fluorescent dye to a very sensitive and detailed level.

Compared to the mixture of FB28+WGS 3% PCS, the following materials were more fluorescent: starch, glucose, xylose, and Kelig. Both glucose and xylose are monocomponent, transparent solutions the fluorescene of which could be much less upon placing into a pigment-rich liquor such as WGS-PCS. In this experiment, the level of starch and Kelig were made equal to the concentration of PCS. However, in the assay condition in accordance with the present disclosure, these two substances were either negligible or at a significantly lower level, as revealed by the component analysis of PCS. Prototype testing the HPLC results (of glucose and cellobiose yield) correlated well to what the assay predicted, which proved that the influence of lignin was minimized.

Conclusions

Together, various combinations of dye-substrate were excited at 360 nm and their emission from 400-500 nm were recorded. No significant background fluorescence from the substrates were found. Some of the pairs were highly fluorescent, such as WGS PCS-BLANKOPHOR® brand brightener, and AVICEL®-FB28, which could be beneficial for other purposes such as setting up kinetic assays. Finally, the studies found that the disturbances from Kelig and other components to FB28-PCS absorbance to be minimum, and were not entirely avoided.

The fluorescent cellulose decay assay was found to be fast with excellent accuracy (+/−5-10%) for methods of detecting the enzymatic hydrolysis level of PCS compared to the HPLC assay. High-throughput screening of enzymes of interest such as cellulases and polypeptides of interest such as GH61 polypeptide having cellulolytic enhancing activity is now possible as well as rendering a convenient QC standard using the methods of the present disclosure.

Example 3

Chemicals, Substrates, Enzymes

Fluorescent brightener 28 (F3543) was obtained from Sigma-Aldrich®. SOFTANOL® 90 (INEOS), PEG3350, PEG200, TWEEN® 80, and TRITON® X-100 were used as surfactants. Substrate was provided as washed ground sieved—NREL PCS from lot KCMF1752-96. CP1 from CZP0001 of SaMe MF268 was used and freshly diluted the day of use.

Test/Analysis

PCS-A (3%) with 150 μM FB28 were used in methods according to the present disclosure. In COSTAR® 3364 plates usually 240 μl of 3.75% WGS-NREL PCS, 30 μl of 500 mM sodium acetate buffer at pH 5.0 with 10 mM manganese sulfate, and 30 μl of the enzyme mix were mixed by pipetting 3 times up and down. If citrate was used as a buffer the buffer volume was reduced to 15 μl and 1 M sodium citrate at pH 4.6 was used. This resulted in a final pH of 5.0. For pH trials different buffers were used as a 500 mM stock solution with or without addition of 10 mM divalent cations: acetate for pH 4 to pH 5, BIS-TRIS for pH 6 to 7, TRIS for pH 8. Additives were added by decreasing the enzyme volume and adding the additive as a stock solution.

The plates were sealed with an ALPS 3000 (165° C. for 1.5 seconds) and incubated at 50° C. for 72 hours with a manual inversion twice a day. Fluorescence emission was read on a Beckman DTX reader through the bottom of the plate with an excitation filter at 360 nm and an emission filter at 465 nm. The fluorescence emission intensity was reported in arbitrary units (AU). The estimated conversion was calculated from the fluorescence emission intensity as:

$$100 \cdot \frac{\overline{AU}_0 - AU}{(\overline{AU}_0 - \overline{AU}_{50})_{72h}}$$

With $AU$ = arbitrary units of fluorescence emission intensity $\overline{AU}_0$ = average of wells without enzyme addition (highest $AU$ value)

$\overline{AU}_{50}$ = avereage of wells with 50 mg $CP1/g$ cellulose

As indicated in some cases a normalization using the respective addition of additives or buffer to no enzyme or 50 mg/g enzyme sample was performed.

At 72 hours the samples were filtered and analyzed by HPLC for glucose and cellobiose. These samples were usually taken from the same plates as the assay in accordance with the present disclosure, which means that FB28 was present during hydrolysis.

In some experiments (as indicated in the text) a final volume of 250 μl was used. Furthermore in the last plates also 10 mM sodium azide for preservation of the plates was included.

The coefficient of variation (CV) was typically calculated only from triplicate samples. If average CVs are given this relates to the average of all triplicate CVs of one experiment. Samples with a conversion below 10% were excluded.

Comparison of Citrate and Acetate Buffer at pH 5

An assay in accordance with the present disclosure was tested on the same PCS-A with addition of two different buffer systems. The first trials using 1 M citrate buffer showed that at a pH of 5 of the 1 M stock solution the final pH at 50 mM was 5.8. Hence, the 1 M citrate buffer was adjusted to pH 4.6 to give a final pH of 5.0. The cellulase was added as a typical dose response in accordance with the present disclosure with acetate or citrate buffer at a final pH of 5.0. Fluorescent cellulose decay ("FCD") conversion was calculated from fluorescence emission and HPLC conversion was calculated from the glucose and cellobiose measured after the FCD assay. The CP1 dose response using either acetate or citrate showed a close fit of the conversion estimated from FCD and calculated from the HPLC. The FCD and HPLC data were similar except for an enzyme loading of 4.1 and 5.1 mg/g where a significant difference was observed. Citrate and acetate were only significantly different at an enzyme loading of 2.1 mg/g in the HPLC analysis. In comparison the FCD estimate showed more significant differences in the enzyme loading range from 2.1 to 5.1 mg/g. This was due to a lower coefficient of variation (CV) of the FCD assay in this range. The CVa of FCD and HPLC analysis were compared where, the CVs from each triplicate were plotted against the respective HPLC conversion for the FCD analysis and the HPLC analysis. The data demonstrated that the HPLC had a nearly constant CV of around 5% over the whole assay range. In contrast, the FCD assay had a lower CV at high conversion, but its CV increased with decreasing conversion. Hence, this assay can be very effective at high conversion and can show small significant difference better than HPLC.

pH Range of 4 to 8

An assay in accordance with the present disclosure was tested at pHs ranging from 4 to 8. This was done with addition of 10 mM $CaCl_2$. Manganese was not used, because at higher pH manganese was oxidized to $Mn^{3+}$ turning the buffer brownish or black. After 72 hours hydrolysis the fluorescence emission of the sample without enzyme addition was unchanged by pH. A clear decrease of the fluorescence emission intensity was observed from pH 5 to pH 4. The pH range from 4 to 5 was tested in 0.1 pH steps and a strong decrease was observed below pH 4.7.

Due to this strong decrease in fluorescence the pH needs to be controlled in the assay and assays should preferably be run above pH 5.

Comparing the FCD estimated conversion to the HPLC conversion it was clear that the assay can be used in the range of pH 5 to 6. Normalization with the no CP1 addition control at the respective pH did not improve the prediction at the other pH values. However, normalization with the no and 50 mg/g CP1 addition at the respective pH improved the prediction for pH 7 considerably. The conversion at pH 8 was below 20% so this pH was of no real relevance.

The dose response in tests showed a good fit for the pH 4.9 to pH 6 data with the usual normalization. The fit also improved for pH 7 with the normalization with both controls at the respective pH. After usual normalization the pH curves from FCD indicated clearly the maximum in the range from pH 4.9 to 8, but the FCD estimate was too low at pH 7. A normalization with both controls at the respective pH led to a better fit of the data from pH 4 to pH 7. At pH 7 and pH 8 the 50 mg/g CP1 did not lead to a complete hydrolysis of the sample. If the FCD assay shall be applied at pH 7 and 8, higher enzyme loading is needed in order to improve the conversion prediction.

A second experiment with a loading of 4 mg CP1 per g cellulose was run in the pH range of 5 to 7 with 0.5 pH intervals. The obtained conclusions and results were consistent with the first experiment. In this second experiment the assay volume was reduced to 250 µl and 10 mM sodium azide was added.

It was determined that assays in accordance with the present disclosure can be used from pH 5 to pH 6. For pH 7 a normalization with the controls at this pH is needed. Below pH 4.7 the FB28 fluorescence intensity decreases strongly probably due to a protonation of the fluorophores.

Temperature from 30 to 60° C.

An assay in accordance with the present disclosure was performed at 30, 50, 55, and 60° C. using CP1. It was determined that a linear model can be used to compare within each temperature from 50 to 60° C. A comparison of 60 to 50 and 55° C. showed 60° C. samples up to 7% better than they actually were. In embodiments, a comparison between temperatures was excellent between 50 and 55° C.

Addition of Salts

Different sodium chloride concentrations are often present in enzyme samples, especially after purification by anion exchange columns and elution with a salt gradient. Hence, the effect of 0 to 400 mM NaCl addition to the FCD assay was investigated. The fluorescence emission showed that the fluorescence emission of the sample without enzyme addition decreased with increasing sodium chloride concentration. The 0 hour samples of CP1 loadings from 3 to 5 mg/g cellulose followed this trend closely. After 73 hours of hydrolysis the fluorescence emission of all CP1 loadings was rather independent of the salt concentration. The usual assay normalization would indicate that the conversion was rather unaffected by the salt addition. However, this was not observed. In the HPLC assay a decrease with increasing salt concentration was observed. The change in the base fluorescence emission signal can be corrected by measuring the no enzyme sample always at the respective salt concentration. Using this normalization an assay estimate was obtained which compares well with a dose response with no salt addition shown by plotting FCD estimated conversion versus HPLC measured conversion. It was observed that the FCD conversion was lower than the HPLC measured conversion, but the same decreasing trend was visible at all loadings. The deviation increased above approximately 5% at 400 mM NaCl. From 0 to 200 mM it was similar for all loadings and below approximately 6%. The decreased conversion at higher salt concentration seemed related to an increase in cellobiose, which might indicate a lower BG activity at higher salt concentration.

After enzyme purification by ion exchange chromatography the salt concentration in the eluted fraction is usually unknown and increases with the fraction number. Hence, it is not feasible to correct with a certain sodium chloride concentration in the no enzyme addition control. Instead it might be useful to use the value measured directly after starting the assay at 0 hour. It was shown that this value was closely correlated to the no enzyme addition fluorescence emission at the respective salt concentration. However, due to the lack of equilibration these values were higher than the equilibrated ones of the no enzyme addition control.

Here, the FCD conversion was calculated with the formula:

$$100*(AU_{x,0h}-AU_{x,72h})/(AU_{x,0h}-AU_{50,72h})$$

It was also shown that the data was even more close to the HPLC conversion than with a normalization using the no enzyme control at each NaCl concentration. The assay conversion closely followed the HPLC measured conversion even up to 400 mM NaCl. The 3 mg/g loading still showed a deviation that increased with salt concentration up to +5%. Hence, this method is recommended for samples containing different levels of salt.

It was found that the addition of salts decreased fluorescence emission. If the assay conversion calculation was corrected by measuring each no enzyme addition control at the respective salt concentration a good correlation between the assay estimated and HPLC measured conversion was obtained up to 200 mM sodium chloride. An excellent correlation can be obtained by using the fluorescence emission right after starting the assay. The FCD estimate was then calculated by: $100*(AU_{x,0h}-AU_{x,72h})/(AU_{x,0h}-AU_{50,72h})$. The data fit very well up to 400 mM sodium chloride. However, this method was difficult at low levels of conversion, because the baseline fluorescence dropped after the start of the assay to a new baseline. This drop needed to be eliminated first before this normalization could be generally used.

Addition of Interfering Agent

Tests were performed which indicated that ethanol did not interfere with the fluorescence emission of the indicator constituent. The methods in accordance with the present disclosure were thus excellent for use in screening for ethanol tolerant cellulases.

Addition of Surfactants

Tests were performed on surfactants added to the methods in accordance with the present disclosure. It was found that it was possible to screen surfactants in a small scale assay followed by HPLC analysis, but using the fluorescent brightener for the determination of conversion was difficult. Without being bound by the present disclosure it is believed that surfactants may modify binding of FB28 to the cellulose. For some surfactants (SOFTANOL® 90, TWEEN® 80, TRITON® X-100) normalization with addition of the surfactant to the no enzyme control worked well. Polyethylene glycols seemed to change the FCD results considerably and cannot be used without an extra calibration.

It is to be appreciated that the foregoing is illustrative and not limiting of the invention, and that various changes and modifications to the embodiments described above will be apparent to those skilled in the art. Such changes and modifications can be made without departing from the spirit and scope of the present invention, and it is therefore intended that such changes and modifications be covered by the following claims. Also, it should be appreciated that to the extent that any terms and/or definitions herein may differ from similar terms or definitions of any application incorporated herein by reference, the terms or definitions herein control.

The present disclosure is further described by the following numbered paragraphs:

[1] A method of analyzing cellulose decay in cellulosic material hydrolysis comprising: hydrolyzing the cellulosic material containing cellulose in a reaction medium including an indicator constituent under conditions where the indicator constituent will stain the cellulose; and detecting a signal from the indicator constituent, wherein the intensity of the signal indicates the amount of cellulose hydrolyzed by enzyme of interest.

[2] The method of paragraph 1, comprising the steps of: (a) contacting the cellulosic material with the indicator constituent to form a mixture; and (b) simultaneous to or subsequent to step (a) contacting the mixture with the reaction medium comprising the enzyme of interest.

[3] The method of paragraph 1 or 2, wherein the indicator constituent is a fluorescent indicator compound comprising—a fluorophore, a high wavelength fluorophore, a stilbene derivative, a styryl derivative of benzene and biphenyl, a pyrazoline, a bis(benzoxazol-2-yl) derivative, a coumarin, a carbostyril, or a diaminostilbene; or a mixture thereof.

[4] The method of paragraph 3, wherein the diaminostilbene is 4,4'-bis[[4-anilino-6-bis[(2-hydroxyethyl)amino]-s-triazin-2-yl]amino]-2,2'-stilbenedisulfonic acid or tetrasulfonated derivative of 4,4ĩ'-diamino-stilbene-2,2ĩ'-disulphonic acid.

[5] The method of paragraph 1 or 2, wherein the indicator constituent is 4,4'-bis[[4-anilino-6-bis[(2-hydroxyethyl)amino]-s-triazin-2-yl]amino]-2,2'-stilbenedisulfonic acid.

[6] The method of any of paragraphs 1-5, wherein the reaction medium has a volume of 10-1000 µl.

[7] The method of any of paragraphs 1-5, wherein the reaction medium has a volume of 100-500 µl.

[8] The method of any of paragraphs 1-7, wherein the reaction medium is disposed within a multi-well plate comprising at least two wells.

[9] The method of paragraph 8, wherein the plate is made of polypropylene.

[10] The method of paragraph 8, wherein the multi-well plate comprises 12, 24, 96, 384, 1,536, or 3,456 wells.

[11] The method of any of paragraphs 1-10, wherein the enzyme of interest is added to each well in an amount of 0.1 ng to 10 mg.

[12] The method of any of paragraphs 1-11, wherein at least 96 enzymes of interest are tested for cellulose hydrolysis activity in less than five minutes after the hydrolysis step.

[13] The method of any of paragraphs 1-12, wherein the step of hydrolysis is performed at 10° C. to 90° C.

[14] The method of any of paragraphs 1-13, wherein the reaction medium is disposed in at least two sealed wells.

[15] The method of any of paragraphs 1-14, wherein the step of detecting occurs from below the reaction medium.

[16] The method of any of paragraphs 1-15, wherein the reaction medium has a pH of 4 to 8.

[17] The method of any of paragraphs 1-16, wherein the reaction medium comprises 0-500 mM of salt.

[18] The method of any of paragraphs 1-17, wherein the reaction medium comprises a buffer system.

[19] The method of any of paragraphs 1-18, wherein the enzyme of interest is added in an amount sufficient to hydrolyze 20% to 100% of the cellulosic material.

[20] The method of any of paragraphs 1-18, wherein the enzyme of interest is added in an amount sufficient to hydrolyze the cellulosic material.

[21] The method of any of paragraphs 1-20, wherein the reaction medium comprises one or more surfactants.

[22] The method of any of paragraphs 1-21, wherein the reaction medium has about 0.5% to about 10% total solids.

[23] The method of any of paragraphs 1-22, wherein the enzyme of interest comprises one or more (several) enzymes selected from the group consisting of a cellulase, a hemicellulase, an esterase, a protease, a laccase, and a peroxidase.

[24] The method of paragraph 23, wherein the cellulase is one or more enzymes selected from the group consisting of an endoglucanase, a cellobiohydrolase, and a beta-glucosidase.

[25] The method of paragraph 23, wherein the hemicellulase is one or more enzymes selected from the group consisting of a xylanase, an acetyxylan esterase, a feruloyl esterase, an arabinofuranosidase, a xylosidase, and a glucuronidase.

[26] The method of any of paragraphs 1-24, wherein the enzyme of interest comprises: (a) wild-type exo-cellobiohydrolase, wild-type endo-1,4-β-glucanase, wild-type exo-1,4-β-glucosidase, wild-type cellobiase, or a combination thereof; (b) a mutated exo-cellobiohydrolase, mutated endo-1,4-β-glucanase, mutated exo-1,4-β-glucosidase, mutated cellobiase, or a combination thereof; (c) a variant exo-cellobiohydrolase, variant endo-1,4-β-glucanase, variant exo-1,4-β-glucosidase, variant cellobiase, or a combination thereof, (d) fragment having the activity of (a), (b), or (c); or (e) combinations of (a), (b), (c), or (d).

[27] The method of any of paragraphs 1-26, comprising the steps of: (a) contacting cellulosic material with an indicator constituent to form a mixture; and (b) simultaneous to or subsequent to step (a) contacting the mixture with a reaction medium comprising polypeptide of interest.

[28] The method of paragraph 27, wherein the polypeptide of interest is a polypeptide from one or more glycoside hydrolase families.

[29] The method of paragraph 28, wherein the polypeptide is a GH61 polypeptide having cellulolytic enhancing activity.

[30] A method of determining whether enzyme of interest affects cellulose hydrolysis, comprising the steps of: hydrolyzing the cellulosic material in a reaction medium including a fluorescent indicator compound under conditions where the fluorescent indicator compound will affect the cellulose and produce an optical signal indicative of the presence of cellulose; and determining whether the hydrolyzed reaction has a desired optical signal, wherein the desired optical signal indicates cellulolytic activity of the enzyme of interest and/or the amount of cellulose hydrolyzed by the enzyme of interest.

[31] The method of paragraph 30, further comprising the steps of, prior to the hydrolysis: (a) contacting cellulosic material with a fluorescent indicator compound to form a mixture; (b) simultaneous to or subsequent to step (a) contacting the mixture with a reaction medium suitable for cellulose hydrolysis comprising the enzyme of interest.

[32] The method of paragraph 30 or 31, wherein the enzyme/polypeptide of interest comprises one or more (several) selected from the group consisting of a cellulase, a polypeptide having cellulolytic enhancing activity, a hemicellulase, an esterase, a protease, a laccase, and a peroxidase.

[33] The method of paragraph 32, wherein the cellulase is one or more enzymes selected from the group consisting of an endoglucanase, a cellobiohydrolase, and a beta-glucosidase.

[34] The method of paragraph 32, wherein the hemicellulase is one or more enzymes selected from the group consisting of a xylanase, an acetyxylan esterase, a feruloyl esterase, an arabinofuranosidase, a xylosidase, and a glucuronidase.

[35] The method of any of paragraphs 30-33, wherein the enzyme of interest comprises: (a) wild-type exo-cellobiohydrolase, wild-type endo-1,4-β-glucanase, wild-type exo-1,4-β-glucosidase, wild-type cellobiase, or a combination thereof; (b) a mutated exo-cellobiohydrolase, mutated endo-1,4-β-glucanase, mutated exo-1,4-β-glucosidase, mutated cellobiase, or a combination thereof; (c) a variant exo-cellobiohydrolase, variant endo-1,4-β-glucanase, variant exo-1,4-β-glucosidase, variant cellobiase, or a combination thereof, (d) fragment having the activity of (a), (b), or (c); or (e) combinations of (a), (b), (c), or (d).

[36] A high-throughput method of analyzing enzymes and/or polypeptides of interest, comprising the steps of: (a) contacting biomass with a fluorescent compound to form a mixture; (b) simultaneous to or subsequent to step (a) contacting the mixture with a reaction medium comprising enzyme of interest and/or polypeptides of interest, (c) hydrolyzing the biomass including cellulose in a reaction medium under conditions where the fluorescent indicator compound will stain the cellulose; and (d) detecting a signal from the fluorescent indicator compound, wherein the intensity of the signal predicts a quality parameter of the enzyme of interest and/or polypeptides of interest in biomass hydrolysis, and wherein the reaction mixture is disposed within a multi-well plate comprising at least two wells.

[37] The method of paragraph 36, wherein the multi-well plate is disposed within a system further comprising a pipette.

[38] The method of paragraph 36 or 37, wherein the system further comprises a plate reader.

[39] The method of any of paragraphs 36-38, wherein the quality parameter is cellulolytic activity indication or a quality control parameter.

[40] The method of any of paragraphs 36-39, wherein the biomass is a lignocellulosic material.

[41] The method of any of paragraphs 36-40, wherein the enzyme/polypeptide of interest comprises one or more (several) selected from the group consisting of a cellulase, a polypeptide having cellulolytic enhancing activity, a hemicellulase, an esterase, a protease, a laccase, and a peroxidase.

[42] The method of paragraph 41, wherein the cellulase is one or more enzymes selected from the group consisting of an endoglucanase, a cellobiohydrolase, and a beta-glucosidase.

[43] The method of paragraph 41, wherein the hemicellulase is one or more enzymes selected from the group consisting of a xylanase, an acetyxylan esterase, a feruloyl esterase, an arabinofuranosidase, a xylosidase, and a glucuronidase.

[44] The method of any of paragraphs 36-42, wherein the enzyme of interest comprises: a) wild-type exo-cellobiohydrolase, wild-type endo-1,4-β-glucanase, wild-type exo-1,4-β-glucosidase, wild-type cellobiase, or a combination thereof; b) a mutated exo-cellobiohydrolase, mutated endo-1,4-β-glucanase, mutated exo-1,4-β-glucosidase, mutated cellobiase, or a combination thereof; c) a variant exo-cellobiohydrolase, variant endo-1,4-β-glucanase, variant exo-1,4-β-glucosidase, variant cellobiase, or a combination thereof, d) fragment having the activity of a), b) or c); or e) combinations of a), b), c), or d).

[45] A method of determining whether an enzyme of interest affects cellulose hydrolysis, comprising the steps of: (a) contacting biomass with a fluorescent indicator compound to form a mixture; (b) simultaneous to or subsequent to step (a) contacting the mixture with a reaction medium suitable for cellulose hydrolysis comprising enzyme of interest and/or polypeptide of interest, (c) hydrolyzing the biomass containing cellulose in a reaction medium under conditions where the fluorescent indicator compound will bind to cellulose and produce an optical signal indicative of the presence of cellulose; and (d) determining whether the hydrolyzed reaction has a desired optical signal, wherein the desired optical signal indicates that the enzyme of interest and/or polypeptide of interest affects cellulose hydrolysis.

[46] The method of paragraph 45, comprising the step of providing an enzyme/polypeptide of interest.

[47] The method of paragraph 45 or 46, wherein the enzyme/polypeptide of interest comprises one or more (several) selected from the group consisting of a cellulase, a polypeptide having cellulolytic enhancing activity, a hemicellulase, an esterase, a protease, a laccase, and a peroxidase.

[48] The method of paragraph 47, wherein the cellulase is one or more enzymes selected from the group consisting of an endoglucanase, a cellobiohydrolase, and a beta-glucosidase.

[49] The method of paragraph 47, wherein the hemicellulase is one or more enzymes selected from the group consisting of a xylanase, an acetyxylan esterase, a feruloyl esterase, an arabinofuranosidase, a xylosidase, and a glucuronidase.

[50] The method of any of paragraphs 45-48, wherein the enzyme of interest comprises an enzyme selected from the group consisting of: (a) wild-type exo-cellobiohydrolase, wild-type endo-1,4-β-glucanase, wild-type exo-1,4-β-glucosidase, wild-type cellobiase, or a combination thereof; (b) a mutated exo-cellobiohydrolase, mutated endo-1,4-β-glucanase, mutated exo-1,4-β-glucosidase, mutated cellobiase, or a combination thereof; (c) a variant exo-cellobiohydrolase, variant endo-1,4-β-glucanase, variant exo-1,4-β-glucosidase, variant cellobiase, or a combination thereof, (d) fragment having the activity of (a), (b), or (c); or (e) combinations of (a), (b), (c), or (d).

[51] A method of analyzing enzyme performance comprising the steps of: (a) contacting lignocellulosic material with a fluorescent indicator compound to form a mixture; (b) simultaneous to or subsequent to step (a) contacting the mixture with a reaction medium comprising enzyme of interest; (c) hydrolyzing the lignocellulosic material containing cellulose in the reaction medium under conditions where the fluorescent indicator compound will stain the cellulose; and (d) detecting a signal from the fluorescent indicator compound, wherein the intensity of the signal indicates the amount of cellulose hydrolyzed by the enzyme.

[52] The method of paragraph 51, wherein the enzyme performance is cellulose decay in lignocellulose hydrolysis.

[53] The method of paragraph 51 or 52, wherein the enzyme of interest comprises one or more (several) enzymes selected from the group consisting of a cellulase, a polypeptide having cellulolytic enhancing activity, a hemicellulase, an esterase, a protease, a laccase, and a peroxidase.

[54] The method of paragraph 52, wherein the cellulase is one or more enzymes selected from the group consisting of an endoglucanase, a cellobiohydrolase, and a beta-glucosidase.

[55] The method of paragraph 52, wherein the hemicellulase is one or more enzymes selected from the group consisting of a xylanase, an acetyxylan esterase, a feruloyl esterase, an arabinofuranosidase, a xylosidase, and a glucuronidase.

[56] The method of any of paragraphs 51-54, wherein the enzyme is selected from the group consisting of: a) wild-type exo-cellobiohydrolase, endo-1,4-β-glucanase, exo-1,4-β-glucosidase, cellobiase, or combinations thereof; b) a mutated exo-cellobiohydrolase, endo-1,4-β-glucanase, exo-1,4-β-glucosidase, cellobiase, or combinations thereof; and c) a variant exo-cellobiohydrolase, variant endo-1,4-β-glucanase, variant exo-1,4-β-glucosidase, variant cellobiase, or combinations thereof, d) fragments having activity of a), b), or c); and e) mixtures of a), b), c), d) or e).

[57] A method of analyzing cellulose decay in biomass hydrolysis, comprising the steps of: (a) contacting biomass with a fluorescent indicator compound to form a mixture; (b) simultaneous to or subsequent to step (a) contacting the mixture with a reaction medium comprising enzyme of interest, (c) hydrolyzing the biomass including cellulose in a reaction medium under conditions where the fluorescent indicator compound will bind to cellulose; and (d) detecting a signal from the fluorescent indicator compound, wherein the intensity of the signal indicates a quality parameter of the enzyme of interest in biomass hydrolysis.

[58] The method of paragraph 57, wherein the method occurs in a system.

[59] The method of determining whether an enzyme of interest affects cellulose hydrolysis, comprising the steps of: (a) contacting cellulosic material with a fluorescent indicator compound to form a mixture; (b) simultaneous to or subsequent to step (a) contacting the mixture with a reaction medium suitable for cellulose hydrolysis comprising enzyme of interest; (c) hydrolyzing the cellulosic material in a reac-

[60] A method of analyzing cellulose decay in lignocellulose hydrolysis, comprising the steps of: (a) contacting lignocellulose with a fluorescent indicator compound to form a mixture; (b) simultaneous to or subsequent to step (a) contacting the mixture with a reaction medium comprising enzyme of interest; (c) hydrolyzing the corn stover containing cellulose in the reaction medium under conditions where the fluorescent indicator compound will bind to the cellulose; and (d) detecting a signal from the fluorescent indicator compound, wherein the intensity of the signal indicates the amount of cellulose hydrolysed by the enzyme.

[61] A system for evaluating enzyme performance comprising: at least one reaction area, wherein the reaction area for analyzing cellulose decay in lignocellulose hydrolysis, the reaction area comprising: at least one well for: (a) contacting lignocellulosic material with a fluorescent indicator compound to form a mixture; (b) simultaneous to or subsequent to step (a) contacting the mixture with a reaction medium comprising enzyme of interest; (c) hydrolyzing the lignocellulosic material containing cellulose in the reaction medium under conditions where the fluorescent indicator compound will stain the cellulose; and at least one detector suitable for detecting a signal from the fluorescent indicator compound, wherein the intensity of the signal indicates the amount of cellulose hydrolyzed by the enzyme.

[62] The system of paragraph 61, wherein the detector is located below the reaction medium.

[63] A method of normalizing methods for determining the amount of target cellulose in a biological sample, the method comprising: (a) measuring the fluorescent intensity of target cellulose in a sample in a reaction volume; (b) determining the average fluorescent intensity of a hydrolysis of substrate without the addition of enzyme; and (c) normalizing the target cellulose measurement by subtracting the fluorescent intensity of target cellulose from the average intensity of a hydrolysis reaction without addition of enzyme.

[64] The method of with paragraph 63, wherein the substrate is PCS.

[65] A method of normalizing fluorescent intensity data, the method comprising the steps of: (a) determining the average fluorescent intensity of a hydrolysis reaction of PCS without the addition of enzyme; and (b) normalizing the fluorescent intensity of one or more second hydrolysis reactions using the fluorescent intensity determined in step (a).

[66] A method of determining whether an enzyme of interest and polypeptide of interest affects cellulose hydrolysis, comprising the steps of: hydrolyzing the cellulosic material in a reaction medium including fluorescent indicator compound under conditions where the fluorescent indicator compound will affect the cellulose and produce an optical signal indicative of the presence of cellulose; and determining whether the hydrolyzed reaction has a desired optical signal, wherein the desired optical signal indicates cellulolytic activity of the enzyme of interest and polypeptide of interest and/or the amount of cellulose hydrolyzed by the enzyme of interest and polypeptide of interest.

What is claimed is:

1. A method of analyzing cellulose decay or enzyme performance in lignocellulosic material hydrolysis, the method comprising:
   (a) contacting lignocellulosic material with a fluorescent indicator compound to form a mixture;
   (b) simultaneous to or subsequent to step (a), contacting the mixture with a reaction medium comprising an enzyme of interest to form a reaction mixture;
   (c) hydrolyzing the lignocellulosic material in the reaction medium under conditions where the fluorescent indicator compound will bind to cellulose from the lignocellulosic material; and
   (d) detecting a decrease in fluorescent signal intensity from the reaction mixture, wherein the decrease in the intensity indicates the amount of cellulose hydrolyzed by the enzyme of interest or indicates a quality parameter of the enzyme of interest.

2. The method of claim 1, wherein the fluorescent indicator compound is a stilbene derivative, a styryl derivative of benzene and biphenyl, a pyrazoline, a bis(benzoxazol-2-yl) derivative, a coumarin, or a carbostyril.

3. The method of claim 1, wherein the fluorescent indicator compound is 4,4'-bis[[4-anilino-6-bis[(2-hydroxyethyl)amino]-s-triazin-2-yl]amino]-2,2'-stilbenedisulfonic acid.

4. The method of claim 1, wherein the enzyme of interest comprises one or more enzymes selected from the group consisting of a cellulase, a hemicellulase, an esterase, a protease, a laccase, and a peroxidase.

5. The method of claim 1, wherein the reaction medium further comprises a polypeptide having cellulolytic enhancing activity.

6. The method of claim 1, wherein the fluorescent indicator compound is a diaminostilbene derivative.

7. The method of claim 1, wherein the fluorescent indicator compound is 4-methylumbelliferone.

8. The method of claim 1, wherein the reaction mixture has about 0.5% to about 10% total solids.

* * * * *